(12) United States Patent  
Jackowski et al.

(10) Patent No.: US 8,952,000 B2
(45) Date of Patent: Feb. 10, 2015

(54) CHOLESTEROL ABSORPTION INHIBITOR AND OMEGA 3 FATTY ACIDS FOR THE REDUCTION OF CHOLESTEROL AND FOR THE PREVENTION OR REDUCTION OF CARDIOVASCULAR, CARDIAC AND VASCULAR EVENTS

(75) Inventors: George Jackowski, Kettleby (CA); Rachelle MacSweeney, Kettleby (CA); Nisar Shaikh, Mississauga (CA); Jason Yantha, Brampton (CA); Valerie Schini-Kerth, Fessenheim-le-Bas (FR)

(73) Assignee: Pivotal Therapeutics Inc., Woodbridge, Ontario (CA)

( * ) Notice: Subject to any disclaimer, the term of this patent is extended or adjusted under 35 U.S.C. 154(b) by 0 days.

(21) Appl. No.: 13/584,403

(22) Filed: Aug. 13, 2012

(65) Prior Publication Data

US 2013/0040927 A1  Feb. 14, 2013

Related U.S. Application Data

(63) Continuation-in-part of application No. PCT/US2012/025003, filed on Feb. 14, 2012.

(60) Provisional application No. 61/457,268, filed on Feb. 16, 2011.

(51) Int. Cl.
*A61K 31/5377* (2006.01)
*A61K 31/397* (2006.01)
(Continued)

(52) U.S. Cl.
CPC ............... *A61K 31/397* (2013.01); *A61K 45/06* (2013.01); *A61K 31/202* (2013.01); *A61K 31/557* (2013.01)
USPC ..................................... 514/210.02

(58) Field of Classification Search
None
See application file for complete search history.

(56) References Cited

U.S. PATENT DOCUMENTS 4,666,701 A * 5/1987 Horrobin et al. ............. 514/558
4,977,187 A   12/1990 Horrobin
(Continued)

FOREIGN PATENT DOCUMENTS

EP  1800675  7/2007
EP  2085089  5/2009
(Continued)

OTHER PUBLICATIONS

Evans, M. et al. "Medical Lipid-Regulating Therapy: Current Evidence, Ongoing trials and future developments" in Drugs, 2004, vol. 64, Issue 11, p. 1181-1196.*

(Continued)

*Primary Examiner* — San-Ming Hui
*Assistant Examiner* — Jeanmarie Calvillo
(74) *Attorney, Agent, or Firm* — Ferris H. Lander, Inc.

(57) ABSTRACT

A composition and a method of treatment utilizing a combination of lipid lowering cholesterol absorption inhibitors, e.g. azetidinones, with mixtures of an omega-3 fatty acid formulation containing about 90% or more omega 3 fatty acids by weight including a combination of Eicosapentaenoic acid (EPA), Docosapentaenoic acid (DPA) and Docosahexaenoic acid (DHA) in a weight ratio of EPA:DHA of from 5.7 to 6.3, wherein the sum of the EPA, DHA and DPA represent about 82% by weight of the total formulation and about 92% of the total omega 3 fatty acid content of the composition are taught. EPA+DHA are about 80% of the total formulation and about 89% of the total omega 3 fatty acid content of the composition. The formulation may further contain specific amounts of arachidonic acid (AA), stearidonic acid (SDA), and alpha-linolenic acid (ALA).

20 Claims, 15 Drawing Sheets

(51) Int. Cl.
  *A61K 45/06* (2006.01)
  *A61K 31/202* (2006.01)
  *A61K 31/557* (2006.01)

(56) References Cited

U.S. PATENT DOCUMENTS

| | | | |
|---|---|---|---|
| 5,116,624 A | 5/1992 | Horrobin | |
| 5,130,061 A | 7/1992 | Cornieri | |
| 5,149,851 A | 9/1992 | Stout | |
| 5,198,468 A | 3/1993 | Horrobin | |
| 5,214,062 A | 5/1993 | Mark | |
| 5,502,077 A | 3/1996 | Breivik | |
| 5,562,913 A | 10/1996 | Horrobin | |
| 5,698,594 A | 12/1997 | Breivik | |
| 5,738,871 A | 4/1998 | Story | |
| 5,804,944 A | 9/1998 | Alberkrack | |
| 5,902,829 A | 5/1999 | Schneider | |
| 6,150,411 A | 11/2000 | Stordy | |
| 6,177,470 B1 | 1/2001 | Horrobin | |
| 6,184,251 B1 | 2/2001 | Stordy | |
| 6,245,811 B1 | 6/2001 | Horrobin | |
| 6,284,268 B1 | 9/2001 | Mishra | |
| 6,331,568 B1 | 12/2001 | Horrobin | |
| 6,369,098 B1 | 4/2002 | Pershadsingh | |
| 6,384,077 B1 | 5/2002 | Peet | |
| 6,610,740 B1 | 8/2003 | Wakefield | |
| 6,624,195 B2 | 9/2003 | Horrobin | |
| 6,689,812 B2 | 2/2004 | Peet | |
| 6,846,942 B2 | 1/2005 | Rubin | |
| 6,998,501 B1 | 2/2006 | Wright | |
| 7,119,118 B2 | 10/2006 | Peet | |
| 7,179,793 B2 | 2/2007 | Ewart | |
| 7,342,089 B2 | 3/2008 | Sharma | |
| 7,378,444 B2 | 5/2008 | Goodman | |
| 7,462,643 B1 | 12/2008 | Pamparana | |
| 7,511,070 B2 | 3/2009 | Grainger | |
| 7,582,674 B2 | 9/2009 | Raederstorff | |
| 7,619,002 B2 | 11/2009 | Shibuya | |
| 7,652,068 B2 | 1/2010 | Feuerstein | |
| 7,704,518 B2 | 4/2010 | Tamarkin | |
| 7,772,277 B2 | 8/2010 | Almarsson | |
| 7,863,325 B2 | 1/2011 | Berkenstam | |
| 8,071,646 B2 | 12/2011 | Feuerstein | |
| 8,076,282 B2 | 12/2011 | Hageman | |
| 2002/0068100 A1 | 6/2002 | Kapoor | |
| 2002/0183389 A1 | 12/2002 | Peet | |
| 2002/0198177 A1 | 12/2002 | Horrobin | |
| 2003/0199481 A1 | 10/2003 | Garavani | |
| 2004/0044028 A1 | 3/2004 | Obukowicz | |
| 2004/0077723 A1 | 4/2004 | Granata | |
| 2004/0092590 A1 | 5/2004 | Arterburn | |
| 2004/0137253 A1 | 7/2004 | Tanioka | |
| 2004/0162348 A1 | 8/2004 | Peet | |
| 2004/0234587 A1 | 11/2004 | Sampalis | |
| 2004/0235948 A1 | 11/2004 | Oelze | |
| 2005/0267212 A1 | 12/2005 | Stoll | |
| 2006/0014676 A1 | 1/2006 | Sharma | |
| 2006/0034815 A1 | 2/2006 | Guzman | |
| 2006/0051406 A1 | 3/2006 | Parmar | |
| 2006/0083783 A1 | 4/2006 | Doyle | |
| 2006/0084696 A1 | 4/2006 | Grainger | |
| 2006/0188529 A1 | 8/2006 | Bobotas | |
| 2006/0211749 A1 | 9/2006 | Bobotas | |
| 2006/0211762 A1* | 9/2006 | Rongen et al. | 514/423 |
| 2006/0216361 A1 | 9/2006 | Edwards | |
| 2006/0217386 A1 | 9/2006 | Edwards | |
| 2006/0222701 A1 | 10/2006 | Kulkarni | |
| 2006/0228403 A1 | 10/2006 | Zimmerman | |
| 2006/0275218 A1 | 12/2006 | Tamarkin | |
| 2006/0287256 A1 | 12/2006 | Raederstorff | |
| 2007/0032546 A1 | 2/2007 | Almarsson | |
| 2007/0032548 A1 | 2/2007 | Ellis | |
| 2007/0036862 A1 | 2/2007 | Rongen | |
| 2007/0088170 A1 | 4/2007 | Bryhn | |
| 2007/0093553 A1 | 4/2007 | Baxter | |
| 2007/0104779 A1 | 5/2007 | Rongen | |
| 2007/0118916 A1 | 5/2007 | Puzio | |
| 2007/0141138 A1 | 6/2007 | Feurstein | |
| 2007/0166413 A1 | 7/2007 | Haber | |
| 2007/0191467 A1 | 8/2007 | Rongen | |
| 2007/0196465 A1 | 8/2007 | Bobotas | |
| 2007/0219271 A1 | 9/2007 | Mittmann | |
| 2007/0269507 A1 | 11/2007 | Sachetto | |
| 2008/0076823 A1 | 3/2008 | Watkins | |
| 2008/0085911 A1 | 4/2008 | Rongen | |
| 2008/0292649 A1 | 11/2008 | Hageman | |
| 2008/0306087 A1 | 12/2008 | Empfield | |
| 2009/0005323 A1 | 1/2009 | Percival | |
| 2009/0005327 A1 | 1/2009 | Granata | |
| 2009/0012167 A1 | 1/2009 | Rongen | |
| 2009/0018125 A1 | 1/2009 | Mittmann | |
| 2009/0018193 A1 | 1/2009 | Pamparana | |
| 2009/0042979 A1 | 2/2009 | Guzman | |
| 2009/0149533 A1 | 6/2009 | Almarsson | |
| 2009/0197795 A1 | 8/2009 | Smith | |
| 2009/0312345 A1 | 12/2009 | Fan | |
| 2010/0010026 A1* | 1/2010 | Rongen et al. | 514/275 |
| 2010/0062107 A1 | 3/2010 | Yoon | |
| 2010/0233254 A1 | 9/2010 | Miller | |
| 2010/0239660 A1 | 9/2010 | Doughman | |
| 2010/0311834 A1 | 12/2010 | Manku | |
| 2010/0331415 A1 | 12/2010 | Krumbholz | |
| 2011/0160161 A1* | 6/2011 | Sampalis et al. | 514/78 |
| 2011/0207821 A1 | 8/2011 | Framroze | |
| 2012/0093922 A1* | 4/2012 | Manku et al. | 424/451 |

FOREIGN PATENT DOCUMENTS

| | | |
|---|---|---|
| EP | 02248447 | 8/2010 |
| FR | 02862873 | 1/2003 |
| WO | 02083177 | 10/2002 |
| WO | 03086392 | 10/2003 |
| WO | 2004028470 | 4/2004 |
| WO | 2004047732 | 6/2004 |
| WO | 2006062748 | 6/2006 |
| WO | 2006011766 | 11/2006 |
| WO | 2006118988 | 11/2006 |
| WO | 2007011886 | 1/2007 |
| WO | 2007075841 | 7/2007 |
| WO | WO 2009140932 A2 * | 11/2009 |
| WO | 2010028067 | 3/2010 |
| WO | 2010103402 | 9/2010 |

OTHER PUBLICATIONS

Ruiz-Rodriguez, A. et al "Recent Trends in the advanced analysis of bioactive fatty acids"—Journal of Pharmaceutical and Biomedical Analysis, 51, (2010) 305-326.*

Gorlin, R. "The Biological Actions and Potential Clinical Significance of Dietary omega-3 Fatty Acids"—Arch Intern Med—vol. 148, Sep. 1988. p. 2043.*

Harris, William S., Current opinion in Lipidology (2012), 23 (1), p. 30-34.*

Kromhout, D., et al., Fish oil and omega-3 fatty acids in cardiovascular disease: do they really work? European heart journal, 2012. 33(4): p. 436-43.

Kurisu, S., et al., Effects of lipid-lowering therapy with strong statin on serum polyunsaturated fatty acid levels in patients with coronary artery disease. Heart and vessels, 2013. 28(1): p. 34-8.

Kurlandsky, L.E., et al., The absorption and effect of dietary supplementation with omega-3 fatty acids on serum leukotriene B4 in patients with cystic fibrosis. Pediatric pulmonology, 1994. 18(4): p. 211-7.

Kuro-o, M., Klotho. Pflugers Archiv : European journal of physiology, 2010. 459(2): p. 333-43.

Kwak, S.M., et al., Efficacy of omega-3 fatty acid supplements (eicosapentaenoic acid and docosahexaenoic acid) in the secondary prevention of cardiovascular disease: a meta-analysis of randomized, double-blind, placebo-controlled trials. Archives of internal medicine, 2012. 172(9): p. 686-94.

Lafourcade, M., et al., Nutritional omega-3 deficiency abolishes endocannabinoid-mediated neuronal functions. Nature neuroscience, 2011. 14(3): p. 345-50.

(56) References Cited

OTHER PUBLICATIONS

Lakhan, S.E. and K.F. Vieira, Nutritional therapies for mental disorders. Nutrition journal, 2008. 7: p. 2.
Lamotte, M., et al., A multi-country health economic evaluation of highly concentrated N-3 polyunsaturated fatty acids in secondary prevention after myocardial infarction. PharmacoEconomics, 2006. 24(8): p. 783-95.
Last, A.R., J.D. Ference, and J. Falleroni, Pharmacologic treatment of hyperlipidemia. American family physician, 2011. 84(5): p. 551-8.
Lawson, L.D. and B.G. Hughes, Human absorption of fish oil fatty acids as triacylglycerols, free acids, or ethyl esters. Biochemical and biophysical research communications, 1988. 152(1): p. 328-35.
Lawson, L.D. and B.G. Hughes, Absorption of eicosapentaenoic acid and docosahexaenoic acid from fish oil triacylglycerols or fish oil ethyl esters co-ingested with a high-fat meal. Biochemical and biophysical research communications, 1988. 156(2): p. 960-3.
Leaf, A., Plasma nonesterified fatty acid concentration as a risk factor for sudden cardiac death: the Paris Prospective Study. Circulation, 2001. 104(7): p. 744-5.
Leaf, A., et al., Prevention of fatal arrhythmias in high-risk subjects by fish oil n-3 fatty acid intake. Circulation, 2005. 112(18): p. 2762-8.
Leaf, A., et al., Clinical prevention of sudden cardiac death by n-3 polyunsaturated fatty acids and mechanism of prevention of arrhythmias by n-3 fish oils. Circulation, 2003. 107(21): p. 2646-52.
Leaf, A., et al., Membrane effects of the n-3 fish oil fatty acids, which prevent fatal ventricular arrhythmias. The Journal of membrane biology, 2005. 206(2): p. 129-39.
Lecarpentier, Y., V. Claes, and J.L. Hebert, PPARs, Cardiovascular Metabolism, and Function: Near- or Far-from-Equilibrium Pathways. PPAR research, 2010. 2010.
Lee, J.H., et al., Omega-3 fatty acids for cardioprotection. Mayo Clinic proceedings. Mayo Clinic, 2008. 83(3): p. 324-32.
Lee, S., et al., Current clinical applications of omega-6 and omega-3 fatty acids. Nutrition in clinical practice : official publication of the American Society for Parenteral and Enteral Nutrition, 2006. 21(4): p. 323-41.
Lesperance, F., et al., The efficacy of omega-3 supplementation for major depression: a randomized controlled trial. The Journal of clinical psychiatry, 2011. 72(8): p. 1054-62.
Lesperance, F., et al., The association between major depression and levels of soluble intercellular adhesion molecule 1, interleukin-6, and C-reactive protein in patients with recent acute coronary syndromes. The American journal of psychiatry, 2004. 161(2): p. 271-7.
Lewis, M.D. and J. Bailes, Neuroprotection for the warrior: dietary supplementation with omega-3 fatty acids. Military medicine, 2011. 176(10): p. 1120-7.
Lewis, M.D., et al., Suicide deaths of active-duty US military and omega-3 fatty-acid status: a case-control comparison. The Journal of clinical psychiatry, 2011. 72(12): p. 1585-90.
Li, M.F. and B.M. Cheung, Rise and fall of anti-obesity drugs. World journal of diabetes, 2011. 2(2): p. 19-23.
Li, X. et al., Docosahexanoic acid-induced coronary arterial dilation: actions of 17S-hydroxy docosahexaenoic acid on K + channel activity. The Journal of pharmacology and experimental therapeutics, 2011. 336(3): p. 891-9.
Li, X.D., et al., Tongxinluo reduces myocardial no-reflow and ischemia-reperfusion injury by stimulating the phosphorylation of eNOS via the PKA pathway. American journal of physiology. Heart and circulatory physiology, 2010. 299(4): p. H1255-61.
Li, Z. and D. Heber, Overeating and overweight: extra calories increase fat mass while protein increases lean mass. JAMA : the journal of the American Medical Association, 2012. 307(1): p. 86-7.
Libby, P., Inflammation and cardiovascular disease mechanisms. The American journal of clinical nutrition, 2006. 83(2): p. 456S-460S.
Lichtenstein, A.H., et al., Summary of American Heart Association Diet and Lifestyle Recommendations revision 2006. Arteriosclerosis, thrombosis, and vascular biology, 2006. 26(10): p. 2186-91.
Liew, R., Electrocardiogram-based predictors of sudden cardiac death in patients with coronary artery disease. Clinical cardiology, 2011. 34(8): p. 466-73.
Lin, P.Y. et al., Are omega-3 fatty acids antidepressants or just mood-improving agents? The effect depends upon diagnosis, supplement preparation, and severity of depression. Molecular psychiatry, 2012. 17(12): p. 1161-3.
Logan, A.C., Omega-3 fatty acids and major depression: a primer for the mental health professional. Lipids in health and disease, 2004. 3: p. 25.
London, B., et al., Omega-3 fatty acids and cardiac arrhythmias: prior studies and recommendations for future research: a report from the National Heart, Lung, and Blood Institute and Office of Dietary Supplements Omega-3 Fatty Acids and their Role in Cardiac Arrhythmogenesis Workshop. Circulation, 2007. 116(10): p. e320-35.
Lopez-Garcia, E., et al., Consumption of (n-3) fatty acids is related to plasma biomarkers of inflammation and endothelial activation in women. The Journal of nutrition, 2004. 134(7): p. 1806-11.
Lovegrove, J.A., et al., Moderate fish-oil supplementation reverses low-platelet, long-chain n-3 polyunsaturated fatty acid status and reduces plasma triacylglycerol concentrations in British Indo-Asians. The American journal of clinical nutrition, 2004. 79(6): p. 974-82.
Lungershausen, Y.K., et al., Reduction of blood pressure and plasma triglycerides by omega-3 fatty acids in treated hypertensives. Journal of hypertension, 1994. 12(9): p. 1041-5.
Madden, J., et al., Polymorphisms in the CD36 gene modulate the ability of fish oil supplements to lower fasting plasma triacyl glycerol and raise HDL cholesterol concentrations in healthy middle-aged men. Prostaglandins, leukotrienes, and essential fatty acids, 2008. 78(6): p. 327-35.
Madden, J., et al., the impact of common gene variants on the response of biomarkers of cardiovascular disease (CVD) risk to increased fish oil fatty acids intakes. Annual review of nutrition, 2011. 31: p. 203-34.
Mahdavi, H., et al., Dyslipidemia and cardiovascular diseases. Current opinion in lipidology, 2009. 20(2): p. 157-8.
Malinowski, J.M. and K. Metka, Elevation of low-density lipoprotein cholesterol concentration with over-the-counter fish oil supplementation. The Annals of pharmacotherapy, 2007. 41(7): p. 1296-300.
Marangoni, F., C. Colombo, and C. Galli, A method for the direct evaluation of the fatty acid status in a drop of blood from a fingertip in humans: applicability to nutritional and epidemiological studies. Analytical biochemistry, 2004. 326 (2): p. 267-72.
Marchioli, R., et al., Assessment of absolute risk of death after myocardial infarction by use of multiple-risk-factor assessment equations: GISSI-Prevenzione mortality risk chart. European heart journal, 2001. 22(22): p. 2085-103.
Marchioli, R., et al., Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. Circulation, 2002. 105(16): p. 1897-903.
Martin, C.M., Omega-3 fatty acids: proven benefit or just a "fish story"? The Consultant pharmacist : the journal of the American Society of Consultant Pharmacists, 2008. 23(3): p. 210-2, 214, 217-21.
Martin, L.J., et al., Chronic administration of the L-type calcium channel blocker nimodipine can facilitate the acquisition of sequence learning in a radial-arm maze. Behavioural pharmacology, 2004. 15(2): p. 133-9.
Martin, W., The beriberi analogy to myocardial infarction. Medical hypotheses, 1983. 10(2): p. 185-98.
Martins, J.G., H. Bentsen, and B.K. Puri, Eicosapentaenoic acid appears to be the key omega-3 fatty acid component associated with efficacy in major depressive disorder: a critique of Bloch and Hannestad and updated meta-analysis. Molecular psychiatry, 2012. 17(12): p. 1144-9.
Masi, L.N., et al., Toxicity of fatty acids on ECV-304 endothelial cells. Toxicology in vitro : an international journal published in association with BIBRA, 2011. 25(8): p. 2140-6.
Matsuoka, Y., Clearance of fear memory from the hippocampus through neurogenesis by omega-3 fatty acids: a novel preventive strategy for posttraumatic stress disorder? BioPsychoSocial medicine, 2011. 5: p. 3.

(56) References Cited

OTHER PUBLICATIONS

Matsuyama, W., et al., Effects of omega-3 polyunsaturated fatty acids on inflammatory markers in COPD. Chest, 2005. 128(6): p. 3817-27.
de Battle, J., et al., Association between Omega3 and Omega6 fatty acid intakes and serum inflammatory markers in COPD. The Journal of nutritional biochemistry, 2012. 23(7): p. 817-21.
Den Ruijter, H.M., et al., Pro- and antiarrhythmic properties of a diet rich in fish oil. Cardiovascular research, 2007. 73 (2): p. 316-25.
Dimmeler, S., et al., Suppression of apoptosis by nitric oxide via inhibition of interleukin-1beta-converting enzyme (ICE)-like and cysteine protease protein (CPP)-32-like proteases. The Journal of experimental medicine, 1997. 185(4): p. 601-7.
McCabe, T.J., et al., Enhanced electron flux and reduced calmodulin dissociation may explain "calcium-independent" eNOS activation by phosphorylation. The Journal of biological chemistry, 2000. 275(9): p. 6123-8.
McKenney, J.M. and D. Sica, Role of prescription omega-3 fatty acids in the treatment of hypertriglyceridemia. Pharmacotherapy, 2007. 27(5): p. 715-28.
McLennan, P., et al., The cardiovascular protective role of docosahexaenoic acid. European journal of pharmacology, 1996. 300(1-2): p. 83-9.
McLennan, P.L., Myocardial membrane fatty acids and the antiarrhythmic actions of dietary fish oil in animal models. Lipids, 2001. 36 Suppl: p. S111-4.
McLennan, P.L., et al., Myocardial function, ischaemia and n-3 polyunsaturated fatty acids: a membrane basis. Journal of cardiovascular medicine, 2007. 8 Suppl 1: p. S15-8.
McPherson, R., et al., Canadian Cardiovascular Society position statement—recommendations for the diagnosis and treatment of dyslipidemia and prevention of cardiovascular disease. The Canadian journal of cardiology, 2006. 22(11): p. 913-27.
Mensink, R.P., Dietary Fatty acids and cardiovascular health—an ongoing controversy. Annals of nutrition & metabolism, 2011. 58(1): p. 66-7.
Metz, J.A., et al., Dietary compliance and cardiovascular risk reduction with a prepared meal plan compared with a self-selected diet. The American journal of clinical nutrition, 1997. 66(2): p. 373-85.
Micallef, M.A. and M.L. Garg, Anti-inflammatory and cardioprotective effects of n-3 polyunsaturated fatty acids and plant sterols in hyperlipidemic individuals. Atherosclerosis, 2009. 204(2): p. 476-82.
Michel, J.B., et al., Reciprocal regulation of endothelial nitric-oxide synthase by Ca2+-calmodulin and caveolin. The Journal of biological chemistry, 1997. 272(25): p. 15583-6.
Michel, T. and O. Feron, Nitric oxide synthases: which, where, how, and why? The Journal of clinical investigation, 1997. 100(9): p. 2146-52.
Miljanovic, B., et al., Relation between dietary n-3 and n-6 fatty acids and clinically diagnosed dry eye syndrome in women. The American journal of clinical nutrition, 2005. 82(4): p. 887-93.
Miller, a.W., et al., Arachidonic acid-induced vasodilation of rat small mesenteric arteries is lipoxygenase-dependent. The Journal of pharmacology and experimental therapeutics, 2003. 304(1): p. 139-44.
Miller, M., et al., Triglycerides and cardiovascular disease: a scientific statement from the American Heart Association. Circulation, 2011. 123(20): p. 2292-333.
Min, Y., et al., Effect of storage temperature and length on fatty acid composition of fingertip blood collected on filter paper. Prostaglandins, leukotrienes, and essential fatty acids, 2011. 84(1-2): p. 13-8.
Mindrescu, C., et al., Omega-3 fatty acids plus rosuvastatin improves endothelial function in South Asians with dyslipidemia. Vascular health and risk management, 2008. 4(6): p. 1439-47.
Mohammadi, E., et al., Effects of omega-3 fatty acids supplementation on serum adiponectin levels and some metabolic risk factors in women with polycystic ovary syndrome. Asia Pacific journal of clinical nutrition, 2012.21(4): p. 511-8.

Morgan, N.G., Fatty acids and beta-cell toxicity. Current opinion in clinical nutrition and metabolic care, 2009. 12(2): p. 117-22.
Mori, T.A., et al., Docosahexaenoic acid but not eicosapentaenoic acid lowers ambulatory blood pressure and heart rate in humans. Hypertension, 1999. 34(2): p. 253-60.
Mori, T.A. and L.J. Beilin, Omega-3 fatty acids and inflammation. Current atherosclerosis reports, 2004. 6(6): p. 461-7.
Mori, T.A., et al., Purified eicosapentaenoic and docosahexaenoic acids have differential effects on serum lipids and lipoproteins, LDL particle size, glucose, and insulin in mildly hyperlipidemic men. The American journal of clinical nutrition, 2000. 71(5): p. 1085-94.
Mori, T.A. and R.J. Woodman, The independent effects of eicosapentaenoic acid and docosahexaenoic acid on cardiovascular risk factors in humans. Current opinion in clinical nutrition and metabolic care, 2006. 9(2): p. 95-104.
Moya, J., et al., Estimates of fish consumption rates for consumers of bought and self-caught fish in Connecticut, Florida, Minnesota, and North Dakota. The Science of the total environment, 2008. 403(1-3): p. 89-98.
Mozaffarian, D., Fish and n-3 fatty acids for the prevention of fatal coronary heart disease and sudden cardiac death. The American journal of clinical nutrition, 2008. 87(6): p. 1991S-6S.
Mozaffarian, D. et al., Effect of fish oil on heart rate in humans: a meta-analysis of randomized controlled trials. Circulation, 2005. 112(13): p. 1945-52.
Mozaffarian, D., et al., Circulating long-chain omega-3 fatty acids and incidence of congestive heart failure in older adults: the cardiovascular health study: a cohort study. Annals of internal medicine, 2011. 155(3): p. 160-70.
Mozaffarian, D., et al., The omega-3 Fatty Acids for Prevention of Post-Operative Atrial Fibrillation trial—rationale and design. American heart journal, 2011. 162(1): p. 56-63 e3.
Mozaffarian, D. and E.B. Rimm, Fish intake, contaminants, and human health: evaluating the risks and the benefits. JAMA : the journal of the American Medical Association, 2006. 296(15): p. 1885-99.
Musa-Veloso, K., et al., Long-chain omega-3 fatty acids eicosapentaenoic acid and docosahexaenoic acid dose-dependently reduce fasting serum triglycerides. Nutrition reviews, 2010. 68(3): p. 155-67.
Nabel, E.G., et al., Dilation of normal and constriction of atherosclerotic coronary arteries caused by the cold pressor test. Circulation, 1988. 77(1): p. 43-52.
Naghavi, M., et al., From vulnerable plaque to vulnerable patient: a call for new definitions and risk assessment strategies: Part I. Circulation, 2003. 108(14): p. 1664-72.
Naghavi, M., et al., From vulnerable plaque to vulnerable patient: a call for new definitions and risk assessment strategies: Part II. Circulation, 2003. 108(15): p. 1772-8.
Nair, G.M. and S.J. Connolly, Should patients with cardiovascular disease take fish oil? CMAJ : Canadian Medical Association journal = journal de l'Association medicale canadienne, 2008. 178(2): p. 181-2.
Ndiaye, M., et al., Red wine polyphenol-induced, endothelium-dependent NO-mediated relaxation is due to the redox-sensitive PI3-kinase/Akt-dependent phosphorylation of endothelial NO-synthase in the isolated porcine coronary artery. FASEB journal : official publication of the Federation of American Societies for Experimental Biology, 2005. 19(3): p. 455-7.
Nestel, P., et al., The n-3 fatty acids eicosapentaenoic acid and docosahexaenoic acid increase systemic arterial compliance in humans. The American journal of clinical nutrition, 2002. 76(2): p. 326-30.
Nilsson, A., et al., Effects of supplementation with n-3 polyunsaturated fatty acids on cognitive performance and cardiometabolic risk markers in healthy 51 to 72 years old subjects: a randomized controlled cross-over study. Nutrition journal, 2012. 11(1): p. 99.
Ninio, D.M., et al., Dietary fish oil protects against stretch-induced vulnerability to atrial fibrillation in a rabbit model. Journal of cardiovascular electrophysiology, 2005. 16(11): p. 1189-94.
Nodari, S., et al., n-3 polyunsaturated fatty acids in the prevention of atrial fibrillation recurrences after electrical cardioversion: a prospective, randomized study. Circulation, 2011. 124(10): p. 1100-6.

(56) References Cited

OTHER PUBLICATIONS

Nordestgaard, B.G., et al., Nonfasting triglycerides and risk of myocardial infarction, ischemic heart disease, and death in men and women. JAMA : the journal of the American Medical Association, 2007. 298(3): p. 299-308.

Nordoy, A., et al., Effects of atorvastatin and omega-3 fatty acids on LDL subfractions and postprandial hyperlipemia in patients with combined hyperlipemia. Nutrition, metabolism, and cardiovascular diseases : NMCD, 2001. 11(1): p. 7-16.

Nuernberg, K., et al., Metabolic responses to high-fat diets rich in n-3 or n-6 long-chain polyunsaturated fatty acids in mice selected for either high body weight or leanness explain different health outcomes. Nutrition & metabolism, 2011. 8(1): p. 56.

O'Keefe, J.H., Jr. and W.S. Harris, From Inuit to implementation: omega-3 fatty acids come of age. Mayo Clinic proceedings. Mayo Clinic, 2000. 75(6): p. 607-14.

O'Keefe, J.H. and W.S. Harris, Omega-3 fatty acids: time for clinical implementation? The American journal of cardiology, 2000. 85(10): p. 1239-41.

O'Sullivan, T.A., et al., Omega-3 Index correlates with healthier food consumption in adolescents and with reduced cardiovascular disease risk factors in adolescent boys. Lipids, 2011. 46(1): p. 59-67.

Oemar, B.S., et al., Reduced endothelial nitric oxide synthase expression and production in human atherosclerosis. Circulation, 1998. 97(25): p. 2494-8.

Ogden, C.L., et al., Prevalence of obesity in the United States, 2009-2010. NCHS data brief, 2012(82): p. 1-8.

Oh, D.Y. and J.M. Olefsky, Omega 3 fatty acids and GPR120. Cell metabolism, 2012. 15(5): p. 564-5.

Oh, D.Y., et al., GPR120 is an omega-3 fatty acid receptor mediating potent anti-inflammatory and insulin-sensitizing effects. Cell, 2010. 142(5): p. 687-98.

Ohara, K., The n-3 polyunsaturated fatty acid/dopamine hypothesis of schizophrenia. Progress in neuro-psychopharmacology & biological psychiatry, 2007. 31(2): p. 469-74.

Okuda, Y., et al., Eicosapentaenoic acid enhances nitric oxide production by cultured human endothelial cells. Biochemical and biophysical research communications, 1997. 232(2): p. 487-91.

Holub, B.J., Fish oils and cardiovascular disease. CMAJ : Canadian Medical Association journal = journal de l'Association medicale canadienne, 1989. 141(10): p. 1063.

Holub, B.J., Clinical nutrition: 4. Omega-3 fatty acids in cardiovascular care. CMAJ : Canadian Medical Association journal journal = journal de l'Association medicale canadienne, 2002. 166(5): p. 608-15.

Holub, B.J., et al., Correlation of omega-3 levels in serum phospholipid from 2053 human blood samples with key fatty acid ratios. Nutrition journal, 2009. 8: p. 58.

Hong, H., et al., Effects of simvastain combined with omega-3 fatty acids on high sensitive C-reactive protein, lipidemia, and fibrinolysis in patients with mixed dyslipidemia. Chinese medical sciences journal = Chung-kuo i hsueh k'o hsueh tsa chih / Chinese Academy of Medical Sciences, 2004. 19(2): p. 145-9.

Horrobin, D.F., et al., The effects of evening primrose oil, safflower oil and paraffin on plasma fatty acid levels in humans: choice of an appropriate placebo for clinical studies on primrose oil. Prostaglandins, leukotrienes, and essential fatty acids, 1991. 42(4): p. 245-9.

Hotamisligil, G.S., Inflammation and metabolic disorders. Nature, 2006. 444(7121): p. 860-7.

Houston, M.C., et al., Nonpharmacologic treatment of dyslipidemia. Progress in cardiovascular diseases, 2009. 52(2): p. 61-94.

Hsia, J., et al., Resting heart rate as a low tech predictor of coronary events in women: prospective cohort study. BMJ, 2009. 338: p. b219.

Hsia, J., et al., Compliance with National Cholesterol Education Program dietary and lifestyle guidelines among older women with self-reported hypercholesterolemia. The Women's Health Initiative. The American journal of medicine, 2002. 113(5): p. 384-92.

Hu, F.B., et al. Fish and long-chain omega-3 fatty acid intake and risk of coronary heart disease and total mortality in diabetic women. Circulation, 2003. 107(14): p. 1852-7.

Hu, F.B. and J.E. Manson, Omega-3 fatty acids and secondary prevention of cardiovascular disease—is it just a fish tale?: comment on "Efficacy of omega-3 fatty acid supplements (eicosapentaenoic acid and docosahexaenoic acid) in the secondary prevention of cardiovascular disease". Archives of internal medicine, 2012. 172(9): p. 694-6.

Huffman, J.C., et al., Case records of the Massachusetts General Hospital. Case 14-2008. A 78-year-old man with anergia and anhedonia associated with cardiovascular surgery. The New England journal of medicine, 2008. 358(19): p. 2051-9.

Huwiler, A. and J. Pfeilschifter, Lipids as targets for novel anti-inflammatory therapies. Pharmacology & therapeutics, 2009. 124(1): p. 96-112.

Jackson, M.A., et al., Efficacy of a new prescription-only medical food supplement in alleviating signs and symptoms of dry eye, with or without concomitant cyclosporine A. Clinical ophthalmology, 2011. 5: p. 1201-6.

Jacobson, T.A., Secondary prevention of coronary artery disease with omega-3 fatty acids. The American journal of cardiology, 2006. 98(4A): p. 611-701.

Jacobson, T.A., Beyond lipids: the role of omega-3 fatty acids from fish oil in the prevention of coronary heart disease. Current atherosclerosis reports, 2007. 9(2): p. 145-53.

James, A.T. and J.E. Lovelock, Essential fatty acids and human disease. British medical bulletin, 1958. 14(3): p. 262-6.

Jenkins, D.J., et al., Fish-oil supplementation in patients with implantable cardioverter defibrillators: a meta-analysis. CMAJ : Canadian Medical Association journal = journal de l'Association medicale canadienne, 2008. 178(2): p. 157-64.

Johnston, D.T., et al., Red blood cell omega-3 fatty acid levels and neurocognitive performance in deployed U.S. Servicemembers. Nutritional neuroscience, 2012.

Jouven, X. et al. Circulating nonesterified fatty acid level as a predictive risk factor for sudden death in the population. Circulation, 2001. 104(7): p. 756-61.

Ju, H., et al., Direct interaction of endothelial nitric-oxide synthase and caveolin-1 inhibits synthase activity. The Journal of biological chemistry, 1997. 272(30): p. 18522-5.

Jump, D.B., C.M. Depner, and S. Tripathy, Omega-3 fatty acid supplementation and cardiovascular disease: Thematic Review Series: New Lipid and Lipoprotein Targets for the Treatment of Cardiometabolic Diseases. Journal of lipid research, 2012. 53(12): p. 2525-45.

Kabagambe, E.K., et al., Erythrocyte fatty acid composition and the metabolic syndrome: a National Heart, Lung, and Blood Institute GOLDN study. Clinical chemistry, 2008. 54(1): p. 154-62.

Kahn, S.E, R.L. Hull, and K.M. Utzschneider, Mechanisms linking obesity to insulin resistance and type 2 diabetes. Nature, 2006. 444(7121): p. 840-6.

Kakar, R, T. Watson, and G.Y. Lip, New approaches to therapy with omega-3 fatty acids. Current atherosclerosis reports, 2008. 10(1): p. 79-87.

Kalogeropoulos, N., et al., Unsaturated fatty acids are inversely associated and n-6/n-3 ratios are positively related to inflammation and coagulation markers in plasma of apparently healthy adults. Clinica chimica acta; international journal of clinical chemistry, 2010. 411(7-8): p. 584-91.

Kanbay, M. et al., Sudden cardiac death in patients with chronic kidney disease: prevention is the sine qua non. Kidney & blood pressure research, 2011. 34(4): p. 269-76.

Kang, J.H., et al., Dietary capsaicin reduces obesity-induced insulin resistance and hepatic steatosis in obese mice fed a high-fat diet. Obesity, 2010. 18(4): p. 780-7.

Kar, S., Omacor and Omega-3 Fatty Acids for Treatment of Coronary Artery Disease and the Pleiotropic Effects. American journal of therapeutics, 2011.

Kastelein, J.J., et al., Rationale and design of dal-VESSEL: a study to assess the safety and efficacy of dalcetrapib on endothelial function using brachial artery flow-mediated vasodilatation. Current medical research and opinion, 2011. 27 (1): p. 141-50.

(56) References Cited

OTHER PUBLICATIONS

Katan, M.B., et al., Kinetics of the incorporation of dietary fatty acids into serum cholesteryl esters, erythrocyte membranes, and adipose tissue: an 18-month controlled study. Journal of lipid research, 1997. 38(10): p. 2012-22.

Kelley, D.S., et al., Docosahexaenoic acid supplementation decreases remnant-like particle-cholesterol and increases the (n-3) index in hypertriglyceridemic men. The Journal of nutrition, 2008. 138(1): p. 30-5.

Kelly, G., A review of the sirtuin system, its clinical implications, and the potential role of dietary activators like resveratrol: part 1. Alternative medicine review : a journal of clinical therapeutic, 2010. 15(3): p. 245-63.

Keys, A. and H. Sinclair, Real nutritional deficiency. British medical bulletin, 1952. 8(2-3): p. 262-4.

Kidd, P.M., Omega-3 DHA and EPA for cognition, behavior, and mood: clinical findings and structural-functional synergies with cell membrane phospholipids. Alternative medicine review : a journal of clinical therapeutic, 2007. 12(3): p. 207-27.

Kiecolt-Glaser, J.K., et al., Omega-3 supplementation lowers inflammation in healthy middle-aged and older adults: a randomized controlled trial. Brain, behavior, and immunity, 2012. 26(6): p. 988-95.

Kiecolt-Glaser, J.K., et al., Omega-3 fatty acids, oxidative stress, and leukocyte telomere length: A randomized controlled trial. Brain, behavior, and immunity, 2012.

Kim, H.H., et al., Eicosapentaenoic acid inhibits TNF-alpha-induced matrix metalloproteinase-9 expression in human keratinocytes, HaCaT cells. Biochemical and biophysical research communications, 2008. 368(2): p. 343-9.

Kinsella, J.E., B. Lokesh, and R.A. Stone, Dietary n-3 polyunsaturated fatty acids and amelioration of cardiovascular disease: possible mechanisms. The American journal of clinical nutrition, 1990. 52(1): p. 1-28.

Kondrup, J., et al., Nutritional risk screening (NRS 2002): a new method based on an analysis of controlled clinical trials. Clinical nutrition, 2003. 22(3): p. 321-36.

Konkel, A. and W.H. Schunck, Role of cytochrome P450 enzymes in the bioactivation of polyunsaturated fatty acids. Biochimica et biophysica acta, 2011. 1814(1): p. 210-22.

Korngold, E.C., et al., Amino-terminal pro-B-type natriuretic peptide and high-sensitivity C-reactive protein as predictors of sudden cardiac death among women. Circulation, 2009. 119(22): p. 2868-76.

Kowey, P.R., et al., Efficacy and safety of prescription omega-3 fatty acids for the prevention of recurrent symptomatic atrial fibrillation: a randomized controlled trial. JAMA : the journal of the American Medical Association, 2010. 304(21): p. 2363-72.

Krakowski, M.I. and P. Czobor, A prospective longitudinal study of cholesterol and aggression in patients randomized to clozapine, olanzapine, and haloperidol. Journal of clinical psychopharmacology, 2010. 30(2): p. 198-200.

Krey, J.F. and R.E. Dolmetsch, Molecular mechanisms of autism: a possible role for Ca2+ signaling. Current opinion in neurobiology, 2007. 17(1): p. 112-9.

Kris-Etherton, P.M., W.S. Harris, and L.J. Appel, Fish consumption, fish oil, omega-3 fatty acids, and cardiovascular disease. Circulation, 2002. 106(21): p. 2747-57.

Kris-Etherton, P.M., W.S. Harris, and L.J. Appel, Omega-3 fatty acids and cardiovascular disease: new recommendations from the American Heart Association. Arteriosclerosis, thrombosis, and vascular biology, 2003. 23(2): p. 151-2.

Kris-Etherton, P.M. and A.M. Hill, N-3 fatty acids: food or supplements? Journal of the American Dietetic Association, 2008. 108(7): p. 1125-30.

Kris-Etherton, P.M., et al., Polyunsaturated fatty acids in the food chain in the United States. The American journal of clinical nutrition, 2000. 71(1 Suppl): p. 179S-88S.

Kromhout, D., et al., The confusion about dietary fatty acids recommendations for CHD prevention. The British journal of nutrition, 2011. 106(5): p. 627-32.

Young, G.S., J.A. Conquer, and R. Thomas, Effect of randomized supplementation with high dose olive, flax or fish oil on serum phospholipid fatty acid levels in adults with attention deficit hyperactivity disorder. Reproduction, nutrition, development, 2005. 45(5): p. 549-58.

Yuan, G., K.Z. Al-Shali, and R.A. Hegele, Hypertriglyceridemia: its etiology, effects and treatment. CMAJ : Canadian Medical Association journal = journal de l'Association medicale canadienne, 2007. 176(8): p. 1113-20.

Yuan, J.M., et al., Fish and shellfish consumption in relation to death from myocardial infarction among men in Shanghai, China. American journal of epidemiology, 2001. 154(9): p. 809-16.

Yuen, A.W., et al., Erythrocyte and plasma fatty acid profiles in patients with epilepsy: does carbamazepine affect omega-3 fatty acid concentrations? Epilepsy & behavior : E&B, 2008. 12(2): p. 317-23.

Zampelas, A., Eicosapentaenoic acid (EPA) from highly concentrated n-3 fatty acid ethyl esters is incorporated into advanced atherosclerotic plaques and higher plaque EPA is associated with decreased plaque inflammation and increased stability. Atherosclerosis, 2010. 212(1): p. 34-5.

Zargar, A. and M.K. Ito, Long chain omega-3 dietary supplements: a review of the National Library of Medicine Herbal Supplement Database. Metabolic syndrome and related disorders, 2011. 9(4): p. 255-71.

Zeiher, A.M., et al., Coronary vasomotion in response to sympathetic stimulation in humans: importance of the functional integrity of the endothelium. Journal of the American College of Cardiology, 1989. 14(5): p. 1181-90.

Zhang, J., et al., Fish consumption and mortality from all causes, ischemic heart disease, and stroke: an ecological study. Preventive medicine, 1999. 28(5): p. 520-9.

Zhao, G., et al., Dietary alpha-linolenic acid inhibits proinflammatory cytokine production by peripheral blood mononuclear cells in hypercholesterolemic subjects. The American journal of clinical nutrition, 2007. 85(2): p. 385-91.

Zhao, G., et al., Waist circumference, abdominal obesity, and depression among overweight and obese U.S. adults: National Health and Nutrition Examination Survey 2005-2006. BMC psychiatry, 2011. 11: p. 130.

Zhuang, G., et al., A novel regulator of macrophage activation: miR-223 in obesity-associated adipose tissue inflammation. Circulation, 2012. 125(23): p. 2892-903.

Zock, P.L., J. Gerritsen, and M.B. Katan, Partial conservation of the sn-2 position of dietary triglycerides in fasting plasma lipids in humans. European journal of clinical investigation, 1996. 26(2): p. 141-50.

Zock, P.L., et al., Fatty acids in serum cholesteryl esters as quantitative biomarkers of dietary intake in humans. American journal of epidemiology, 1997. 145(12): p. 1114-22.

Saito, Y., et al., Effects of EPA on coronary artery disease in hypercholesterolemic patients with multiple risk factors: sub-analysis of primary prevention cases from the Japan EPA Lipid Intervention Study (JELIS). Atherosclerosis, 2008. 200(1): p. 135-40.

Saltiel, A.R., Fishing out a sensor for anti-inflammatory oils. Cell, 2010. 142(5): p. 672-4.

Samuel, S., et al., Estimating health and economic benefits from using prescription omega-3 fatty acids in patients with severe hypertriglyceridemia. The American journal of cardiology, 2011. 108(5): p. 691-7.

Sanchez-Villegas, A., et al., Long chain omega-3 fatty acids intake, fish consumption and mental disorders in the SUN cohort study. European journal of nutrition, 2007. 46(6): p. 337-46.

Sanders, T.A., et al., Effect of varying the ratio of n-6 to n-3 fatty acids by increasing the dietary intake of alpha-linolenic acid, eicosapentaenoic and docosahexaenoic acid, or both on fibrinogen and clotting factors VII and XII in persons aged 45-70 y: the OPTILIP study. The American journal of clinical nutrition, 2006. 84(3): p. 513-22.

Sangiovanni, J.P., et al., {omega}-3 Long-chain polyunsaturated fatty acid intake and 12-y incidence of neovascular age-related macular degeneration and central geographic atrophy: AREDS report

(56) References Cited

OTHER PUBLICATIONS 30, a prospective cohort study from the Age-Related Eye Disease Study. The American journal of clinical nutrition, 2009. 90(6): p. 1601-7.

Sarrazin, J.F., et al., Reduced incidence of vagally induced atrial fibrillation and expression levels of connexins by n-3 polyunsaturated fatty acids in dogs. Journal of the American College of Cardiology, 2007. 50(15): p. 1505-12.

Savelieva, I. and J. Camm, Statins and polyunsaturated fatty acids for treatment of atrial fibrillation. Nature clinical practice. Cardiovascular medicine, 2008. 5(1): p. 30-41.

Schachinger, V., M.B. Britten, and A.M. Zeiher, Prognostic impact of coronary vasodilator dysfunction on adverse long-term outcome of coronary heart disease. Circulation, 2000. 101(16): p. 1899-906.

Schmitz, G. and J. Ecker, The opposing effects of n-3 and n-6 fatty acids. Progress in lipid research, 2008. 47(2): p. 147-55.

Schuchardt, J.P., et al., Incorporation of EPA and DHA into plasma phospholipids in response to different omega-3 fatty acid formulations—a comparative bioavailability study of fish oil vs. krill oil. Lipids in health and disease, 2011. 10: p. 145.

Schumm, W.R., et al., Self-reported changes in subjective health and anthrax vaccination as reported by over 900 Persian Gulf War era veterans. Psychological reports, 2002. 90(2): p. 639-53.

Schwellenbach, L.J., et al., The triglyceride-lowering effects of a modest dose of docosahexaenoic acid alone versus in combination with low dose eicosapentaenoic acid in patients with coronary artery disease and elevated triglycerides. Journal of the American College of Nutrition, 2006. 25(6): p. 480-5.

Serafini, M., et al., Effect of acute ingestion of fresh and stored lettuce (Lactuca sativa) on plasma total antioxidant capacity and antioxidant levels in human subjects. The British journal of nutrition, 2002. 88(6): p. 615-23.

Shah, A.P., et al., Cardiovascular and endothelial effects of fish oil supplementation in healthy volunteers. Journal of cardiovascular pharmacology and therapeutics, 2007. 12(3): p. 213-9.

Shahar, E., et al., Docosahexaenoic acid and smoking-related chronic obstructive pulmonary disease. The Atherosclerosis Risk in Communities Study Investigators. American journal of respiratory and critical care medicine, 1999. 159(6): p. 1780-5.

Shenkman, B., et al., Testing of platelet deposition on polystyrene surface under flow conditions by the cone and plate (let) analyzer: role of platelet activation, fibrinogen and von Willebrand factor. Thrombosis research, 2000. 99(4): p. 353-61.

Shibata, R., N. Ouchi, and T. Murohara, Adiponectin and cardiovascular disease. Circulation journal : official journal of the Japanese Circulation Society, 2009. 73(4): p. 608-14.

Shimokawa, H., P. Kim, and P.M. Vanhoutte, Endothelium-dependent relaxation to aggregating platelets in isolated basilar arteries of control and hypercholesterolemic pigs. Circulation research, 1988. 63(3): p. 604-12.

Shimokawa, H., et al., Effects of dietary supplementation with cod-liver oil on endothelium-dependent responses in porcine coronary arteries. Circulation, 1987. 76(4): p. 898-905.

Shukla, P.C., et al., BRCA1 is an essential regulator of heart function and survival following myocardial infarction. Nature communications, 2011. 2: p. 593.

Siddiqui, R.A., et al., Docosahexaenoic acid: a natural powerful adjuvant that improves efficacy for anticancer treatment with no adverse effects. BioFactors, 2011. 37(6): p. 399-412.

Siddiqui, R.A., et al., Modulation of lipid rafts by Omega-3 fatty acids in inflammation and cancer: implications for use of lipids during nutrition support. Nutrition in clinical practice : official publication of the American Society for Parenteral and Enteral Nutrition, 2007. 22(1): p. 74-88.

Sierra, S., et al., Dietary eicosapentaenoic acid and docosahexaenoic acid equally incorporate as decosahexaenoic acid but differ in inflammatory effects. Nutrition, 2008. 24(3): p. 245-54.

Simopoulos, A.P., Omega-3 fatty acids in health and disease and in growth and development. The American journal of clinical nutrition, 1991. 54(3): p. 438-63.

Simopoulos, A.P., The importance of the ratio of omega-6/omega-3 essential fatty acids. Biomedicine & pharmacotherapy = Biomedecine & pharmacotherapie, 2002. 56(8): p. 365-79.

Simopoulos, A.P., Omega-3 fatty acids in inflammation and autoimmune diseases. Journal of the American College of Nutrition, 2002. 21(6): p. 495-505.

Simopoulos, A.P., The importance of the omega-6/omega-3 fatty acid ratio in cardiovascular disease and other chronic diseases. Experimental biology and medicine, 2008. 233(6): p. 674-88.

Singer, P. et al. Anti-inflammatory properties of omega-3 fatty acids in critical illness: novel mechanisms and an integrative perspective. Intensive care medicine, 2008. 34(9): p. 1580-92.

Siri-Tarino, P.W., Effects of diet on high-density lipoprotein cholesterol. Current atherosclerosis reports, 2011. 13(6): p. 453-60.

Siscovick, D.S., R.N. Lemaitre, and D. Mozaffarian, The fish story: a diet-heart hypothesis with clinical implications: n-3 polyunsaturated fatty acids, myocardial vulnerability, and sudden death. Circulation, 2003. 107(21): p. 2632-4.

Siscovick, D.S., et al., Dietary intake and cell membrane levels of long-chain n-3 polyunsaturated fatty acids and the risk of primary cardiac arrest. JAMA : the journal of the American Medical Association, 1995. 274(17): p. 1363-7.

Skulas-Ray, A.C., et al., Omega-3 fatty acid concentrates in the treatment of moderate hypertriglyceridemia. Expert opinion on pharmacotherapy, 2008. 9(7): p. 1237-48.

Smith, T.C., et al., New onset and persistent symptoms of post-traumatic stress disorder self reported after deployment and combat exposures: prospective population based US military cohort study. BMJ, 2008. 336(7640): p. 366-71.

Soczynska, J.K., et al., Mood disorders and obesity: understanding inflammation as a pathophysiological nexus. Neuromolecular medicine, 2011. 13(2): p. 93-116.

Soininen, P., et al., High-throughput serum NMR metabonomics for cost-effective holistic studies on systemic metabolism. The Analyst, 2009. 134(9): p. 1781-5.

Sontrop, J. and M.K. Campbell, Omega-3 polyunsaturated fatty acids and depression: a review of the evidence and a methodological critique. Preventive medicine, 2006. 42(1): p. 4-13.

Sorgi, P.J., et al., Effects of an open-label pilot study with high-dose EPA/DHA concentrates on plasma phospholipids and behavior in children with attention deficit hyperactivity disorder. Nutrition journal, 2007. 6: p. 16.

Sperry, W.M. and F.C. Brand, The determination of total lipides in blood serum. The Journal of biological chemistry, 1955. 213(1): p. 69-76.

Spieker, L.E., et al., C-reactive protein influences shear stress-dependent platelet adhesion in patients with familiar hypercholesterolemia and coronary artery disease undergoing LDL apheresis. Thrombosis and haemostasis, 2006. 96(4): p. 540-2.

Spieker, L.E., et al., Shear stress-dependent platelet function after LDL cholesterol apheresis. Thrombosis research, 2004. 113(6): p. 395-8.

Splawski, I., et al., Ca(V)1.2 calcium channel dysfunction causes a multisystem disorder including arrhythmia and autism. Cell, 2004. 119(1): p. 19-31.

Stark, K.D., The percentage of n-3 highly unsaturated fatty acids in total HUFA as a biomarker for omega-3 fatty acid status in tissues. Lipids, 2008. 43(1): p. 45-53.

Storlien, L.H., et al., Fish oil prevents insulin resistance induced by high-fat feeding in rats. Science, 1987. 237(4817): p. 885-8.

Su, K.P., et al., Omega-3 fatty acids in major depressive disorder. A preliminary double-blind, placebo-controlled trial. European neuropsychopharmacology : the journal of the European College of Neuropsychopharmacology, 2003. 13(4): p. 267-71.

Sublette, M.E., et al., Meta-analysis of the effects of eicosapentaenoic acid (EPA) in clinical trials in depression. The Journal of clinical psychiatry, 2011. 72(12): p. 1577-84.

Sublette, M.E., et al., Omega-3 polyunsaturated essential fatty acid status as a predictor of future suicide risk. The American journal of psychiatry, 2006. 163(6): p. 1100-2.

Sun, Q., et al., Blood concentrations of individual long-chain n-3 fatty acids and risk of nonfatal myocardial infarction. The American journal of clinical nutrition, 2008. 88(1): p. 216-23.

(56) References Cited

OTHER PUBLICATIONS

Surette, M.E., The science behind dietary omega-3 fatty acids. CMAJ : Canadian Medical Association journal = journal de l'Association medicale canadienne, 2008. 178(2): p. 177-80.
Suwaidi, J.A., et al., Long-term follow-up of patients with mild coronary artery disease and endothelial dysfunction. Circulation, 2000. 101(9): p. 948-54.
Swanson, D., R. Block, and S.A. Mousa, Omega-3 fatty acids EPA and DHA: health benefits throughout life. Advances in nutrition, 2012. 3(1): p. 1-7.
Tabak, C., et al., Fruit and fish consumption: a possible explanation for population differences in COPD mortality (The Seven Countries Study). European journal of clinical nutrition, 1998. 52(11): p. 819-25.
Tabak, C., et al., Diet and chronic obstructive pulmonary disease: independent beneficial effects of fruits, whole grains, and alcohol (the MORGEN study). Clinical and experimental allergy : journal of the British Society for Allergy and Clinical Immunology, 2001. 31(5): p. 747-55.
Tabak, C., et al., Dietary factors and pulmonary function: a cross sectional study in middle aged men from three European countries. Thorax, 1999. 54(11): p. 1021-6.
Tagawa, H., et al., Long-term treatment with eicosapentaenoic acid augments both nitric oxide-mediated and non-nitric oxide-mediated endothelium-dependent forearm vasodilatation in patients with coronary artery disease. Journal of cardiovascular pharmacology, 1999. 33(4): p. 633-40.
Taneja, A. and H. Singh, Challenges for the delivery of long-chain n-3 fatty acids in functional foods. Annual review of food science and technology, 2012. 3: p. 105-23.
Tannock, L.R., Advances in the management of hyperlipidemia-induced atherosclerosis. Expert review of cardiovascular therapy, 2008. 6(3): p. 369-83.
Tanskanen, A., et al., Fish consumption, depression, and suicidality in a general population. Archives of general psychiatry, 2001. 58(5): p. 512-3.
Taskinen, M.R., et al., Dual metabolic defects are required to produce hypertriglyceridemia in obese subjects. Arteriosclerosis, thrombosis, and vascular biology, 2011. 31(9): p. 2144-50.
Taziki, O., et al., The effect of low dose omega-3 on plasma lipids in hemodialysis patients. Saudi journal of kidney diseases and transplantation : an official publication of the Saudi Center for Organ Transplantation, Saudi Arabia, 2007. 18(4): p. 571-6.
Tenenbaum, A., et al., Optimal management of combined dyslipidemia: what have we behind statins monotherapy? Advances in cardiology, 2008. 45: p. 127-53.
Thies, F., et al., Association of n-3 polyunsaturated fatty acids with stability of atherosclerotic plaques: a randomised controlled trial. Lancet, 2003. 361(9356): p. 477-85.
Thies, F., et al., Dietary supplementation with eicosapentaenoic acid, but not with other long-chain n-3 or n-6 polyunsaturated fatty acids, decreases natural killer cell activity in healthy subjects aged >55 y. The American journal of clinical nutrition, 2001. 73(3): p. 539-48.
Tishinsky, J.M., D.W. Ma, and L.E. Robinson, Eicosapentaenoic acid and rosiglitazone increase adiponectin in an additive and PPARgamma-dependent manner in human adipocytes. Obesity, 2011. 19(2): p. 262-8.
Toda, N., Age-related changes in endothelial function and blood flow regulation. Pharmacology & therapeutics, 2012. 133(2): p. 159-76.
Toto, R.D., S.M. Grundy, and G.L. Vega, Pravastatin treatment of very low density, intermediate density and low density lipoproteins in hypercholesterolemia and combined hyperlipidemia secondary to the nephrotic syndrome. American journal of nephrology, 2000. 20(1): p. 12-7.
Trikalinos, T.A., et al., Effects of Eicosapentanoic Acid and Docosahexanoic Acid on Mortality Across Diverse Settings: Systematic Review and Meta-Analysis of Randomized Trials and Prospective Cohorts: Nutritional Research Series, vol. 4, 2012.

Tsao, P.S., et al., Fluid flow inhibits endothelial adhesiveness. Nitric oxide and transcriptional regulation of VCAM-1. Circulation, 1996. 94(7): p. 1682-9.
Van Gaal, L.F., I.L. Mertens, and C.E. De Block, Mechanisms linking obesity with cardiovascular disease. Nature, 2006. 444(7121): p. 875-80.
Vanhoutte, P.M., Endothelium and control of vascular function. State of the Art lecture. Hypertension, 1989. 13(6 Pt 2): p. 658-67.
Vedtofte, M.S., et al., Dietary alpha-linolenic acid, linoleic acid, and n-3 long-chain PUFA and risk of ischemic heart disease. The American journal of clinical nutrition, 2011. 94(4): p. 1097-103.
Verkerk, A.O., et al., Incorporated sarcolemmal fish oil fatty acids shorten pig ventricular action potentials. Cardiovascular research, 2006. 70(3): p. 509-20.
Villegas, R. et al., Fish, shellfish, and long-chain n-3 fatty acid consumption and risk of incident type 2 diabetes in middle-aged Chinese men and women. The American journal of clinical nutrition, 2011. 94(2): p. 543-51.
Villines, T.C., et al., Niacin: the evidence, clinical use, and future directions. Current atherosclerosis reports, 2012. 14(1): p. 49-59.
von Schacky, C., A review of omega-3 ethyl esters for cardiovascular prevention and treatment of increased blood triglyceride levels. Vascular health and risk management, 2006. 2(3): p. 251-62.
von Schacky, C., The Omega-3 Index as a risk factor for cardiovascular diseases. Prostaglandins & other lipid mediators, 2011. 96(1-4): p. 94-8.
von Schacky, C., Meta-analysing randomised controlled trials with omega-3 fatty acids in cardiovascular disease. Evidence-based medicine, 2012.
von Schacky, C. and W.S. Harris, Cardiovascular risk and the omega-3 index. Journal of cardiovascular medicine, 2007. 8 Suppl 1: p. S46-9.
Walda, I.C., et al., Diet and 20-year chronic obstructive pulmonary disease mortality in middle-aged men from three European countries. European journal of clinical nutrition, 2002. 56(7): p. 638-43.
Wall, R., et al., Fatty acids from fish: the anti-inflammatory potential of long-chain omega-3 fatty acids. Nutrition reviews, 2010. 68(5): p. 280-9.
Wang, C., et al., n-3 Fatty acids from fish or fish-oil supplements, but not alpha-linolenic acid, benefit cardiovascular disease outcomes in primary- and secondary-prevention studies: a systematic review. The American journal of clinical nutrition, 2006. 84(1): p. 5-17.
Wang, Q., et al., Effect of omega-3 fatty acids supplementation on endothelial function: a meta-analysis of randomized controlled trials. Atherosclerosis, 2012. 221(2): p. 536-43.
Ward, S., et al., A systematic review and economic evaluation of statins for the prevention of coronary events. Health technology assessment, 2007. 11(14): p. 1-160, iii-iv.
Wei, M.Y. and T.A. Jacobson, Effects of eicosapentaenoic acid versus docosahexaenoic acid on serum lipids: a systematic review and meta-analysis. Current atherosclerosis reports, 2011. 13(6): p. 474-83.
Weill, P., et al., Effects of introducing linseed in livestock diet on blood fatty acid composition of consumers of animal products. Annals of nutrition & metabolism, 2002. 46(5): p. 182-91.
Wennberg, M., et al., Fish intake, mercury, long-chain n-3 polyunsaturated fatty acids and risk of stroke in northern Sweden. The British journal of nutrition, 200T 98(5): p. 1038-45.
Werns, S.W., et al., Evidence of endothelial dysfunction in angiographically normal coronary arteries of patients with coronary artery disease. Circulation, 1989. 79(2): p. 287-91.
West, S.G., et al., Acute effects of monounsaturated fatty acids with and without omega-3 fatty acids on vascular reactivity in individuals with type 2 diabetes. Diabetologia, 2005. 48(1): p. 113-22.
Whang, W., et al., Depression and risk of sudden cardiac death and coronary heart disease in women: results from the Nurses' Health Study. Journal of the American College of Cardiology, 2009. 53(11): p. 950-8.
Wilhelm, M. et al., Red blood cell omega-3 fatty acids and the risk of ventricular arrhythmias in patients with heart failure. American heart journal, 2008. 155(6): p. 971-7.

(56) References Cited

OTHER PUBLICATIONS

Witt, P.M., et al., The incorporation of marine n-3 PUFA into platelets and adipose tissue in pre- and postmenopausal women: a randomised, double-blind, placebo-controlled trial. The British journal of nutrition, 2010. 104(3): p. 318-25.

Woodman, R.J., et al., Effects of purified eicosapentaenoic and docosahexaenoic acids on glycemic control, blood pressure, and serum lipids in type 2 diabetic patients with treated hypertension. The American journal of clinical nutrition, 2002. 76(5): p. 1007-15.

Wu, A., Z. Ying, and F. Gomez-Pinilla, Omega-3 fatty acids supplementation restores mechanisms that maintain brain homeostasis in traumatic brain injury. Journal of neurotrauma, 2007. 24(10): p. 1587-95.

Wu, J.H., et al., Association of plasma phospholipid long-chain omega-3 fatty acids with incident atrial fibrillation in older adults: the cardiovascular health study. Circulation, 2012. 125(9): p. 1084-93.

Wurtz, P., et al., Characterization of systemic metabolic phenotypes associated with subclinical atherosclerosis. Molecular bioSystems, 2011. 7(2): p. 385-93.

Xiao, Y.F., et al., Blocking effects of polyunsaturated fatty acids on Na+ channels of neonatal rat ventricular myocytes. Proceedings of the National Academy of Sciences of the United States of America, 1995. 92(24): p. 11000-4.

Xun, P., et al., Fish consumption and risk of stroke and its subtypes: accumulative evidence from a meta-analysis of prospective cohort studies. European journal of clinical nutrition, 2012. 66(11): p. 1199-207.

Yanagisawa, A. and A.M. Lefer, Vasoactive effects of eicosapentaenoic acid on isolated vascular smooth muscle. Basic research in cardiology, 1987. 82(2): p. 186-96.

Yasuda, S. and H. Shimokawa, Potential usefulness of fish oil in the primary prevention of acute coronary syndrome. European heart journal, 2010. 31(1): p. 15-6.

Yokoyama, M., et al., Effects of eicosapentaenoic acid on major coronary events in hypercholesterolaemic patients (Jelis): a randomised open-label, blinded endpoint analysis. Lancet, 2007. 369(9567): p. 1090-8.

Freeman, M.P., et al., Omega-3 fatty acids: evidence basis for treatment and future research in psychiatry. The Journal of clinical psychiatry, 2006. 67(12): p. 1954-67.

Friedman, A. and S. Moe, Review of the effects of omega-3 supplementation in dialysis patients. Clinical journal of the American Society of Nephrology : CJASN, 2006. 1(2): p. 182-92.

Friedman, A.N., Omega-3 fatty acid supplementation in advanced kidney disease. Seminars in dialysis, 2010. 23(4): p. 396-400.

Fulton, D., et al., Regulation of endothelium-derived nitric oxide production by the protein kinase Akt. Nature, 1999. 399(6736): p. 597-601.

Fung, M.A. and J.J. Frohlich, Common problems in the management of hypertriglyceridemia. CMAJ : Canadian Medical Association journal = journal de l'Association medicale canadienne, 2002. 167(11): p. 1261-6.

Gajos, G., et al., Reduced thrombin formation and altered fibrin clot properties induced by polyunsaturated omega-3 fatty acids on top of dual antiplatelet therapy in patients undergoing percutaneous coronary intervention (Omega-PCI clot). Arteriosclerosis, thrombosis, and vascular biology, 2011. 31(7): p. 1696-702.

Galan, P., et al., The SU.FOL.OM3 Study: a secondary prevention trial testing the impact of supplementation with folate and B-vitamins and/or Omega-3 PUFA on fatal and non fatal cardiovascular events, design, methods and participants characteristics. Trials, 2008. 9: p. 35.

Galan, P., et al., Effects of B vitamins and omega 3 fatty acids on cardiovascular diseases: a randomised placebo controlled trial. BMJ, 2010. 341: p. c6273.

Gallis, B., et al., Identification of flow-dependent endothelial nitric-oxide synthase phosphorylation sites by mass spectrometry and regulation of phosphorylation and nitric oxide production by the phosphatidylinositol 3-kinase inhibitor LY294002. The Journal of biological chemistry, 1999. 274(42): p. 30101-8.

Garcia-Cardena, G., et al., Dynamic activation of endothelial nitric oxide synthase by Hsp90. Nature, 1998. 392(6678): p. 821-4.

Gebauer, S.K., et al., n-3 fatty acid dietary recommendations and food sources to achieve essentiality and cardiovascular benefits. The American journal of clinical nutrition, 2006. 83(6 Suppl): p. 1526S-1535S.

Geleijnse, J.M., et al., Blood pressure response to fish oil supplementation: metaregression analysis of randomized trials. Journal of hypertension, 2002. 20(8): p. 1493-9.

Geleijnse, J.M., et al., Effect of low doses of n-3 fatty acids on cardiovascular diseases in 4,837 post-myocardial infarction patients: design and baseline characteristics of the Alpha Omega Trial. American heart journal, 2010. 159(4): p. 539-546 e2.

Germano, J.J., et al., Frequency and causes of implantable cardioverter-defibrillator therapies: is device therapy proarrhythmic? The American journal of cardiology, 2006. 97(8): p. 1255-61.

Gillies, P.J., W.S. Harris, and P.M. Kris-Etherton, Omega-3 fatty acids in food and pharma: the enabling role of biotechnology. Current atherosclerosis reports, 2011. 13(6): p. 467-73.

Glatz, J.F., A.E. Soffers, and M.B. Katan, Fatty acid composition of serum cholesteryl esters and erythrocyte membranes as indicators of linoleic acid intake in man. The American journal of clinical nutrition, 1989. 49(2): p. 269-76.

Gleason, J.A., et al., Cardiovascular risk reduction and dietary compliance with a home-delivered diet and lifestyle modification program. Journal of the American Dietetic Association, 2002. 102(10): p. 1445-51.

Golub, N., et al., Greasing the wheels of managing overweight and obesity with omega-3 fatty acids. Medical hypotheses, 2011. 77(6): p. 1114-20.

Gonzalez-Periz, A., et al., Obesity-induced insulin resistance and hepatic steatosis are alleviated by omega-3 fatty acids: a role for resolvins and protectins. FASEB journal : official publication of the Federation of American Societies for Experimental Biology, 2009. 23(6): p. 1946-57.

Greene, E.R., et al., Regulation of inflammation in cancer by eicosanoids. Prostaglandins & other lipid mediators, 2011. 96(1-4): p. 27-36.

Gregor, M.F. and G.S. Hotamisligil, Inflammatory mechanisms in obesity. Annual review of immunology, 2011. 29: p. 415-45.

Grimes, D.S., Are statins analogues of vitamin D? Lancet, 2006. 368(9529): p. 83-6.

Grimsgaard, S., et al., Highly purified eicosapentaenoic acid and docosahexaenoic acid in humans have similar triacylglycerol-lowering effects but divergent effects on serum fatty acids. The American journal of clinical nutrition, 1997. 66(3): p. 649-59.

Gronroos, N.N., et al., Fish, fish-derived n-3 fatty acids, and risk of incident atrial fibrillation in the Atherosclerosis Risk in Communities (ARIC) study. PloS one, 2012. 7(5): p. e36686.

Gylling, H. and T.A. Miettinen, A review of clinical trials in dietary interventions to decrease the incidence of coronary artery disease. Current controlled trials in cardiovascular medicine, 2001. 2(3): p. 123-128.

Haase, J., et al., In-vivo validation of on-line and off-line geometric coronary measurements using insertion of stenosis phantoms in porcine coronary arteries. Catheterization and cardiovascular diagnosis, 1992. 27(1): p. 16-27.

Hagve, T.A., O. Lie, and M. Gronn, The effect of dietary N-3 fatty acids on osmotic fragility and membrane fluidity of human erythrocytes. Scandinavian journal of clinical and laboratory investigation. Supplementum, 1993. 215: p. 75-84.

Hansson, G.K., Inflammation, atherosclerosis, and coronary artery disease. The New England journal of medicine, 2005. 352(16): p. 1685-95.

Harbaugh, M.P., et al., Long-chain, n-3 fatty acids and physical activity—Independent and interactive associations with cardiac autonomic control. International journal of cardiology, 2012.

Harper, C.R. and T.A. Jacobson, Usefulness of omega-3 fatty acids and the prevention of coronary heart disease. The American journal of cardiology, 2005. 96(11): p. 1521-9.

Harris, W.S., International recommendations for consumption of long-chain omega-3 fatty acids. Journal of cardiovascular medicine, 2007. 8 Suppl 1: p. S50-2.

(56) References Cited

OTHER PUBLICATIONS

Harris, W.S., Omega-3 fatty acids and cardiovascular disease: a case for omega-3 index as a new risk factor. Pharmacological research : the official journal of the Italian Pharmacological Society, 2007. 55(3): p. 217-23.
Harris, W.S., Are n-3 fatty acids still cardioprotective? Current opinion in clinical nutrition and metabolic care, 2012.
Harris, W.S., et al., Safety and efficacy of Omacor in severe hypertriglyceridemia. Journal of cardiovascular risk, 1997. 4(5-6): p. 385-91.
Harris, W.S. and D.M. Klurfeld, Twentieth-century trends in essential fatty acid intakes and the predicted omega-3 index: evidence versus estimates. The American journal of clinical nutrition, 2011. 93(5): p. 907-8.
Harris, W.S., et al., Omega-3 fatty acids and coronary heart disease risk: clinical and mechanistic perspectives. Atherosclerosis, 2008. 197(1): p. 12-24.
Harris, W.S., Y. Park, and W.L. Isley, Cardiovascular disease and long-chain omega-3 fatty acids. Current opinion in lipidology, 2003. 14(1): p. 9-14.
Harris, W.S., et al., Comparison of the effects of fish and fish-oil capsules on the n 3 fatty acid content of blood cells and plasma phospholipids. The American journal of clinical nutrition, 2007. 86(6): p. 1621-5.
Harris, W.S., et al., Changes in erythrocyte membrane trans and marine fatty acids between 1999 and 2006 in older Americans. The Journal of nutrition, 2012. 142(7): p. 1297-303.
Harris, W.S. and C. Von Schacky, The Omega-3 Index: a new risk factor for death from coronary heart disease? Preventive medicine, 2004. 39(1): p. 212-20.
Heidt, M.C., et al., Beneficial effects of intravenously administered N-3 fatty acids for the prevention of atrial fibrillation after coronary artery bypass surgery: a prospective randomized study. The Thoracic and cardiovascular surgeon, 2009. 57(5): p. 276-80.
Henderson, W.R., Jr., et al., Oral absorption of omega-3 fatty acids in patients with cystic fibrosis who have pancreatic insufficiency and in healthy control subjects. The Journal of pediatrics, 1994. 124(3): p. 400-8.
Henkin, Y., et al., Saturated fats, cholesterol, and dietary compliance. Archives of internal medicine, 1992. 152(6): p. 1167-74.
Hermann, C., A.M. Zeiher, and S. Dimmeler, Shear stress inhibits H2O2-induced apoptosis of human endothelial cells by modulation of the glutathione redox cycle and nitric oxide synthase. Arteriosclerosis, thrombosis, and vascular biology, 1997. 17(12): p. 3588-92.
Hessvik, N.P., et al., Metabolic switching of human myotubes is improved by n-3 fatty acids. Journal of lipid research, 2010. 51(8): p. 2090-104.
Hillis, G.S., et al., Effects of a brief course of azithromycin on soluble cell adhesion molecules and markers of inflammation in survivors of an acute coronary syndrome: A double-blind, randomized, placebo-controlled study. American heart journal, 2004. 148(1): p. 72-9.
Hirai, S., et al., Functional food targeting the regulation of obesity-induced inflammatory responses and pathologies. Mediators of inflammation, 2010. 2010: p. 367838.
Hollenberg, S.M., et al., Coronary endothelial dysfunction after heart transplantation predicts allograft vasculopathy and cardiac death. Circulation, 2001. 104(25): p. 3091-6.
Holloman, E.L. and M.C. Newman, Expanding perceptions of subsistence fish consumption: evidence of high commercial fish consumption and dietary mercury exposure in an urban coastal community. The Science of the total environment, 2012. 416: p. 111-20.
Holub, B.J., Dietary fish oils containing eicosapentaenoic acid and the prevention of atherosclerosis and thrombosis. CMAJ : Canadian Medical Association journal = journal de l'Association medicale canadienne, 1988. 139(5): p. 377-81.
Block, R.C., et al., The Effects of EPA+DHA and Aspirin on Inflammatory Cytokines and Angiogenesis Factors. World Journal of Cardiovascular Diseases, 2012. 2(1): p. 14-19.

Block, R.C., et al., EPA and DHA in blood cell membranes from acute coronary syndrome patients and controls. Atherosclerosis, 2008. 197(2): p. 821-8.
Blum, R., et al., Genotoxicity and subchronic toxicity studies of DHA-rich oil in rats. Regulatory toxicology and pharmacology : RTP, 2007. 49(3): p. 271-84.
Blum, R., et al., One-generation reproductive toxicity study of DHA-rich oil in rats. Regulatory toxicology and pharmacology : RTP, 2007. 49(3): p. 260-70.
Boo, Y.C., et al., Shear stress stimulates phosphorylation of eNOS at Ser(635) by a protein kinase A-dependent mechanism. American journal of physiology. Heart and circulatory physiology, 2002. 283(5): p. H1819-28.
Bosch, J., et al., n-3 fatty acids and cardiovascular outcomes in patients with dysglycemia. The New England journal of medicine, 2012. 367(4): p. 309-18.
Bourre, J.M., Dietary omega-3 fatty acids for women. Biomedicine & pharmacotherapy = Biomedecine & pharmacotherapie, 2007. 61(2-3): p. 105-12.
Boyd, R. B. Leigh, and P. Stuart, Capillary versus venous bedside blood glucose estimations. Emergency medicine journal : EMJ, 2005. 22(3): p. 177-9.
Brasky, T.M., et al., Serum phospholipid fatty acids and prostate cancer risk: results from the prostate cancer prevention trial. American journal of epidemiology, 2011. 173(12): p. 1429-39.
Bray, G.A., et al., Effect of dietary protein content on weight gain, energy expenditure, and body composition during overeating: a randomized controlled trial. JAMA : the journal of the American Medical Association, 2012. 307(1): p. 47-55.
Brevetti, G., et al., Increased inflammatory status and higher prevalence of three-vessel coronary artery disease in patients with concomitant coronary and peripheral atherosclerosis. Thrombosis and haemostasis, 2003. 89(6): p. 1058-63.
Bronte-Stewart, B., The effect of dietary fats on the blood lipids and their relation to ischaemic heart disease. British medical bulletin, 1958. 14(3): p. 243-52.
Brouwer, I.A., A. Geelen, and M.B. Katan, n-3 Fatty acids, cardiac arrhythmia and fatal coronary heart disease. Progress in lipid research, 2006. 45(4): p. 357-67.
Brouwer, I.A., et al., Effect of fish oil on ventricular tachyarrhythmia and death in patients with implantable cardioverter defibrillators: the Study on Omega-3 Fatty Acids and Ventricular Arrhythmia (SOFA) randomized trial. JAMA : the journal of the American Medical Association, 2006. 295(22): p. 2613-9.
Brouwer, I.A., et al., Rationale and design of a randomised controlled clinical trial on supplemental intake of n-3 fatty acids and incidence of cardiac arrhythmia: SOFA. European journal of clinical nutrition, 2003. 57(10): p. 1323-30.
Brown, W.M., Treating COPD with PDE 4 inhibitors. International journal of chronic obstructive pulmonary disease, 2007. 2(4): p. 517-33.
Bryhn, M., et al., The bioavailability and pharmacodynamics of different concentrations of omega-3 acid ethyl esters. Prostaglandins, leukotrienes, and essential fatty acids, 2006. 75(1): p. 19-24.
Buckley, J.D. and P.R. Howe, Long-chain omega-3 polyunsaturated fatty acids may be beneficial for reducing obesity—a review. Nutrients, 2010. 2(12): p. 1212-30.
Bunea, R., K. El Farrah, and L. Deutsch, Evaluation of the effects of Neptune Krill Oil on the clinical course of hyperlipidemia. Alternative medicine review : a journal of clinical therapeutic, 2004. 9(4): p. 420-8.
Burns, R.N. and N.H. Moniri, Agonism with the omega-3 fatty acids alpha-linolenic acid and docosahexaenoic acid mediates phosphorylation of both the short and long isoforms of the human GPR120 receptor. Biochemical and biophysical research communications, 2010. 396(4): p. 1030-5.
Burns, T., et al., Effect of omega-3 fatty acid supplementation on the arachidonic acid:eicosapentaenoic acid ratio. Pharmacotherapy, 2007. 27(5): p. 633-8.
Burr, M.L., Lessons from the story of n-3 fatty acids. The American journal of clinical nutrition, 2000. 71(1 Suppl): p. 397S-8S.
Busse, R., et al., EDHF: bringing the concepts together. Trends in pharmacological sciences, 2002. 23(8): p. 374-80.

(56) References Cited

OTHER PUBLICATIONS

Butt, E., et al., Endothelial nitric-oxide synthase (type III) is activated and becomes calcium independent upon phosphorylation by cyclic nucleotide-dependent protein kinases. The Journal of biological chemistry, 2000. 275(7): p. 5179-87.
Calder, P.C., Dietary modification of inflammation with lipids. The Proceedings of the Nutrition Society, 2002. 61(3): p. 345-58.
Calder, P.C., n-3 Fatty acids and cardiovascular disease: evidence explained and mechanisms explored. Clinical science, 2004. 107(1): p. 1-11.
Calder, P.C., Immunomodulation by omega-3 fatty acids. Prostaglandins, leukotrienes, and essential fatty acids, 2007. 77(5-6): p. 327-35.
Calder, P.C., Polyunsaturated fatty acids and inflammatory processes: New twists in an old tale. Biochimie, 2009. 91(6): p. 791-5.
Calder, P.C., The 2008 ESPEN Sir David Cuthbertson Lecture: Fatty acids and inflammation—from the membrane to the nucleus and from the laboratory bench to the clinic. Clinical nutrition, 2010. 29(1): p. 5-12.
Calder, P.C., Omega-3 polyunsaturated fatty acids and inflammatory processes: Nutrition or pharmacology? British journal of clinical pharmacology, 2012.
Calder, P.C., The role of marine omega-3 (n-3) fatty acids in inflammatory processes, atherosclerosis and plaque stability. Molecular nutrition & food research, 2012. 56(7): p. 1073-80.
Calo, L, et al., N-3 Fatty acids for the prevention of atrial fibrillation after coronary artery bypass surgery: a randomized, controlled trial. Journal of the American College of Cardiology, 2005. 45(10): p. 1723-8.
Calon, F., Nonpatentable drugs and the cost of our ignorance. CMAJ : Canadian Medical Association journal = journal de l'Association medicale canadienne, 2006. 174(4): p. 483-4.
Camins, A., et al., Sirtuin activators: designing molecules to extend life span. Biochimica et biophysica acta, 2010. 1799(10-12): p. 740-9.
Cao, J., et al., Incorporation and clearance of omega-3 fatty acids in erythrocyte membranes and plasma phospholipids. Clinical chemistry, 2006. 52(12): p. 2265-72.
Carpentier, Y.A., et al., Phospholipid and triacylglycerol fatty acid content and pattern in the cardiac endothelium of rats depleted in long-chain polyunsaturated omega 3 fatty acids. Cell biochemistry and function, 2008. 26(1): p. 33-8.
Carrepeiro, M.M., et al., Effect of n-3 fatty acids and statins on oxidative stress in statin-treated hypercholesterolemic and normocholesterolemic women. Atherosclerosis, 2011. 217(1): p. 171-8.
Caslake, M.J., et al., Effect of sex and genotype on cardiovascular biomarker response to fish oils: the FINGEN Study. The American journal of clinical nutrition, 2008. 88(3): p. 618-29.
Castro-Gonzalez, M.I. and M. Mendez-Armenta, Heavy metals: Implications associated to fish consumption. Environmental toxicology and pharmacology, 2008. 26(3): p. 263-71.
Cawood, A.L., et al., Eicosapentaenoic acid (EPA) from highly concentrated n-3 fatty acid ethyl esters is incorporated into advanced atherosclerotic plaques and higher plaque EPA is associated with decreased plaque inflammation and increased stability. Atherosclerosis, 2010. 212(1): p. 252-9.
Celermajer, D.S., et al., Endothelium-dependent dilation in the systemic arteries of asymptomatic subjects relates to coronary risk factors and their interaction. Journal of the American College of Cardiology, 1994. 24(6): p. 1468-74.
Chan, D.C. and G.F. Watts, Pharmacological regulation of dyslipoproteinaemia in insulin resistant states. Current vascular pharmacology, 2008. 6(1): p. 67-77.
Charakida, M., S. Masi, and J.E. Deanfield, The Year in Cardiology 2012: focus on cardiovascular disease prevention. European heart journal, 2013. 34(4): p. 314-7.
Chen, C., COX-2's new role in inflammation. Nature chemical biology, 2010. 6(6): p. 401-2.
Chen, L.G., et al., Tannin 1-alpha-O-galloylpunicalagin induces the calcium-dependent activation of endothelial nitric-oxide synthase via the phosphatidylinositol 3-kinase/Akt pathway in endothelial cells. Molecular nutrition & food research, 2008. 52(10): p. 1162-71.
Chen, Q., et al., Effects of omega-3 fatty acid for sudden cardiac death prevention in patients with cardiovascular disease: a contemporary meta-analysis of randomized, controlled trials. Cardiovascular drugs and therapy / sponsored by the International Society of Cardiovascular Pharmacotherapy, 2011. 25(3): p. 259-65.
Chen, Z.P., et al., AMP-activated protein kinase phosphorylation of endothelial NO synthase. FEBS letters, 1999. 443(3): p. 285-9.
Chin, J.P. and A.M. Dart, How do fish oils affect vascular function? Clinical and experimental pharmacology & physiology, 1995. 22(2): p. 71-81.
Chiuve, S.E., et al., Adherence to a low-risk, healthy lifestyle and risk of sudden cardiac death among women. JAMA : the journal of the American Medical Association, 2011. 306(1): p. 62-9.
Chokshi, A., et al., Ventricular assist device implantation corrects myocardial lipotoxicity, reverses insulin resistance, and normalizes cardiac metabolism in patients with advanced heart failure. Circulation, 2012. 125(23): p. 2844-53.
Chowdhury, R., et al., Association between fish consumption, long chain omega 3 fatty acids, and risk of cerebrovascular disease: systematic review and meta-analysis. BMJ, 2012. 345: p. e6698.
Coll, T., et al., Oleate reverses palmitate-induced insulin resistance and inflammation in skeletal muscle cells. The Journal of biological chemistry, 2008. 283(17): p. 11107-16.
Collins, N., et al., Differences between dietary supplement and prescription drug omega-3 fatty acid formulations: a legislative and regulatory perspective. Journal of the American College of Nutrition, 2008. 27(6): p. 659-66.
Connor, K.M., et al., Increased dietary intake of omega-3-polyunsaturated fatty acids reduces pathological retinal angiogenesis. Nature medicine, 2007. 13(7): p. 868-73.
Corson, M.A., et al., Phosphorylation of endothelial nitric oxide synthase in response to fluid shear stress. Circulation research, 1996. 79(5): p. 984-91.
Cottin, S.C., T.A. Sanders, and W.L. Hall, The differential effects of EPA and DHA on cardiovascular risk factors. The Proceedings of the Nutrition Society, 2011. 70(2): p. 215-31.
da Cunha, D.N., et al., n-3 (omega-3) polyunsaturated fatty acids prevent acute atrial electrophysiological remodeling. British journal of pharmacology, 2007. 150(3): p. 281-5.
Danaei, G., et al., The preventable causes of death in the United States: comparative risk assessment of dietary, lifestyle, and metabolic risk factors. PLoS medicine, 2009. 6(4): p. e1000058.
Davidson, M.H., et al., Clinical utility of inflammatory markers and advanced lipoprotein testing: advice from an expert panel of lipid specialists. Journal of clinical lipidology, 2011. 5(5): p. 338-67.
Davidson, M.H., et al., Separate and joint effects of marine oil and simvastatin in patients with combined hyperlipidemia. The American journal of cardiology, 1997. 80(6): p. 797-8.
Davidson, M.H., et al., Efficacy and tolerability of adding prescription omega-3 fatty acids 4 g/d to simvastatin 40 mg/d in hypertriglyceridemic patients: an 8-week, randomized, double-blind, placebo-controlled study. Clinical therapeutics, 2007. 29(7): p. 1354-67.
Daviglus, M.L., et al., Fish consumption and the 30-year risk of fatal myocardial infarction. The New England journal of medicine, 1997. 336(15): p. 1046-53.
Davila-Roman, V.G., et al., Altered myocardial fatty acid and glucose metabolism in idiopathic dilated cardiomyopathy. Journal of the American College of Cardiology, 2002. 40(2): p. 271-7.
Dawczynski, C., et al., n-3 LC-PUFA-enriched dairy products are able to reduce cardiovascular risk factors: a double-blind, blind, cross-over study. Clinical nutrition, 2010. 29(5): p. 592-9.
Dawczynski, C., et al., Randomized placebo-controlled intervention with n-3 LC-PUFA-supplemented yoghurt: Effects on circulating eicosanoids and cardiovascular risk factors. Clinical nutrition, 2012.
Dayspring, T.D., Understanding hypertriglyceridemia in women: clinical impact and management with prescription omega-3-acid ethyl esters. International journal of women's health, 2011. 3: p. 87-97.

(56) References Cited

OTHER PUBLICATIONS de Bathe, J., et al., Association between Omega3 and Omega6 fatty acid intakes and serum inflammatory markers in COPD. The Journal of nutritional biochemistry, 2012. 23(7): p. 817-21.
De Caterina, R., n-3 fatty acids in cardiovascular disease. The New England journal of medicine, 2011. 364(25): p. 2439-50.
Deckelbaum, R.J. and S.R. Akabas, n-3 Fatty acids and cardiovascular disease: navigating toward recommendations. The American journal of clinical nutrition, 2006. 84(1): p. 1-2.
Deedwania, P. and N. Volkova, Dyslipidemia and lipid-lowering therapy in the elderly. Expert review of cardiovascular therapy, 2005. 3(3): p. 453-63.
DeFilippis, A.P. and L.S. Sperling, Understanding omega-3's. American heart journal, 2006. 151(3): p. 564-70.
Demonty, I., et al., Fish-oil esters of plant sterols improve the lipid profile of dyslipidemic subjects more than do fish-oil or sunflower oil esters of plant sterols. The American journal of clinical nutrition, 2006. 84(6): p. 1534-42.
Den Ruijter, H.M., et al., Pro- and antiarrhythmic properties of a diet rich in fish oil. Cardiovascular research, 2007. 73(2): p. 316-25.
Denke, M.A. and S.M. Grundy, Individual responses to a cholesterol-lowering diet in 50 men with moderate hypercholesterolemia. Archives of internal medicine, 1994. 154(3): p. 317-25.
Dewell, A., et al., Low- and high-dose plant and marine (n-3) fatty acids do not affect plasma inflammatory markers in adults with metabolic syndrome. The Journal of nutrition, 2011. 141(12): p. 2166-71.
Di Angelantonio, E., et al., Lipid-related markers and cardiovascular disease prediction. JAMA : the journal of the American Medical Association, 2012. 307(23): p. 2499-506.
Dimmeler, S., et al., Suppression of apoptosis by nitric oxide via inhibition of interleukin-lbeta-converting enzyme (ICE)-like and cysteine protease protein (CPP)-32-like proteases. The Journal of experimental medicine, 1997. 185(4): p. 601-7.
Djousse, L., et al., Plasma omega-3 fatty acids and incident diabetes in older adults. The American journal of clinical nutrition, 2011. 94(2): p. 527-33.
Dodds, E.D., et al., Gas chromatographic quantification of fatty acid methyl esters: flame ionization detection vs. electron impact mass spectrometry. Lipids, 2005. 40(4): p. 419-28.
Dokholyan, R.S., et al., A trial of omega-3 fatty acids for prevention of hypertension. The American journal of cardiology, 2004. 93(8): p. 1041-3.
Domei, T., et al., Ratio of serum n-3 to n-6 polyunsaturated fatty acids and the incidence of major adverse cardiac events in patients undergoing percutaneous coronary intervention. Circulation journal : official journal of the Japanese Circulation Society, 2012. 76(2): p. 423-9.
Dona, M., et al., Resolvin E1, an EPA-derived mediator in whole blood, selectively counterregulates leukocytes and platelets. Blood, 2008. 112(3): p. 848-55.
Dougherty, R.M., et al., Lipid and phospholipid fatty acid composition of plasma, red blood cells, and platelets and how they are affected by dietary lipids: a study of normal subjects from Italy, Finland, and the USA. The American journal of clinical nutrition, 1987. 45(2): p. 443-55.
Durrington, P.N., et al., An omega-3 polyunsaturated fatty acid concentrate administered for one year decreased triglycerides in simvastatin treated patients with coronary heart disease and persisting hypertriglyceridaemia. Heart, 2001. 85(5): p. 544-8.
Dwyer, J., M.F. Picciano, and D.J. Raiten, Estimation of usual intakes: What We Eat in America—NHANES. The Journal of nutrition, 2003. 133(2): p. 609S-23S.
Eckel, R.H., The fish oil story remains fishy. Circulation, 2010. 122(21): p. 2110-2.
Egert, S. et al., Dietary alpha-linolenic acid, EPA, and DHA have differential effects on LDL fatty acid composition but similar effects on serum lipid profiles in normolipidemic humans. The Journal of nutrition, 2009. 139(5): p. 861-8.

Engler, M.B., et al., Mechanisms of vasorelaxation induced by eicosapentaenoic acid (20:5n-3) in WKY rat aorta. British journal of pharmacology, 2000. 131(8): p. 1793-9.
Enseleit, F., et al., Effects of Pycnogenol on endothelial function in patients with stable coronary artery disease: a double-blind, randomized, placebo-controlled, cross-over study. European heart journal, 2012. 33(13): p. 1589-97.
Erkkila, A.T., et al., Higher plasma docosahexaenoic acid is associated with reduced progression of coronary atherosclerosis in women with CAD. Journal of lipid research, 2006. 47(12): p. 2814-9.
Eussen, S.R., et al., Effects of n-3 fatty acids on major cardiovascular events in statin users and non-users with a history of myocardial infarction. European heart journal, 2012. 33(13): p. 1582-8.
Faber, J., et al., Supplementation with a fish oil-enriched, high-protein medical food leads to rapid incorporation of EPA into white blood cells and modulates immune responses within one week in healthy men and women. The Journal of nutrition, 2011. 141(5): p. 964-70.
Farooqui, A.A., L.A. Horrocks, and T. Farooqui, Modulation of inflammation in brain: a matter of fat. Journal of neurochemistry, 2007. 101(3): p. 577-99.
Farooqui, A.A., et al., Comparison of biochemical effects of statins and fish oil in brain: the battle of the titans. Brain research reviews, 2007. 56(2): p. 443-71.
Fedor, D. and D.S. Kelley, Prevention of insulin resistance by n-3 polyunsaturated fatty acids. Current opinion in clinical nutrition and metabolic care, 2009. 12(2): p. 138-46.
Fishman, G.I., et al., Sudden cardiac death prediction and prevention: report from a National Heart, Lung, and Blood Institute and Heart Rhythm Society Workshop. Circulation, 2010. 122(22): p. 2335-48.
Fleming, I., et al., Phosphorylation of Thr(495) regulates Ca(2+)/calmodulin-dependent endothelial nitric oxide synthase activity. Circulation research, 2001. 88(11): p. E68-75.
Folch, J., M. Lees, and G.H. Sloane Stanley, A simple method for the isolation and purification of total lipides from animal tissues. The Journal of biological chemistry, 1957. 226(1): p. 497-509.
Ford, E.S., K.J. Greenlund, and Y. Hong, Ideal cardiovascular health and mortality from all causes and diseases of the circulatory system among adults in the United States. Circulation, 2012. 125(8): p. 987-95.
Frasure-Smith, N. and F. Lesperance, Depression and anxiety as predictors of 2-year cardiac events in patients with stable coronary artery disease. Archives of general psychiatry, 2008. 65(1): p. 62-71.
Dietary supplementation with n-3 polyunsaturated fatty acids and vitamin E after myocardial infarction: results of the GISSI-Prevenzione trial. Gruppo Italiano per lo Studio della Sopravvivenza nell'Infarto miocardico. Lancet, 1999. 354(9177): p. 447-55.
Aarsetoey, H., et al., Low levels of the omega-3 index are associated with sudden cardiac arrest and remain stable in survivors in the subacute phase. Lipids, 2011.46(2): p. 151-61.
Aarsetoey, H., et al., (n-3) Fatty acid content of red blood cells does not predict risk of future cardiovascular events following an acute coronary syndrome. The Journal of nutrition, 2009. 139(3): p. 507-13.
Abrahams, B.S. and D.H. Geschwind, Advances in autism genetics: on the threshold of a new neurobiology. Nature reviews. Genetics, 2008. 9(5): p. 341-55.
Adkins, Y. and D.S. Kelley, Mechanisms underlying the cardioprotective effects of omega-3 polyunsaturated fatty acids. The Journal of nutritional biochemistry, 2010. 21(9): p. 781-92.
Ahmed, M., et al., Varying quality of fish oil capsules: fatty acids and tocopherol. Neuro endocrinology letters, 2011. 32 Suppl 2: p. 37-40.
Akiyama, T., et al., Increased risk of death and cardiac arrest from encainide and flecainide in patients after non-Q-wave acute myocardial infarction in the Cardiac Arrhythmia Suppression Trial. CAST Investigators. The American journal of cardiology, 1991. 68(17): p. 1551-5.
Albert, C.M., Dietary n-3 fatty acid intake and risk of sudden death and coronary artery disease. Current treatment options in cardiovascular medicine, 2007. 9(1): p. 71-7.
Albert, C.M., Prediction of sudden cardiac death in patients with coronary heart disease: the challenge ahead. Circulation. Cardiovascular imaging, 2008. 1(3): p. 175-7.

(56) References Cited

OTHER PUBLICATIONS

Albert, C.M., Omega-3 fatty acids and ventricular arrhythmias: nothing is simple. American heart journal, 2008. 155(6): p. 967-70.
Albert, C.M., Sudden cardiac death risk prediction: comment on "Risk factor and prediction modeling for sudden cardiac death in women with coronary artery disease". Archives of internal medicine, 2011. 171(19): p. 1710-1.
Albert, C.M., et al., Blood levels of long-chain n-3 fatty acids and the risk of sudden death. The New England journal of medicine, 2002. 346(15): p. 1113-8.
Albert, C.M., et al., Prospective study of sudden cardiac death among women in the United States. Circulation, 2003. 107(16): p. 2096-101.
Albert, C.M., et al., Fish consumption and risk of sudden cardiac death. JAMA : the journal of the American Medical Association, 1998. 279(1): p. 23-8.
Albert, C.M., et al., Prospective study of C-reactive protein, homocysteine, and plasma lipid levels as predictors of sudden cardiac death. Circulation, 2002. 105(22): p. 2595-9.
Albert, C.M., et al., Common variants in cardiac ion channel genes are associated with sudden cardiac death. Circulation. Arrhythmia and electrophysiology, 2010. 3(3): p. 222-9.
Albert, C.M., et al., Cardiac sodium channel gene variants and sudden cardiac death in women. Circulation, 2008. 117 (1): p. 16-23.
Albert, C.M., et al., Dietary alpha-linolenic acid intake and risk of sudden cardiac death and coronary heart disease. Circulation, 2005. 112(21): p. 3232-8.
Alberti, K.G., et al., Harmonizing the metabolic syndrome: a joint interim statement of the International Diabetes Federation Task Force on Epidemiology and Prevention; National Heart, Lung, and Blood Institute; American Heart Association; World Heart Federation; International Atherosclerosis Society; and International Association for the Study of Obesity. Circulation, 2009. 120(16): p. 1640-5.
Amano, T, et al., Impact of omega-3 polyunsaturated fatty acids on coronary plaque instability: an integrated backscatter intravascular ultrasound study. Atherosclerosis, 2011. 218(1): p. 110-6.
Anderson, J.S., et al., Associations of plasma phospholipid omega-6 and omega-3 polyunsaturated Fatty Acid levels and MRI measures of cardiovascular structure and function: the multiethnic study of atherosclerosis. Journal of nutrition and metabolism, 2011. 2011: p. 315134.
Anderson, T.J., et al., Close relation of endothelial function in the human coronary and peripheral circulations. Journal of the American College of Cardiology, 1995. 26(5): p. 1235-41.
Anselm, E., et al., Grape juice causes endothelium-dependent relaxation via a redox-sensitive Src- and Akt-dependent activation of eNOS. Cardiovascular research, 2007. 73(2): p. 404-13.
Antonetti, D.A., R. Klein, and T.W. Gardner, Diabetic retinopathy. The New England journal of medicine, 2012. 366 (13): p. 1227-39.
Arita, M., et al., Resolvin E1, an endogenous lipid mediator derived from omega-3 eicosapentaenoic acid, protects against 2,4,6-trinitrobenzene sulfonic acid-induced colitis. Proceedings of the National Academy of Sciences of the United States of America, 2005. 102(21): p. 7671-6.
Axelrod, L, Omega-3 fatty acids in diabetes mellitus. Gift from the sea? Diabetes, 1989. 38(5): p. 539-43.
Baghai, T.C., et al., Major depressive disorder is associated with cardiovascular risk factors and low Omega-3 Index. The Journal of clinical psychiatry, 2011. 72(9): p. 1242-7.
Bailey-Hall, E., E.B. Nelson, and A.S. Ryan, Validation of a rapid measure of blood PUFA levels in humans. Lipids, 2008. 43(2): p. 181-6.
Bangalore, S., et al., Short- and long-term outcomes with drug-eluting and bare-metal coronary stents: a mixed-treatment comparison analysis of 117 762 patient-years of follow-up from randomized trials. Circulation, 2012. 125(23): p. 2873-91.
Bannenberg, G.L., Therapeutic applicability of anti-inflammatory and proresolving polyunsaturated fatty acid-derived lipid mediators. TheScientificWorldJournal, 2010. 10: p. 676-712.

Barcelo-Coblijn, G. and E.J. Murphy, Alpha-linolenic acid and its conversion to longer chain n-3 fatty acids: benefits for human health and a role in maintaining tissue n-3 fatty acid levels. Progress in lipid research, 2009. 48(6): p. 355-74.
Bauer, P.M., et al., Compensatory phosphorylation and protein-protein interactions revealed by loss of function and gain of function mutants of multiple serine phosphorylation sites in endothelial nitric-oxide synthase. The Journal of biological chemistry, 2003. 278(17): p. 14841-9.
Bays, H., Clinical overview of Omacor: a concentrated formulation of omega-3 polyunsaturated fatty acids. The American journal of cardiology, 2006. 98(4A): p. 71i-76i.
Bays, H.E., Safety considerations with omega-3 fatty acid therapy. The American journal of cardiology, 2007. 99(6A): p. 35C-43C.
Bays, H.E., et al., Icosapent Ethyl, a Pure Ethyl Ester of Eicosapentaenoic Acid: Effects on Circulating Markers of Inflammation from the Marine and Anchor Studies. American journal of cardiovascular drugs : drugs, devices, and other interventions, 2013.
Bays, H.E., et al., Eicosapentaenoic acid ethyl ester (AMR101) therapy in patients with very high triglyceride levels (from the Multi-center, plAcebo-controlled, Randomized, double-blINd, 12-week study with an open-label Extension [Marine] trial). The American journal of cardiology, 2011. 108(5): p. 682-90.
Bays, H.E. et al. Prescription omega-3 fatty acids and their lipid effects: physiologic mechanisms of action and clinical implications. Expert review of cardiovascular therapy, 2008. 6(3): p. 391-409.
Beavers, K.M., et al., Omega-3 fatty acid supplementation and total homocysteine levels in end-stage renal disease patients. Nephrology, 2008. 13(4): p. 284-8.
Begin, M.E., et al., What Is the Link between Docosahexaenoic Acid, Cognitive Impairment, and Alzheimer's Disease in the Elderly?, in Fat Detection: Taste, Texture, and Post Ingestive Effects, J.P. Montmayeur and J. le Coutre, Editors. 2010: Boca Raton (FL).
Belayev, L., et al., Robust docosahexaenoic acid-mediated neuroprotection in a rat model of transient, focal cerebral ischemia. Stroke; a journal of cerebral circulation, 2009. 40(9): p. 3121-6.
Belayev, L, et al., Docosahexaenoic Acid Therapy of Experimental Ischemic Stroke. Translational stroke research, 2011. 2(1): p. 33-41.
Belayev, L., et al., Docosahexaenoic acid complexed to albumin elicits high-grade ischemic neuroprotection. Stroke; a journal of cerebral circulation, 2005. 36(1): p. 118-23.
Benzie, I.F. and J.J. Strain, The ferric reducing ability of plasma (FRAP) as a measure of "antioxidant power": the FRAP assay. Analytical biochemistry, 1996. 239(1): p. 70-6.
Berry, J.D. et al., Dietary fish intake and incident atrial fibrillation (from the Women's Health Initiative). The American journal of cardiology, 2010. 105(6): p. 844-8.
Bhattacharya, A., et al., Different ratios of eicosapentaenoic and docosahexaenoic omega-3 fatty acids in commercial fish oils differentially alter pro-inflammatory cytokines in peritoneal macrophages from C57BL/6 female mice. The Journal of nutritional biochemistry, 2007. 18(1): p. 23-30.
Bifulco, M. and S. Pisanti, End of the line for cannabinoid receptor 1 as an anti-obesity target? an opinion. Nature reviews. Drug discovery, 2009. 8(7): p. 594.
Billman, G.E., J.X. Kang, and A. Leaf, Prevention of sudden cardiac death by dietary pure omega-3 polyunsaturated fatty acids in dogs. Circulation, 1999. 99(18): p. 2452-7.
Bitzur, R., et al., The metabolic effects of omega-3 plant sterol esters in mixed hyperlipidemic subjects. Cardiovascular drugs and therapy / sponsored by the International Society of Cardiovascular Pharmacotherapy, 2010. 24(5-6): p. 429-37.
Bjerregaard, L.J., et al., Fish intake and acute coronary syndrome. European heart journal, 2010. 31(1): p. 29-34.
Blasbalg, T.L., et al., Changes in consumption of omega-3 and omega-6 fatty acids in the United States during the 20th century. The American journal of clinical nutrition, 2011. 93(5): p. 950-62.
Omura, M., et al., Eicosapentaenoic acid (EPA) induces Ca(2+)-independent activation and translocation of endothelial nitric oxide synthase and endothelium-dependent vasorelaxation. FEBS letters, 2001. 487(3): p. 361-6.
Orchard, T.S., et al., The association of red blood cell n-3 and n-6 fatty acids to dietary fatty acid intake, bone mineral density and hip frac-

(56) References Cited

OTHER PUBLICATIONS ture risk in the Women's Health Initiative. Journal of bone and mineral research : the official journal of the American Society for Bone and Mineral Research, 2012.
Otvos, J.D., et al., Clinical implications of discordance between low-density lipoprotein cholesterol and particle number. Journal of clinical lipidology, 2011. 5(2): p. 105-13.
Parker, G., et al., Omega-3 fatty acids and mood disorders. The American journal of psychiatry, 2006. 163(6): p. 969-78.
Pase, M.P., N.A. Grima, and J. Sarris, Do long-chain n-3 fatty acids reduce arterial stiffness? A meta-analysis of randomised controlled trials. The British journal of nutrition, 2011. 106(7): p. 974-80.
Pasiakos, S.M., et al., Cardiometabolic risk in US Army recruits and the effects of basic combat training. PloS one, 2012. 7(2): p. e31222.
Patterson, C., et al., Diagnosis and treatment of dementia: 1. Risk assessment and primary prevention of Alzheimer disease. CMAJ : Canadian Medical Association journal = journal de l'Association medicale canadienne, 2008. 178(5): p. 548-56.
Patton, K.K., et al., N-terminal pro-B-type natriuretic peptide is associated with sudden cardiac death risk: the Cardiovascular Health Study. Heart rhythm : the official journal of the Heart Rhythm Society, 2011. 8(2): p. 228-33.
Patwari, P., et al., Thioredoxin-independent regulation of metabolism by the alpha-arrestin proteins. The Journal of biological chemistry, 2009. 284(37): p. 24996-5003.
Pauwels, E.K. and M. Kostkiewicz, Fatty acid facts, Part III: Cardiovascular disease, or, a fish diet is not fishy. Drug news & perspectives, 2008. 21(10): p. 552-61.
Pedersen, M.W., et al., The effect of marine n-3 fatty acids in different doses on plasma concentrations of Lp-PLA2 in healthy adults. European journal of nutrition, 2009. 48(1): p. 1-5.
Pencina, M.J., et al., Predicting the 30-year risk of cardiovascular disease: the framingham heart study. Circulation, 2009. 119(24): p. 3078-84.
Perez-Martinez, P. et al., Glucokinase regulatory protein genetic variant interacts with omega-3 PUFA to influence insulin resistance and inflammation in metabolic syndrome. PloS one, 2011. 6(6): p. e20555.
Perk, J., et al., European guidelines on cardiovascular disease prevention in clinical practice (version 2012) : the fifth joint task force of the European society of cardiology and other societies on cardiovascular disease prevention in clinical practice (constituted by representatives of nine societies and by invited experts). International journal of behavioral medicine, 2012. 19(4): p. 403-88.
Peters, R.J., et al., Videodensitometric quantitative angiography after coronary balloon angioplasty, compared to edge-detection quantitative angiography and intracoronary ultrasound imaging. European heart journal, 2000. 21(8): p. 654-61.
Petrova, S., et al., The global availability of n-3 fatty acids. Public health nutrition, 2011. 14(7): p. 1157-64.
Pflanz, S. and S. Sonnek, Work stress in the military: prevalence, causes, and relationship to emotional health. Military medicine, 2002. 167(11): p. 877-82.
Phang, M., et al., Gender-specific inhibition of platelet aggregation following omega-3 fatty acid supplementation. Nutrition, metabolism, and cardiovascular diseases : NMCD, 2012. 22(2): p. 109-14.
Pickersgill, L. et al., Key role for ceramides in mediating insulin resistance in human muscle cells. The Journal of biological chemistry, 2007. 282(17): p. 12583-9.
Piscitelli, F., et al., Effect of dietary krill oil supplementation on the endocannabinoidome of metabolically relevant tissues from high-fat-fed mice. Nutrition & metabolism, 2011. 8(1): p. 51.
Pottala, J.V., et al., Blood eicosapentaenoic and docosahexaenoic acids predict all-cause mortality in patients with stable coronary heart disease: the Heart and Soul study. Circulation. Cardiovascular quality and outcomes, 2010. 3(4): p. 406-12.
Poudyal, H., et al., Omega-3 fatty acids and metabolic syndrome: effects and emerging mechanisms of action. Progress in lipid research, 2011. 50(4): p. 372-87.

Pownall, H.J., et al., Correlation of serum triglyceride and its reduction by omega-3 fatty acids with lipid transfer activity and the neutral lipid compositions of high-density and low-density lipoproteins. Atherosclerosis, 1999. 143(2): p. 285-97.
Pratt, C.M., et al., Efficacy and safety of prescription omega-3-acid ethyl esters for the prevention of recurrent symptomatic atrial fibrillation: a prospective study. American heart journal, 2009. 158(2): p. 163-169 e1-3.
Pritchard, K.A., Jr., et al., Heat shock protein 90 mediates the balance of nitric oxide and superoxide anion from endothelial nitric-oxide synthase. The Journal of biological chemistry, 2001. 276(21): p. 17621-4.
Psota, T.L., S.K. Gebauer, and P. Kris-Etherton, Dietary omega-3 fatty acid intake and cardiovascular risk. The American journal of cardiology, 2006. 98(4A): p. 3i-18i.
Puglisi, M.J., A.H. Hasty, and V. Saraswathi, The role of adipose tissue in mediating the beneficial effects of dietary fish oil. The Journal of nutritional biochemistry, 2011. 22(2): p. 101-8.
Qi, K., et al., Omega-3 fatty acid containing diets decrease plasma triglyceride concentrations in mice by reducing endogenous triglyceride synthesis and enhancing the blood clearance of triglyceride-rich particles. Clinical nutrition, 2008. 27(3): p. 424-30.
Racette, S.B., et al., Dose effects of dietary phytosterols on cholesterol metabolism: a controlled feeding study. The American journal of clinical nutrition, 2010. 91(1): p. 32-8.
Raitt, M.H., et al., Fish oil supplementation and risk of ventricular tachycardia and ventricular fibrillation in patients with implantable defibrillators: a randomized controlled trial. JAMA : the journal of the American Medical Association, 2005. 293(23): p. 2884-91.
Rame, J.E., Chronic heart failure: a reversible metabolic syndrome? Circulation, 2012. 125(23): p. 2809-11.
Rauch, B., et al., Omega, a randomized, placebo-controlled trial to test the effect of highly purified omega-3 fatty acids on top of modern guideline-adjusted therapy after myocardial infarction. Circulation, 2010. 122(21): p. 2152-9.
Ray, K.K., et al., Relation between soluble intercellular adhesion molecule-1, statin therapy, and long-term risk of clinical cardiovascular events in patients with previous acute coronary syndrome (from PROVE IT-TIMI 22). The American journal of cardiology, 2006. 98(7): p. 861-5.
Regan, J., et al., Suicide and the military. Tennessee medicine : journal of the Tennessee Medical Association, 2005. 98(8): p. 400-1.
Richardson, A.J., Omega-3 fatty acids in ADHD and related neurodevelopmental disorders. International review of psychiatry, 2006. 18(2): p. 155-72.
Richardson, A.J. and P. Montgomery, The Oxford-Durham study: a randomized, controlled trial of dietary supplementation with fatty acids in children with developmental coordination disorder. Pediatrics, 2005. 115(5): p. 1360-6.
Richardson, A.J. and B.K. Puri, A randomized double-blind, placebo-controlled study of the effects of supplementation with highly unsaturated fatty acids on ADHD-related symptoms in children with specific learning difficulties. Progress in neuro-psychopharmacology & biological psychiatry, 2002. 26(2): p. 233-9.
Riediger, N.D., et al., A systemic review of the roles of n-3 fatty acids in health and disease. Journal of the American Dietetic Association, 2009. 109(4): p. 668-79.
Rissanen, T., et al., Fish oil-derived fatty acids, docosahexaenoic acid and docosapentaenoic acid, and the risk of acute coronary events: the Kuopio ischaemic heart disease risk factor study. Circulation, 2000. 102(22): p. 2677-9.
Rivellese, A.A., C. De Natale, and S. Lilli, Type of dietary fat and insulin resistance. Annals of the New York Academy of Sciences, 2002. 967: p. 329-35.
Rizos, E.C., et al., Association between omega-3 fatty acid supplementation and risk of major cardiovascular disease events: a systematic review and meta-analysis. JAMA : the journal of the American Medical Association, 2012. 308 (10): p. 1024-33.
Roger, V.L. et al. Heart disease and stroke statistics—2011 update: a report from the American Heart Association. Circulation, 2011. 123(4): p. e18-e209.

(56) References Cited

OTHER PUBLICATIONS

Roger, V.L. et al. Heart disease and stroke statistics—2012 update: a report from the American Heart Association. Circulation, 2012. 125(1): p. e2-e220.

Roland, I., et al., Modulation of the arachidonic cascade with omega3 fatty acids or analogues: potential therapeutic benefits. Mini reviews in medicinal chemistry, 2004. 4(6): p. 659-68.

Rosenzweig, J.L., et al., Primary prevention of cardiovascular disease and type 2 diabetes in patients at metabolic risk: an endocrine society clinical practice guideline. The Journal of clinical endocrinology and metabolism, 2008. 93(10): p. 3671-89.

Roth, E.M. and W.S. Harris, Fish oil for primary and secondary prevention of coronary heart disease. Current atherosclerosis reports, 2010. 12(1): p. 66-72.

Ruan, C.H., et al., Prostacyclin therapy for pulmonary arterial hypertension. Texas Heart Institute journal / from the Texas Heart Institute of St. Luke's Episcopal Hospital, Texas Children's Hospital, 2010. 37(4): p. 391-9.

Rupp, H., et al., Mechanisms involved in the differential reduction of omega-3 and omega-6 highly unsaturated fatty acids by structural heart disease resulting in "HUFA deficiency". Canadian journal of physiology and pharmacology, 2012. 90(1): p. 55-73.

Rupp, H., et al., Risk stratification by the "EPA+DHA level" and the "EPA/AA ratio" focus on anti-inflammatory and antiarrhythmogenic effects of long-chain omega-3 fatty acids. Herz, 2004. 29(7): p. 673-85.

Saifullah, A., et al., Oral fish oil supplementation raises blood omega-3 levels and lowers C-reactive protein in haemodialysis patients—a pilot study. Nephrology, dialysis, transplantation : official publication of the European Dialysis and Transplant Association—European Renal Association, 2007. 22(12): p. 3561-7.

* cited by examiner

CHOLESTEROL ABSORPTION INHIBITOR AND OMEGA 3 FATTY ACIDS FOR THE REDUCTION OF CHOLESTEROL AND FOR THE PREVENTION OR REDUCTION OF CARDIOVASCULAR, CARDIAC AND VASCULAR EVENTS

CROSS-REFERENCE TO RELATED APPLICATIONS

This application is a continuation-in-part of PCT/US2012/025003, filed Feb. 14, 2012, which claims benefit of priority to U.S. Provisional Patent Application Ser. No. 61/457,268, filed Feb. 16, 2011, the contents of which are incorporated herein by reference in their entireties.

FIELD OF THE INVENTION

The present invention relates to combinations of one or more cholesterol absorption inhibitors, such as ezetimibe, with mixtures of omega-3 fatty acid compositions designed to mediate omega-3 deficiencies in individuals in need thereof; and to methods of administering such combinations, and to unit dosages of such combinations for the reduction of circulating cholesterol levels in cardiovascular disease patients (CVD). The invention particularly relates to compositions wherein the omega-3 formulation is designed to mediate omega-3 deficiencies in individuals in need thereof; particularly to compositions containing specific ratios of highly purified long chain fatty acid compositions which are effective in elevating omega-3 levels to a point at which the risk factors for cardiovascular disease are mitigated, and most particularly to a composition having an EPA:DHA ratio and level of omega-3 purity which enable them to be effective in providing a sustained vasodilatory effect, defined as a vasodilatory effect lasting at least 6 hours.

BACKGROUND OF THE INVENTION

Cardiovascular disease (CVD) represents the primary cause of mortality for men and women in developed countries globally. These premature deaths come at great cost to both the individuals and their families, as well as representing a huge burden to the health care system of the country. The risk factors for coronary heart disease are well-recognized and include: higher than average serum cholesterol, elevated levels of LDL; a low level of HDL in proportion to the LDL level; higher than average serum triglycerides; and higher levels of lipid oxidation products creating plaques and streaks which cause blockages of coronary arteries. An additional risk factor for coronary heart disease and stroke is high blood pressure. Reduction in these risk factors is effective to reduce the prevalence of coronary heart disease and its many costs.

In humans, cholesterol and triglycerides are part of the total lipoprotein complexes present in the bloodstream, characterized as high-density lipoprotein (HDL), intermediate-density lipoprotein (IDL), low-density lipoprotein (LDL) and very-low-density lipoprotein (VLDL) fractions.

Cholesterol and triglycerides are synthesized in the liver, incorporated into VLDL, and released into the plasma. High levels of total cholesterol (total-C), LDL-C, and apolipoprotein B (a membrane complex for LDL-C) promote human atherosclerosis and decreased levels of HDL-C and its transport complex, apolipoprotein A, which are associated with the development of atherosclerosis. Cardiovascular morbidity and mortality in humans can vary directly with the level of total-C and LDL-C and inversely with the level of HDL-C.

Cholesterol absorption inhibitors are known (see for example Rosenblum, S. B., et al., J. Med. Chem., 41(6):973-80 (1998)).

Although in some cases, genetic predisposition contributes to CVD incidence, poor diet and sedentary lifestyle are major factors that contribute to increased risk for the development, and progression of CVD. Because of this, clinical management of CVD often includes an attempt to modify a patient's lifestyle to increase exercise, and incorporate a balanced diet, rich in omega-3 fatty acids. Due to non-compliance, and often an inability of a patient to adhere to lifestyle modifications, optimal patient care is not achieved through these efforts alone, and other therapeutic interventions or strategies must be considered.

Treatment options may include lipid-regulating medications, such as statins, or fibrates that act to lower low density lipoprotein (LDL) cholesterol and/or triglycerides (TG), metabolic components that are thought to contribute to atherosclerotic plaque buildup, and increase the risk for heart attack or stroke. Additional therapies may include the use of lipid-lowering compounds that selectively inhibit the intestinal absorption of cholesterol. However, many of these treatment options come with unwanted side effects that could add additional health risks, or cause physical discomfort.

Azetidinone-based compounds, e.g. ezetimibe, are an example of cholesterol absorption inhibitors (see Bioorg. Med. Chem., 7(10):2199-202 (1999)). Ezetimibe is in a class of lipid-lowering compounds that selectively inhibits the intestinal absorption of cholesterol and related phytosterols. It is a white, crystalline powder that is freely to very soluble in ethanol, methanol, and acetone and practically insoluble in water. The chemical name is (3R,4S)-1-(p-fluorophenyl)-3-[(3S)-3-(p-fluorophenyl)-3-hydroxypropyl]-4-(p-hydroxyphenyl)-2-azetidinone(6) and the molecular formula is $C_{24}H_{21}F_2NO_3$. It is marketed under such tradenames as EZE-DOC, EZEE, EZET, EZETIB, EZZICARD, LIPEZET, ZETICA, EZTA, and EZIBLOC.

In the field of CVD prevention, there is no single prior art composition which reduces the variety of risk factors associated with this pervasive disease and which has wide spread applicability to the population in developed countries.

In one aspect, the present invention provides a novel composition, which may be incorporated into an orally administered dietary regimen for the reduction of risk factors associated with CVD. The composition of the invention represents a unique combination of one or more cholesterol absorption inhibitors with an omega 3 fatty acid formulation.

In accordance with the findings of the U.S. 2005 Dietary Guidelines Advisory Committee, 70% of Americans are omega-3 fatty acid deficient. Further studies indicate that over 84% of CVD patients are deficient in omega-3 fatty acids, specifically Eicosapentaenoic acid (EPA), Docosahexaenoic acid (DHA) and Docosapentaenoic acid (DPA).

Omega-3 fatty acids are natural polyunsaturated fats found in sea foods like fish and which are presently also available as dietary supplements. They contain more than one double bond in the aliphatic chain. They are named according to the number (>1), position and configuration of double bounds. The three major types of omega-3 fatty acids are alpha-linolenic acid (ALA), eicosapentaenoic acid (EPA), and docosahexaenoic acid (DHA). These omega-3 polyunsaturated fatty acids have been shown to protect against several types of cardiovascular diseases such as myocardial infarction, arrhythmia, atherosclerosis, and hypertension (Abeywardena and Head, 2001; Kris-Etherton et al., 2003). It is widely accepted that (EPA) (C20:5n-3) and (DHA) (C22:6n-3) are the major biological active polyunsaturated fatty acids contributing to the prevention of a variety of cardiovascular disorders by improving endothelium-dependent vasodilatation and preventing activation of platelets. Fish oil, EPA and DHA have been shown to induce relaxation and inhibit contraction by mechanisms which are endothelium-dependent (Shimokawa et al., 1987; Yanagisawa and Lefer, 1987). High contents of omega-3 polyunsaturated fatty acids, especially EPA, inhibited platelet aggregation and increased bleeding time, presumably due to a reduced generation of thromboxane $A_2$. Previous studies have also shown that dietary supplementation with cod-liver oil purified omega-3 fatty acids potentiated endothelium-dependent relaxations in isolated porcine coronary arteries (Shimokawa et al., 1988).

If a combination therapy including a novel omega-3 formulation in combination with one or more cholesterol absorption inhibitors, could be provided for enhancing the patient's lipid profile and mitigating the various risk factors for cardiovascular disease, particularly reduction of overall serum cholesterol levels, reductions in high blood pressure and pulse rate, increase in the HDL:LDL ratio, reduction of triglycerides and homocysteine levels, lowering of the activity of the blood coagulation factor VII-phospholipid complex, and prevention of lipid oxidation and the formation of plaques, a long felt need would be realized.

SUMMARY OF THE INVENTION

The prior art fails to disclose a pharmaceutical formulation as set forth in the instantly disclosed invention, containing the combination of a cholesterol absorption inhibitor and an omega-3 composition containing about 90% or greater omega 3 fatty acids by weight having a combination of Eicosapentaenoic acid (EPA) and Docosahexaenoic acid (DHA) in a weight ratio of EPA:DHA of from 5.7 to 6.3, wherein the sum of the EPA, DHA and DPA is about 82% by weight of the total formulation and about 92% of the total omega 3 fatty acid content of the composition. EPA+DHA are about 80% of the total formulation and about 89% of the total omega 3 fatty acid content of the composition. In combination, each of these components, which independently reduce one or more of the risk factors for cardiovascular disease (CVD), are expected to work synergistically to reduce the risk of CVD more effectively than any of these components taken alone.

It is noteworthy that tailoring the ratios, content and purity of omega fatty acid formulations provides the skilled artisan with a significant set of specific parameters, whereby formulations having a desired utility or pharmacological action may be derived.

The present inventors have discovered that the ability of omega-3 fatty acid preparations to cause endothelium-dependent relaxations depends on their relative content of EPA and DHA, as well as the purity of the overall formulation and the presence of additional key omega-3 fatty acids, particularly DPA.

Indeed, formulations in accordance with the present invention having an EPA:DHA ratio of about 6:1 induced significantly greater relaxations than an EPA:DHA 1:1 preparation despite their similar content of omega-3 fatty acids. These findings also suggest that EPA is likely to be a more potent endothelium-dependent vasorelaxant agonist than DHA. The fact that the two major omega-3 fatty acids do not have similar biological activity to cause endothelium-dependent relaxation is important since the leading commercial omega-3 preparations (Lovaza®) has a ratio of EPA:DHA 1.2:1. Thus, the optimization of the ratio of EPA:DHA in omega-3 preparations may provide new products with an enhanced vascular protective potential.

The present invention provides a novel composition, which may be incorporated into an orally administered formulation for the reduction of risk factors associated with CVD, and a novel treatment method. A composition of the formulation of the invention may be used orally to treat and/or prevent risk factors of CVD and stroke, including reduction of high blood pressure and improving overall lipid profiles, e.g. low density lipoprotein (LDL), high density lipoprotein (HDL) and triglycerides. While not wishing to be bound by theory, the inventors believe that the compositions work by acting at different sites and aspects of cardiovascular disease. The compositions of the present invention are preferably presented for administration to humans and animals in unit dosage forms, such as tablets, capsules, pills, powders, granules, and oral solutions or suspensions and the like, containing suitable quantities of an active ingredient.

The present invention also provides methods of treatment, for example administering to a patient having an omega-3 fatty acid deficiency, that may be evidencing one or more risk factors for CVD, a therapeutically effective amount of a formulation in accordance with the invention to achieve a therapeutic level of omega-3; whereby mitigation of said one or more risk factors for CVD is achieved. In embodiments, the invention is also a method for providing a sustained vasodilatory effect in a patient by administering a therapeutically effective amount of a formulation in accordance with the invention, whereby an indomethacin-independent sustained vasodilatory effect is achieved.

By providing a method of treatment for mediating omega-3 deficiencies, use of the instant invention to improve the health of the heart and to reduce risk factors associated with cardiovascular disease by delivering to an individual the composition of the invention is realized. Delivery of the composition of the invention, e.g., by oral administration, has been shown to be useful for preventing oxidation of low density lipoprotein (LDL), increasing high density lipoprotein (HDL), and for reducing total cholesterol. Delivery of the composition of the invention is also useful for reducing triglycerides and reducing homocysteine.

Desirably, the compositions of the invention are formulated such that an effective amount is delivered by multiple tablets (or other suitable formulation) a day. Suitably, these doses may be taken with meals, mixed into food, or taken on an empty stomach. Generally improvement is observed after two to eight weeks of daily use. Optionally, the compositions of the invention may be delivered daily in a suitable form (e.g., a chew or bar). Other suitable dosage regimens may be readily developed by one of skill in the art. Such dosage regimens are not a limitation of the invention. The compositions of the present invention, in addition to their use in treating CVD in humans, may also be useful in treating non-human animals, particularly mammals. For example, these dietary supplements may be useful for companion animals such as dogs and cats, for cattle, horses, and pigs, among other animals.

A primary objective of the instant invention is to teach a combined therapy comprising a cholesterol absorption inhibitor and an omega-3 fatty acid formulation. The combined therapy may be supplied either as single dosage forms or in a combined dosage form. One or more cholesterol absorption inhibitors are useful in the treatment of patients with hypertriglyceridemia, hypercholesterolemia, mixed dyslipidemia, atherosclerotic disease, coronary heart disease (CHD) and cardiovascular disease (CVD). Exemplary, albeit non-limiting examples are ezetimibes marketed under such tradenames as EZEDOC, EZEE, EZET, EZETIB, EZZI-CARD, LIPEZET, ZETICA, EZTA, and EZIBLOC or pharmaceutically acceptable salts thereof or a combination thereof. These cholesterol absorption inhibitors are provided along with mixtures of an omega-3 fatty acid formulation containing a minimum of 90% omega 3 fatty acids by weight including a combination of Eicosapentaenoic acid (EPA) and Docosahexaenoic acid (DHA) in a weight ratio of EPA:DHA of from 5.7 to 6.3, wherein the sum of the EPA, DHA and DPA are about 82% by weight of the total formulation and about 92% of the total omega 3 fatty acid content of the composition. EPA+DHA are about 80% of the total formulation and about 89% of the total omega 3 fatty acid content of the composition.

The fatty acids of the present invention are understood to include biologically active glyceride forms, e.g. triglycerides, biologically active ester forms, e.g. ethyl ester forms, and biologically active phospholipid forms, their derivatives, conjugates, precursors, and pharmaceutically acceptable salts and mixtures thereof. It is understood that the combination of omega-3 formulation and cholesterol absorption inhibitors may be provided as a single unit dosage form, or as separate and distinct unit dosage forms.

A further objective of the instant invention is to teach methods of administering such combinations, and unit dosages of such combinations for the treatment of hypertriglyceridemia, hypercholesterolemia, mixed dyslipidemia, atherosclerotic disease, and vascular disease in cardiovascular disease patients (CVD), whereinby these risk factors are lowered significantly.

It is a further objective of the instant invention to provide a method and system for its practice to mediate omega-3 deficiency in patients having a need therefore, while assisting such patients in improving their lipid profile by the co-administration of a cholesterol absorption inhibitor and an omega 3 fish oil.

These and other advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof. All examples are illustrative and non-limiting in view of the disclosure.

DETAILED DESCRIPTION OF THE INVENTION

Figure 1:
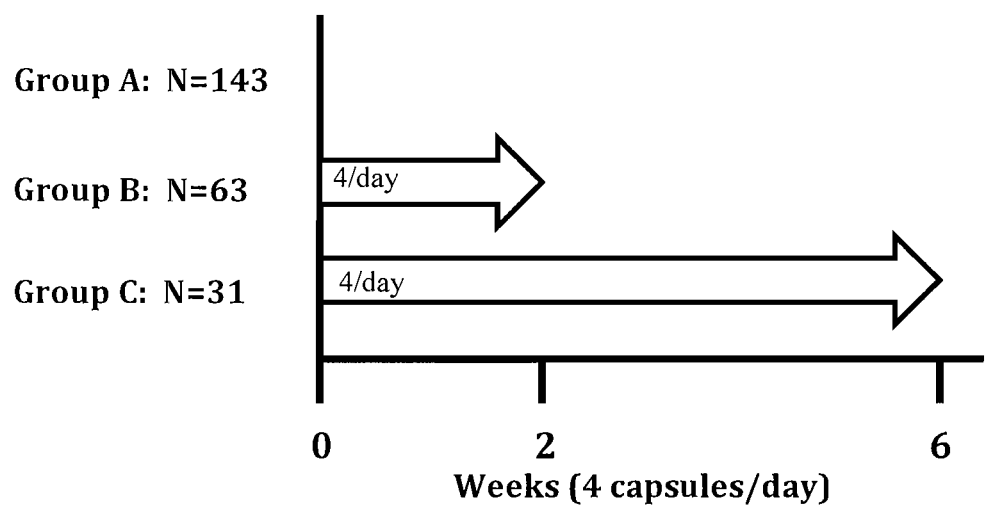
FIG. 1 illustrates the study design for the VASCAZEN™ open label study.

The present invention provides a combination therapy and a method for its use which contains novel combinations of selected mixtures of one or more cholesterol absorption inhibitors with an omega 3 fatty acid formulation.

The methods are useful in the treatment of patients with hypertriglyceridemia, hypercholesterolemia, mixed dyslipidemia, atherosclerotic disease, cardiovascular disease (CVD) and vascular disease.

The oral administration of these compositions acts to reduce serum cholesterol levels and blood pressure, increase HDL levels in proportion to LDL levels, to protect lipids from oxidation thereby preventing the formation of plaques which block coronary arteries, and to lower both triglyceride levels and homocysteine levels. In addition, it is believed that oral administration of the compositions of this invention acts to reduce the risk of stroke, as well as heart attack, in human adults.

One particularly desirable embodiment of the invention is directed toward a composition and a method for its use including a cholesterol absorption inhibitor, which is exemplified by, albeit not limited to an ezetimibe marketed under such tradenames as EZEDOC, EZEE, EZET, EZETIB, EZZI-CARD, LIPEZET, ZETICA, EZTA, EZIBLOC, or pharmaceutically acceptable salts thereof or a combination thereof; and an omega-3 fatty acid formulation.

With respect to the omega-3 component of the combination therapy and method of its use, the present invention provides a long chain fatty acid composition that includes a formulation containing a minimum of about 90% omega 3 fatty acids by weight having a combination of Eicosapentaenoic acid (EPA) and Docosahexaenoic acid (DHA) in a weight ratio of EPA:DHA of from 5.7 to 6.3, wherein the sum of the EPA, DHA and DPA is about 82% by weight of the total formulation and about 92% of the total omega 3 fatty acid content of the composition. EPA+DHA are about 80% of the total formulation and about 89% of the total omega 3 fatty acid content of the composition. The fatty acids of the present invention are understood to include biologically active glyceride forms, e.g. triglycerides, biologically active ester forms, e.g. ethyl ester forms, and biologically active phospholipid forms, their derivatives, conjugates, precursors, and pharmaceutically acceptable salts and mixtures thereof.

The pharmaceutical formulation of the instant invention is contemplated as being administered in amounts providing a daily dosage of 1 to 4 gm of said formulation. The pharmaceutical formulation at such dosage level being effective for the treatment or prophylaxis of risk factors of cardiovascular disease and the protection against sudden death in patients with CVD.

Pharmaceutical formulations of the instant invention may be provided wherein a unit form is a gel or liquid capsule.

An exemplary unit dosage form includes from about 645 to about 715 mg/gm EPA, for example about 680 mg/gm EPA and from about 105 to 115 mg/gm, for example about 110 mg/gm DHA. The unit dosage can include from about 22 to about 28 mg/gm DPA for example about 25 mg/gm DPA. Unit doses may additionally include a stabilizer, e.g. tocopherol in amounts up to about 0.5%, for example about 0.15% to about 0.25% or about 0.2% by weight. The effective unit dosage is generally 3 gm to 4 gm of the pharmaceutical formulation which are provided daily to CVD patients in one or more unit doses, for example about 3-4 one gram capsules per day. As set forth below, one or more optional ingredients can be included in the formulations. Such ingredients may be separately added or may be components of the source from which the omega 3 fatty acids in the formulation are derived.

In some embodiments, the formulation may further contain about 30 mg/gm of arachidonic acid (AA). In some embodiments, the formulation may further contain up to about 5%, for example about 3% or about 30 mg/gm of arachidonic acid (AA). It has been discovered that aspirin-acetylated COX-2 is also able to convert Omega-6 AA through lipoxygenases (LOX) to lipoxins (LXs), which are potent anti-inflammatory mediators (Nature Chemical Biology, Vol. 6, June 2010, Pp 401-402).

Some embodiments of the formulation contains >2%, for example >3%, of 18 carbon Omega-3 fatty acids, either individually or in total. Exemplary 18 carbon atom omega-3 include alpha-linolenic acid (ALA) and Stearidonic acid (SDA), either alone or in combination. Studies have shown that the presence of 18 carbon Omega-3s, such as ALA elicit anti-inflammatory effects (Zhao et al, Am J Clin Nutr 2007; 85:385-91). The composition is formulated with a specific amount of DHA consisting of about 400 mg per daily dose.

The composition can contain additional fatty acids in lesser amounts, usually less than about 1% of each that is present. Exemplary embodiments contain about 0.3-0.7%, or about 5% of any of the additional fatty acids, These additional fatty acids can include, for example, omega-6 fatty acids such as Dihomo-gamma-linolenic acid (DGLA; 20:3n6), Docosapentaenoic acid (Osbond acid; 22:5n6); omega-9 fatty acids such as Oleic acid (18:1n9) and others such as 7,10,13,15-hexadecatetraenoic acid and (16:4n1), 9,12,15,17-octadecatetraenoic acid (18:4n1). Other fatty acids may be present in higher quantities. For example, Eicosatetraenoic acid (ETA; 20:4n3) may be present in amounts up to about 2%, for example about 1.5%, and Heneicosapentaenoic acid (HPA; 21:5n3) may be present in amounts up to about 3%, for example at about 2.3%. These additional fatty acids may be added separately or may be present in formulations obtained from particular sources using particular methods. Other additional components and fatty acids may also be present in small amounts, for example 0-0.25% of the formulation.

The composition is formulated with a DHA content to provide about 400 mg per daily dose.

Daily administration of the formulation can reduce the level of triglycerides (TG) and increases high density phospholipids (HDL) levels, while lowering low density lipoprotein (LDL) levels in CVD patients.

A highly potent omega-3 formulation in accordance with the present invention is marketed by Pivotal Therapeutics, Inc., under the trade name VASCAZEN™, to alleviate the cardiovascular risks associated with omega-3 deficiency. VASCAZEN™, has been formulated for the dietary management of omega-3 deficiency in patients with CVD, providing EPA and DHA to levels not attainable through normal dietary modifications. More specifically, the VASCAZEN™ product exemplifies the present invention in being composed of about 90% or more omega-3 fatty acids at a ratio of eicosapentaenoic acid (EPA) to docosahexaenoic acid (DHA) within the range of 5.7:1-6.3:1, respectively. The formulation contains about 680 mg/g of EPA, about 110 mg/g of DHA, and about 25 mg/g of DPA per capsule. Each capsule has a total weight of about 1000 mg. It is generally contemplated that a daily regimen of VASCAZEN™ includes 4 tablets per day given either in one dose or in separate doses throughout the day. With respect to a 1000 mg fill, the formulation contains at least about 90% or more omega-3 fatty acids, wherein about 80% is the sum of EPA+DHA, and about 82% the sum of EPA+DPA+DHA. Embodiments can also contain about 30 mg/g of arachidonic acid, an omega-6 fatty acid, and/or >3% of 18 carbon Omega-3 fatty acids.

The present invention provides a novel composition, which may be incorporated into an orally administered formulation for the reduction of risk factors associated with CVD, and a novel treatment method. A composition of the formulation of the invention may be used orally to treat and/or prevent risk factors of CVD and stroke, including reduction of high blood pressure and improving overall lipid profiles, e.g. low density lipoprotein (LDL), high density lipoprotein (HDL) and triglycerides. While not wishing to be bound by theory, the inventors believe that the compositions work by acting at different sites and aspects of cardiovascular disease. The compositions of the present invention are preferably presented for administration to humans and animals in unit dosage forms, such as tablets, capsules, pills, powders, granules, and oral solutions or suspensions and the like, containing suitable quantities of an active ingredient.

The daily dose of formulated composition provides a strong anti-inflammatory and mood enhancing effect with a specific amount of DHA for the protection against sudden death in patients with CVD.

According to a US study, and the Dietary Guidelines Committee, 70% of Americans are omega-3 deficient due to lack of consumption of this essential nutrient in the typical "western diet", which includes an overabundance of pro-inflammatory omega-6 fatty acid intake, by comparison. In patients with CVD, this dietary trend can be particularly dangerous. Coupled with other cardiometabolic risk factors, omega-3 deficiency further exacerbates the chronic progression of this disease. A growing body of evidence has demonstrated the cardiovascular health risks associated with chronic omega-3 deficiency. A dietary deficiency of EPA acid and DHA in particular, allows for downward pro-inflammatory pressures created by the metabolism of arachidonic acid (AA) that is typically very high in the diets of most Americans. Overall, omega-3 fatty acid deficiency contributes to a pro-inflammatory state, the consequences of which include negative effects on cardiovascular health, including increased risk for development of dyslipidemia (high cholesterol, high triglycerides), atherosclerotic plaque buildup, hypertension, and cardiac arrhythmia.

Chronic omega-3 deficiency can subsequently lead to increased risk for suffering a fatal heart attack. Maintenance of blood levels of EPA, DHA and DPA above 6.1% of total blood fatty acids, compared to levels between 2.1%-4.3% is associated with an 80.0% lower risk of sudden cardiac death. To counterbalance the cardiovascular risks associated with an overabundance of AA, and the pro-inflammatory influences upon this metabolic pathway, one would need to increase EPA and DHA consumption to levels that can not be attained through dietary changes alone. Filling the "omega-3 nutritional void" thus requires additional supplementation with a highly potent EPA and DHA formulation, which provides high levels of EPA, as well as DHA, for full clinical benefit, removing a key risk factor in patients with CVD.

Example

In order to determine the presence of synergy attributable to the ingestion of a combined therapy including the novel omega-3 fatty acid composition of the present invention and a cholesterol absorption inhibiting pharmacologically active ingredient, the following experimental protocol will be carried out.

All patients will undergo drug therapy as required to treat their clinical symptoms including the use of other classes of cholesterol-lowering drugs like statins (that will not interfere with intestinal cholesterol levels).

One group of patients will be those who in addition to their existing drug therapy are prescribed VASCAZEN™ following a protocol as set forth in the Open Label trial discussed herein, in combination with ezetimibe to lower circulating cholesterol concentrations.

A second group of patients will be those who are not prescribed ezetimibe as part of their normal course of therapy, but are prescribed VASCAZEN™.

A third group will be prescribed ezetimibe alone, with no VASCAZEN™ therapy.

Blood samples will be taken from all patients at the study baseline. All patients will be fasting for 12 hours prior to the blood sample being taken. After 6 weeks a second blood sample will be taken. This will determine if the drug intervention of ezetimibe alone, VASCAZEN™ alone or a combination of ezetimibe and VASCAZEN™ influenced the circulating cholesterol concentration.

In the previously conducted open label study to analyze the safety and efficacy of VASCAZEN™, whole blood omega-3 fatty acid levels were examined in 143 patients, and the inventive formulation was administered to patients for two or six-week follow-ups, providing about 2800 mg/day EPA and about 480 mg/day DHA. The primary outcome measure was the change in the sum of blood EPA+DHA+DPA. levels (the Omega-Score™), expressed as a percentage of total blood fatty acid levels over a two or six-week duration.

The normalized baseline Omega-Score™ was 3.4% (N=143). In the two-week and six-week treated groups, the inventive formulation increased Omega-Score™ levels by 52.8% (N=63, p=<0.0001) and 120.6% (N=31, p=<0.0001) respectively, compared to baseline levels measured in each group. After six weeks of intervention, maximal, and stable levels were maintained at an average score of 7.5%. The formulation in accordance with the present invention was generally well tolerated, with only minor adverse events reported in a small proportion of study participants. (See Table 4)

Methodology:

The 6-week open label study was conducted at a single site in Canada. Subjects were eligible for the study if they met all inclusion and exclusion criteria set out in the clinical study protocol. All eligible subjects provided informed consent prior study enrollment, and entered Group A (FIG. 1.). Sixty three subjects were provided 4 capsules per day of VASCAZEN™ (Group B), an oral dose of 2720 mg EPA and 440 mg DHA per day. After two weeks of treatment, whole blood omega-3 blood level was assessed, and 31 subjects entered into Group C, for continued treatment. Group C subjects provided whole blood samples at weeks 4 and week 6, for follow-up Omega-Score™ assessment.

The primary outcome measure was the change in Omega-Score™ values expressed as a percentage of total blood fatty acid levels over a 2-week period for Group B, and 6-week period for Group C. The baseline Omega-Score™ value for Group A was calculated as the mean percentage at week 0, prior to VASCAZEN™ intervention, and Groups B and C Omega-Score™ means were evaluated at the specified time points accordingly.

The study included both men and women >15 years of age, in stable medical condition. Exclusion criteria included the following: A history of ventricular arrhythmia, known bleeding or clotting disorder, liver or kidney disease, autoimmune disorder or suppressed immune systems, seizure disorder or taking anticonvulsant medication; allergies to fish; or subjects with an implantable cardioverter defibrillator. Medical histories, and current medications were also documented.

Laboratory analysis of total blood fatty acids in whole blood was conducted by a central laboratory, (University Health Network Laboratory, Toronto, Ontario), accredited by the College of American Pathologists' Laboratory Accreditation Program. Analysis was carried out by derivatizing fatty acids into methyl esters followed by Gas Chromatography-Mass Spectrometry (GC-MS) analysis (Agilent Technologies 6890N series gas chromatograph, 5975C detector, Mississauga, Ontario). Fatty acids were extracted from 200 µL of whole blood sample using a mixture of methanol and chloroform. Fatty acids were then methylated with 10% (w/v) $BCl_3$ in methanol by incubation at 90° C. for 25 min to form fatty acid methyl esters (FAMEs). After cooling the FAMEs were extracted with water/hexane mixture and 1 uL of n-hexane extract was injected for GC-MS analysis.

Sample size was justified accordingly. Assuming a mean baseline level of blood Omega-Score™ levels of at least 3.0% and a standard deviation in change of blood Omega-Score™ levels of 1.8% in the study population, the minimum sample size of 63 study subjects would result in a minimum power of 90.2% to detect an increase in blood Omega-Score™ levels following 2 weeks of study intervention of at least 25.0% relative to baseline, at a significance level of $\alpha=0.05$. The minimum sample size of 30 subjects taking VASCAZEN™ for six weeks would result in a minimum power of 94.2% to detect an increase in blood Omega-Score™ levels following 6 weeks of study intervention of at least 40.0% relative to baseline, at a significance level of $\alpha=0.05$. The safety population was defined as a patient group that had a minimum of 2 weeks and maximum of 6 weeks VASCAZEN™, at a dose of 4 capsules per day. Primary analyses of treatment efficacy was performed on the subset of enrolled study subjects for whom blood measurements were taken at baseline and after 2 weeks of study treatment. The change in blood Omega-Score™ levels over the 2-week period (expressed as a percentage change from baseline) was computed for each study subject. The distribution of changes in blood Omega-Score™ levels over 2 weeks were tested for normality using the Pearson-D'Agostino test. A paired t-test was conducted in order to test the change in blood Omega-Score™ levels over the 2-week period.

Secondary analyses of treatment efficacy was performed on the subset of enrolled study subjects for whom blood Omega-Score™ levels were taken at baseline and at time points of 2 weeks, 4 weeks and 6 weeks following baseline. An analysis of variance (ANOVA), utilizing subjects as blocks, was conducted to test the change in blood OmegaScore™ levels between any pair of time points over the 6-week period; multiple comparisons were conducted at a family-wide significance level of α=0.05 in order to determine which pairs of time points (if any) differ significantly in terms of mean blood EPA+DHA+DPA levels. A linear contrast was carried out in order to test the hypothesis that mean blood EPA+DHA+DPA levels increase linearly within this subset of study subjects over the 6-week period.

Results:

Baseline characteristics of each study group are outlined in Table 1. Across all groups, age demographics were comparable, with the majority of study participants being middle-aged. Within group A, the mean age of the total group (N=143), consisting of mostly males (74.1%), was 50.9 years, and similar age distributions were observed between men (52.1), and women (46.9). Group B (N=63, 74.2% men), the two-week treatment group, had a mean age of 53.7, with comparable mean ages between men (55.8) and women (47.9). Finally, study subjects within group C(N=31, 87% men) had a mean age of 55.0 years (men, 54.0; women, 61.5). Baseline OmegaScore™ values were measured and all three groups, including men and women were found to have comparable, omega-3 deficient (defined as less than 6.1% Omega-Score) (N Engl J Med, Vol. 346, No. 15, Apr. 11, 2002, Pp. 1113-1118), scores between 3.3% and 3.8%.

TABLE 1

Baseline Characteristics*:

| | Group A | | |
|---|---|---|---|
| Characteristic | Men (N = 106) | Women (N = 37) | Total (N = 143) |
| Age, mean (SD) (years) | 52.1 ± 13.6 | 46.9 ± 15.0 | 50.9 ± 14.6 |
| *Omega-Score ™(%) | | | |
| Mean | 3.4 ± 1.4 | 3.5 ± 1.2 | 3.4 ± 1.3 |
| 95% CI | 3.2 to 3.7 (±1.1 to 1.6) | 3.2 to 3.7 (±1.0 to 1.4) | 3.2 to 3.6 (±1.1 to 1.6) |
| | Group B | | |
| Characteristic | Men (N = 47) | Women (N = 16) | Total (N = 63) |
| Age, mean (SD) (years) | 55.8 ± 10.9 | 47.9 ± 16.7 | 53.7 ± 13.1 |
| *Omega-Score ™(%) | | | |
| Mean | 3.8 ± 1.4 | 3.3 ± 1.3 | 3.6 ± 1.3 |
| 95% CI | 3.4 to 4.1 (±1.0 to 1.8) | 2.9 to 3.7 (±0.9 to 1.7) | 3.2 to 3.9 (±1.0 to 1.7) |
| | Group C | | |
| Characteristic | Men (N = 27) | Women (N = 4) | Total (N = 31) |
| Age, mean (SD) (years) | 54.0 ± 8.7 | 61.5 ± 11.0 | 55.0 ± 9.2 |
| *Omega-Score ™(%) | | | |
| Mean | 3.7 ± 1.2 | N/A | 3.4 ± 1.2 |
| 95% CI | 3.3 to 4.0 (±0.8 to 1.5) | N/A | 3.1 to 3.7 (±0.8 to 1.5) |

Omega-Score ™ calculated as the mean +/− SD (where N = number of subjects) from a normal distribution of raw data. Group C (women) did not have sufficient numbers to fit a normal distribution curve. The mean baseline score of the raw data for this group was 2.98%.

Figure 2:
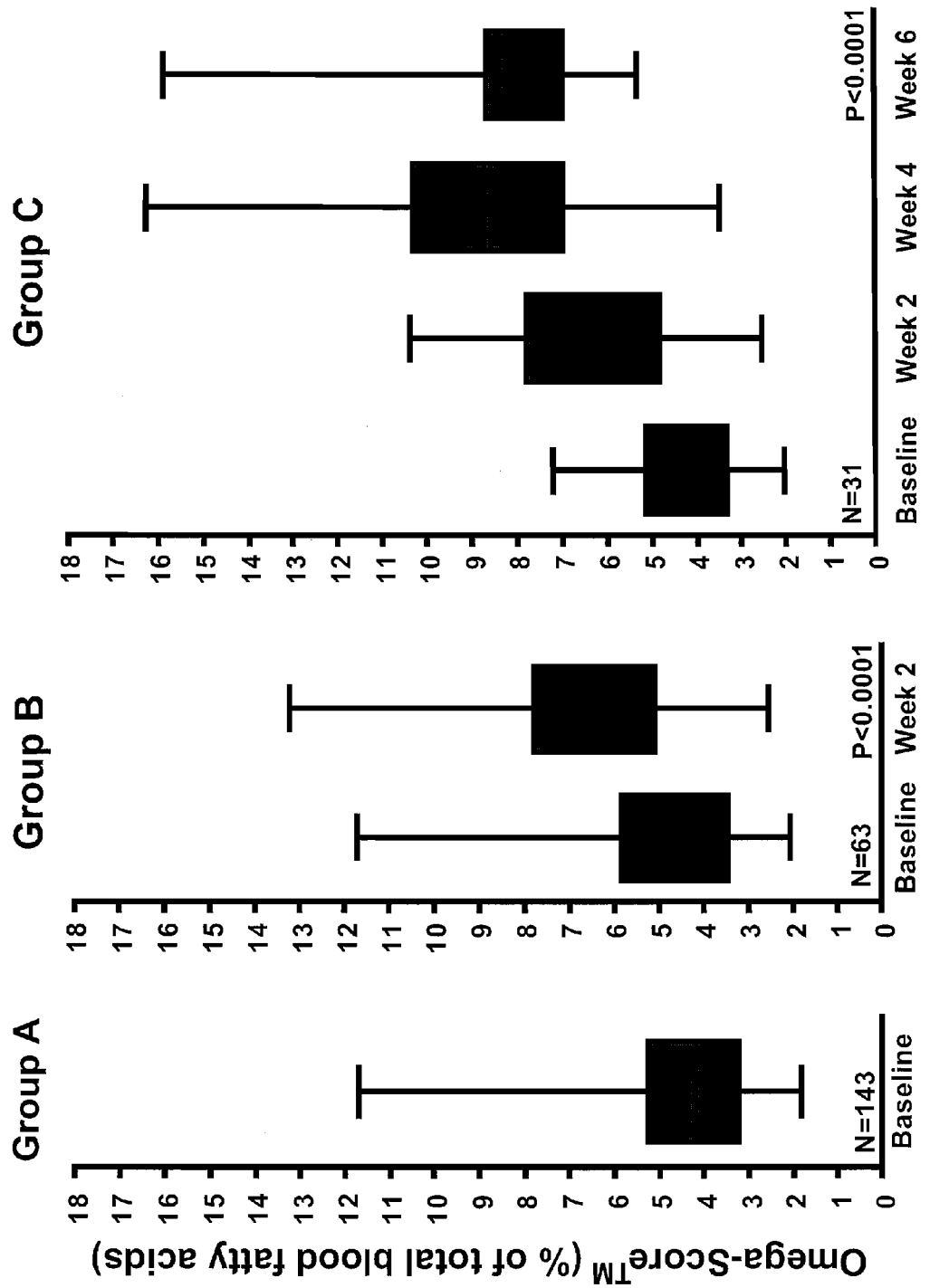
FIG. 2 is a plot of improved whole blood EPA+DHA+DPA levels baseline to week 6.
Figure 3:
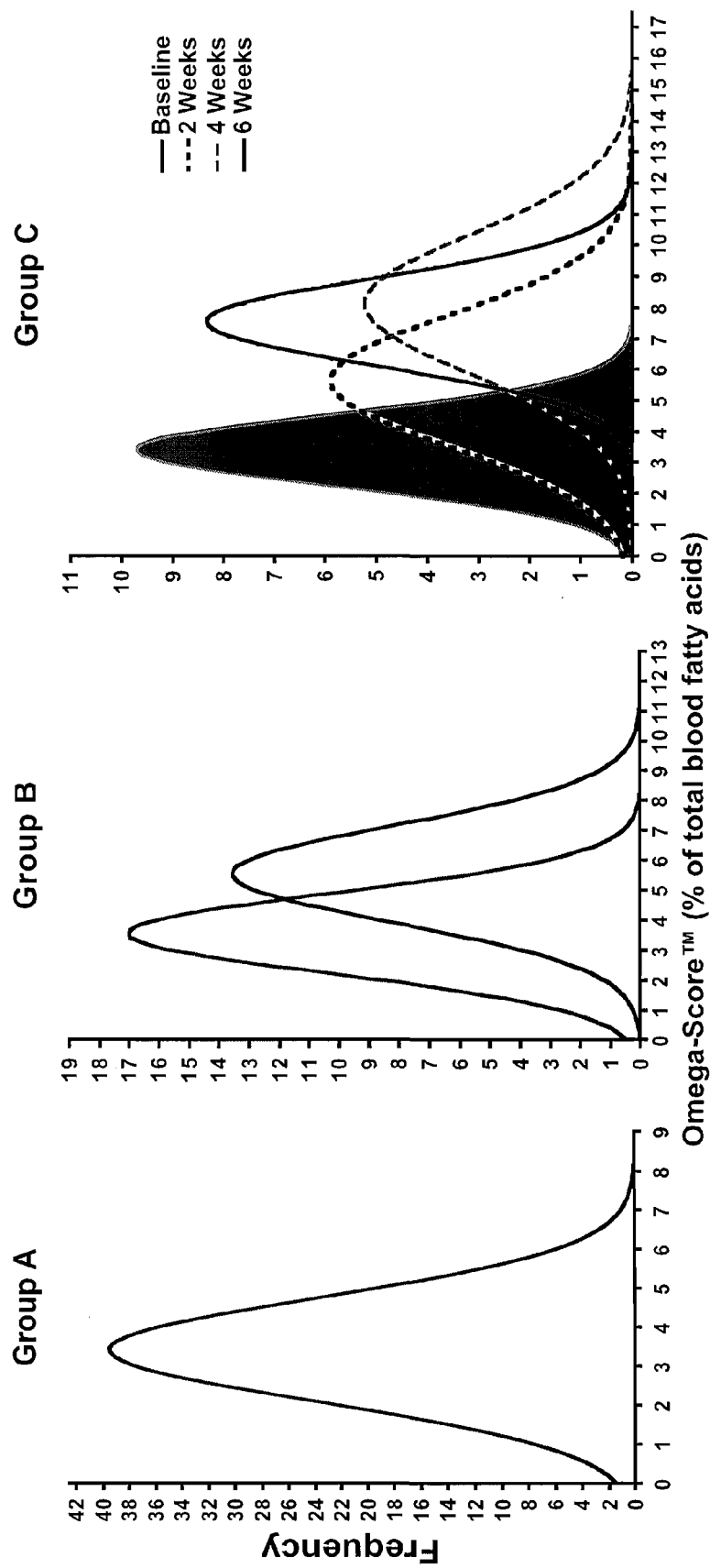
FIG. 3 illustrates the normal distribution curves for Groups A-C during the Open Label Study.

Results of the primary outcome measure are illustrated in FIG. 2 and Table 2, and calculated/fit to a normal distribution in FIG. 3, Table 3. Baseline levels of whole blood omega-3 blood levels revealed an omega-3 deficiency (group A) in a large study group (N=143). Within this group, subjects had a mean score of 4.4%, or 3.4% (normal distribution curve fit), representing 84.5% of individuals with scores below a 6.1% score cutoff, cardiovascular disease risk quartile. Study participants that received VASCAZEN™ intervention for 2 weeks (group B) had a significant (P<0.0001) improvement in their scores (FIG. 2, Table 2), with mean values improving from 3.6% to 5.5% (FIG. 3, Table 3), a 52.8% score increase. Over two weeks of intervention, study participants considered "at risk" were reduced from 80.6% to 46.8% (Table 3). Over the course of 6 weeks VASCAZEN™ intervention, group C subjects had significant mean score improvements (P<0.0001) (FIG. 2, Table 2), with mean values improving from 3.4% to 7.5% between baseline and week 6 (FIG. 3, Table 3), and representing a 120.6% increase in whole blood levels of EPA+DHA+DPA Omega-Score™ values. After 6 weeks of VASCAZEN™ intervention, 13.2% of participants remained at higher risk (<6.1% Omega-Score™), Table 3.

TABLE 2

Table 2. Primary Outcome Measure: Change in the sum of blood EPA + DHA + DPA levels expressed as a percentage of total blood fatty acid levels over a two or six-week intervention

| | Omega-Score ™ Mean ± SD (%) (% change from baseline) |
|---|---|
| Group A (N = 143) | |
| Baseline | 4.4 ± 1.7 |
| Group B (N = 63) | |
| Baseline | 4.7 ± 1.9 |
| Week 2 | 6.7 ± 1.9 (52.8%) |
| Group C (N = 31) | |
| Baseline | 4.3 ± 1.5 |
| Week 2 | 6.4 ± 2.1 (48.8%) |
| Week 4 | 8.6 ± 2.4 (100.0%) |
| Week 6 | 8.2 ± 2.0 (90.7%) |

TABLE 3

Table 3. Primary Outcome Measure: Change in the sum of blood EPA + DHA + DPA levels expressed as a percentage of total blood fatty acid levels over a two or six-week intervention, and represented as a normal distribution.

| | Omega-Score ™ (%) | | |
|---|---|---|---|
| | Mean ± SD (% change from baseline) | 95% CI | % of Patients At Risk (<6.1% Omega-Score ™) |
| Group A (N = 143) | | | |
| Baseline | 3.4 ± 1.3 | 3.1 to 3.7 (±0.9 to 1.4) | 84.5% |
| Group B (N = 63) | | | |
| Baseline | 3.6 ± 1.3 | 3.2 to 3.9 (±1.0 to 1.7) | 80.6% |
| Week 2 | 5.5 ± 1.6 (52.8%) | 5.1 to 6.0 (±1.2 to 2.1) | 46.8% (−33.8%) |
| Group C (N = 31) | | | |
| Baseline | 3.4 ± 1.3 | 3.1 to 3.7 (±0.9 to 1.4) | 84.5% |
| Week 2 | 5.7 ± 1.9 (67.6%) | 5.4 to 6.3 (±1.4 to 2.3) | 43.2% (−41.3%) |
| Week 4 | 7.9 ± 2.4 (132.4%) | 6.6 to 9.1 (±1.2 to 3.7) | 15.0% (−69.5%) |

TABLE 3-continued

Table 3. Primary Outcome Measure: Change in the sum of blood EPA + DHA + DPA levels expressed as a percentage of total blood fatty acid levels over a two or six-week intervention, and represented as a normal distribution.

| | Omega-Score ™ (%) | | |
|---|---|---|---|
| | Mean ± SD (% change from baseline) | 95% CI | % of Patients At Risk (<6.1% Omega-Score ™) |
| Week 6 | 7.5 ± 1.2 (120.6%) | 7.0 to 8.0 (±0.7 to 1.7) | 13.2% (−71.3%) |

Patients with >6.1% (ideal) scores had an 80% less chance of death from sudden cardiac arrest, compared to individuals in the 2.1%-4.3% risk quartile (score) range. In this study, the mean baseline value of the study population indicated that 84.5% of study participants, many of which with cardiovascular health issues, on statin, and/or blood pressure medication, had scores less than 6.1%, leaving themselves at greater risk for adverse events, especially in patients with known dyslipidemia, type 2 diabetes, and/or hypertension. After six weeks of VASCAZEN™ intervention, 71.3% of group C participants with previous baseline scores less than 6.1% were able to increase their score to a level above this threshold.

TABLE 4

| Adverse Event Description | 2-6 Weeks Treatment (N = 63) | Severity | Relationship to Study Treatment |
|---|---|---|---|
| Reflux/Aftertaste | 2 | Mild | Definite |
| Minor Leg Bruising | 1 | Mild | Unrelated* |

*Minor bruising appeared after two weeks of treatment and disappeared within 3 days. The subject continued taking VASCAZEN ™ for additional four week without any adverse event.

Group B study participant scores significantly increased (P<0.0001) by 52.8% from 3.6% to 5.5%. With prolonged VASCAZEN™ intervention, group C individuals had significant score improvement over the course of 6 weeks (P<0.0001, ANOVA), with similar improvements as the group B individuals within two weeks. After 4 weeks, VASCAZEN™ significantly (P<0.0001) increased mean scores from 3.4% to 7.9%, representing a 132.4% improvement, bringing the mean score of the total population to well within the >6.1% low risk quartile. Indeed, only 15% of study participants remained below this benchmark level after 4 weeks, a level that is sustained in the study group through 6 weeks of VASCAZEN™ intervention. VASCAZEN™ was generally well tolerated with a low incidence, of minor adverse events that are typical for omega-3 polyunsaturated fatty acid ethyl esters. This study has highlighted the prevalence of chronic omega-3 deficiency in the majority of people (84%), both men and women.

The consequences of omega-3 deficiency in patients with CVD are well documented, with numerous studies linking EPA and DHA deficiency. Many studies and current therapeutic approaches have categorized omega-3 as a therapeutic agent for the treatment of symptoms that accompany CVD. Unfortunately the common thread of thought around omega-3 fatty acid therapy does not lead to optimal results. EPA and DHA should not be considered therapeutic agents, rather, they should be considered essential nutrients, which should ideally be consumed regularly as part of a healthy balanced diet. Omega-3 deficiency in patients with CVD adds unnecessary risks, that can be avoided with suitable omega-3 supplementation. The present invention as exemplified by VASCAZEN™ intervention provides essential balanced levels of EPA and DHA that are difficult for many CVD patients to incorporate into their daily diet through food alone. In the typical western diet, the average American consumes 15 times less omega-3 fatty acids from fish than what is required to attain and maintain clinically beneficial levels of EPA and DHA. In order to consume enough of this essential nutrient to provide the daily dose that the present invention can provide, one would have to eat fish every single day, for more than one meal per day. This is unrealistic for most people.

The present study has demonstrated that maintenance of EPA+DHA+DPA to levels >6.1% can be achieved with the present invention within 4 weeks of intervention, and that over 85% of patients can achieve these levels at a dose of 4 capsules per day, supplying about 2720 mg EPA and 440 mg DHA. These findings support the use of omega-3 fatty acid supplements according to the present invention for the maintenance of routinely measured (via Omega-Score™ assessment), clinically beneficial EPA+DHA+DPA blood levels in patients with CVD.

Sustained Vasodilatory Effect:

In addition to the benefits outlined above with respect to omega-3 supplementation for an omega-3 deficient patient population, formulations according to the invention have been shown to provide a sustainable eNOS vasodilatory effect, defined as a vasodilatory effect persisting for 6 hours or more, which has heretofore not been achievable with either prescription or OTC grade omega-3 supplements.

To understand this vasodilatory effect in the context of treatment and prevention of cardiovascular disease, it is first necessary to understand the mechanism of vasodilation via the endothelium lining of blood vessels.

The following list of Abbreviations will be relied upon for the following discussion.

ABBREVIATION LIST

| Abbreviation | Signification |
|---|---|
| $[Ca^{2+}]$ i | Intracellular free calcium concentration |
| APA | Apamin |
| CaM | Calmodulin |
| CaMK-2 | Calmodulin kinase-2 |
| cAMP | Cyclic adenosine 3': 5' monophosphate |
| cGMP | Cyclic guanosine 3': 5' monophosphate |
| EDHF | Endothelium-derived hyperpolarizing factor |
| eNOS | Endothelial NO synthase |
| ET-1 | Endothelin-1 |
| $H_2O_2$ | Hydrogen peroxide |
| IKCa | Calcium-dependent Intermediate conductance Potassium Channels |
| Indo | Indomethacin |
| L-NA | N-ω-nitro-L-arginine |
| MnTMPyP | Mn (III) tetrakis (1-methyl-4-pyridyl) porphyrin |
| NO | Nitric oxide |
| $O_2^{\circ}-$ | Superoxide anion |
| PEG-Catalase | Polyethylene glycol-catalase |
| $PGI_2$ | Prostacyclin I2 |
| PI3-K | Phosphoinositide-3 kinase |
| PKC | Protein kinase C |
| PP2 | 4-amino-5-(4-chlorophenyl)-7-(t-butyl) pyrazolo [3,4] pyrimidine |
| ROS | Reactive oxygen species (Reactive Oxygen Species) |
| sGC | Soluble guanylyl cyclase |
| SKCa | $Ca^{2+}$-dependent small conductance potassium channels |
| SOD | Conductance Superoxide dismutase |
| TRAM34 | 1-[(2-Chlorophenyl) diphenylmethyl]-1H-pyrazole |

-continued

| Abbreviation | Signification |
| --- | --- |
| TX$_{A2}$ | Thromboxane A2 |
| U46619 | 9,11-dideoxy-9-prostaglandin F2 methanoepoxy |

The endothelium consists of a single endothelial cell layer lining the luminal surface of all blood vessels. Endothelial cells play an important function in the regulation of vascular homeostasis. They regulate the contact of blood with the underlying thrombogenic arterial wall. They respond to numerous physiological stimuli such as circulating hormones and shear stress by releasing several short-lived potent endothelium-derived vasoactive factors such as nitric oxide (NO) and endothelium-derived hyperpolarizing factor (EDHF), these two factors playing a major role in the control of vascular tone (Busse et al., 2002; Michel and Feron, 1997). In addition, endothelial cells can also generate prostacyclin (PGI$_2$), a prostanoid causing relaxation of some blood vessels.

Endothelium-Derived Nitric Oxide (NO):

NO is produced by endothelial nitric oxide synthase (eNOS) from L-arginine, NO plays critical roles in normal vascular biology and pathophysiology. NO induces relaxation of the vascular smooth muscle by activating soluble guanylyl cyclase resulting in the formation of cyclic guanosine 3'-5' monophosphate (cGMP). In addition to the regulation of vascular tone and inhibition of platelet aggregation, NO also inhibits many key steps involved in atherogenesis including vascular smooth muscle cell proliferation, monocyte adhesion (Dimmeler et al., 1997; Hermann et al., 1997; Tsao et al., 1996) and cell death. eNOS can be activated by receptor-dependent and -independent agonists as a consequence of an increase in the intracelluar concentration of free Ca ([Ca$^{2+}$]i) and the association of a Ca$^{2+}$/calmodulin (CaM) complex with eNOS leading to its activation (Fleming et al., 2001). Indeed both the agonist-induced NO formation and subsequent vasorelaxation are abolished by the removal of Ca$^{2+}$ from the extracellular space as well as by CaM antagonists. eNOS is also regulated in endothelial cells at a post-translational level primarily through protein/protein interactions and multisite phosphorylation at Ser116, Thr497, Ser635, and Ser1179 (residue numbers are for the bovine sequence, equivalent to Ser114, Thr495, Ser633, and Ser1177 in the human sequence (Bauer et al., 2003; Boo et al., 2002; Dimmeler et al., 1997). Indeed, eNOS has been shown to be regulated by the interaction with positive and negative protein modulators such as caveolin (Cav-1) and heat shock protein 90 (Garcia-Cardena et al., 1998; Ju et al., 1997; Pritchard et al., 2001). In the basal state, the majority of eNOS appears to be bound to caveolin-1 with its enzymatic activity being repressed in the caveolae (Michel et al., 1997). This tonic inhibition of eNOS can be released by displacing caveolin-1 with Ca$^{2+}$/CaM in response to Ca$^{2+}$ mobilizing agonists (Ju et al., 1997). In addition to these modulators, phosphorylation of eNOS at key regulatory sites plays an important role in the regulation of enzyme activity in response to several physiological stimuli (Ju et al., 1997). It has been shown that phosphorylation of eNOS at Ser1179 is associated with increased enzyme activity (Gallis et al., 1999; McCabe et al., 2000). Phosphorylation of eNOS-Ser1179 is regulated by PI3-kinase-dependent mechanisms (Gallis et al., 1999). Akt, one of the major regulatory targets of PI3-kinase, has been shown to directly phosphorylate eNOS at Ser1179 and activate the enzyme in response to vascular endothelial growth factor (VEGF), sphingosine-1-phosphate, and estrogens (Dimmeler et al., 1997; Fulton et al., 1999). However, eNOS-Ser1179 can also be phosphorylated by AMP-activated protein kinase (Busse et al., 2002), protein kinase A (PKA), and protein kinase G (PKG). Exactly which protein kinase(s) phosphorylates eNOS-Ser1179 in intact cells appears to be dependent on the type of endothelial cells and stimuli. For example, shear stress phosphorylates eNOS Ser1179 by a PI3-kinase- and PKA-dependent manner without involving Akt whereas EGF phosphorylates eNOS Ser1179 by a PI3-kinase- and Akt-dependent manner (Boo et al., 2002). In addition, the ischemia-reperfusion injury activates the PKA pathway leading to the phosphorylation of eNOS at Ser1179 and Ser635 (Li et al., 2010). In addition, the level of eNOS expression can be modulated by several factors including shear stress (Butt et al., 2000), hypoxia, low-density lipoproteins (LDL) (Chen et al., 2008; Chen et al., 1999) and oxidized fatty acids (Corson et al., 1996).

Endothelium-Derived Hyperpolarizing Factor (EDHF):

Endothelium-dependent vasorelaxation has also been observed in some blood vessels following inhibition of NO and PGI2 synthesis and has been attributed to endothelium-derived hyperpolarizing factor (EDHF). EDHF relaxes blood vessels through hyperpolarization of the vascular smooth muscle. This effect will close voltage-operated Ca$^{2+}$ channels resulting in reduction of the intracellular free Ca$^{2+}$ level and subsequent relaxation of the vascular smooth muscle. Potassium (K$^+$) channels underlie the hyperpolarization induced by EDHF and involve intermediate conductance Ca$^{2+}$-activated K$^+$ (IKCa) channels and small conductance Ca$^{2+}$-activated K$^+$ (SKCa channels). In several disease conditions including the presence of cardiovascular risk factors, the endothelium undergoes functional and structural alterations and it loses its protective role, and becomes proatherosclerotic (Vanhoutte, 1989). The loss of the normal endothelial function is referred to as endothelial dysfunction, which is characterized by impaired NO bioavailability subsequent to a reduced generation of NO by eNOS and/or an increased breakdown of NO by reactive oxygen species (ROS) and, in particular, superoxide anions (Vanhoutte, 1989).

Previous studies by the present inventors have indicated that natural products such as Concord grape juice (Anselm et al., 2007) and red wine polyphenols (Ndiaye et al., 2005) activate the endothelial formation of NO by causing the redox-sensitiveSer/PI3-kinase/Akt pathway-dependent phosphorylation of eNOSat Ser1177.

Fish oil omega-3 is a rich source of EPA and DHA. Omega-3 fatty acids have been shown to cause endothelium-dependent vasorelaxation in vitro in rat aortic rings and coronary artery rings by stimulating the endothelial formation of NO (Engler et al., 2000; Omura et al., 2001). However, the signal transduction pathway leading to eNOS activation remains poorly studied. Moreover, little information is currently available regarding the optimal ratio of EPA:DHA for the activation of eNOS. Therefore, the following experiments were carried out to characterize the fish oil-induced activation of eNOS in isolated blood vessels and cultured endothelial cells.

The initial experiment was designed to determine the ability of omega-3 fatty acids (EPA, DHA and different ratios of EPA:DHA) to cause endothelium-dependent relaxations in rings of porcine coronary arteries, thereby enabling the characterization of the role of NO and EDHF in endothelium-dependent relaxation and identification of the signal transduction pathway involved.

Additional experiments were designed to determine the ability of omega-3 fatty acids (EPA, DHA and different ratios of EPA:DHA) to cause activation of eNOS in cultured endothelial cells and to determine the underlying signal transduction pathway.

In order to make the above determinations we designed an experiment to codify vascular reactivity. Initially, the left circumflex coronary artery harvested from fresh pig hearts is cleaned of its fat and adherent tissue and cut into rings 2 to 3 mm in length. Rings without endothelium were obtained mechanically by rubbing with a pair of pliers inserted into the vessel lumen. Rings with or without endothelium were suspended in organ baths containing Krebs bicarbonate solution (composition in mM: NaCl 118.0, KCl 4.7, $CaCl_2$ 2.5, $MgSO_4$ 1.2, $NaHCO_3$ 23.0; $KH_2PO_4$ 1.2 and glucose 11.0, pH 7.4, 37° C.) oxygenated with a mixture of 95% $O_2$ and 5% $CO_2$. After equilibrating rings for 90 min at a basal tension of 5 g, rings were contracted with KCl (80 mM) to verify the responsiveness of the vascular smooth muscle. After a 30 min washing period, the integrity of the endothelium was verified. Rings were contracted with U46619 (1-60 nM, an analogue of thromboxane A2) to 80% of the maximal contraction, and at the plateau of the contraction, bradykinin (0.3 μM) was added to check the presence of a functional endothelium. After repeated washings and return to baseline, rings were contracted again with U46619 before applying an increasing range of omega-3 fatty acids (0.001% to 0.4% v/v) to test their ability to induce relaxation of coronary artery rings. During the stabilization phase (30 min before contraction with U46619) different pharmacological tools were added to the Krebs bicarbonate solution to characterize the signaling pathway leading to endothelium-dependent relaxations:

a. Indomethacin (10 μM), an inhibitor of cyclooxygenases (COX) to prevent the formation of vasoactive prostanoids, particularly prostacyclin, b. Nω-nitro-L-arginine (L-NA, 300 μM), a competitive inhibitor of NO synthase (NOS) to overcome the NO component, and c. TRAM 34 (100 nM) and apamin (100 nM) inhibitors of $Ca^{2+}$-activated potassium channels (IKCa and SKCa) respectively, to overcome the EDHF component.

Pig coronary artery endothelial cells were harvested, cleaned with phosphate buffered saline solution (PBS) without calcium to remove any residual blood. Endothelial cells were isolated by collagenase (type I, Worthington, 1 mg/ml, 14 min at 37° C.) and cultured in medium MCDB131 (Invitrogen) supplemented with 15% v/v fetal calf serum, 2 mM glutamine, 100 U/mL penicillin, 100 U/mL streptomycin and 250 mg/ml fungizone (Sigma, St Louis, Mo.) at 37° C. in 5% $CO_2$. All experiments were performed with confluent endothelial cells used at first passage. Endothelial cells were exposed to MCDB131 with 0.1% v/v fetal calf serum 5 h before treatment with different substances.

After treatment, endothelial cells were rinsed twice with PBS and lysed with extraction buffer (composition in mM: Tris/HCl 20, pH 7.5 (QBiogene), NaCl 150, $Na_3VO_4$ 1, $Na_4P_2O_7$ 10, NaF 20, okadaic acid 0.01 (Sigma), protease inhibitors (Complete Roche) and 1% Triton X-100). 25 μg of total proteins were separated on SDS-polyacrylamide (Sigma 8%) at 100 V for 2 h. Separated proteins were transferred onto a polyvinylidene fluoride membrane (Amersham) by electrophoresis at 100 V for 2 h. The membranes were blocked with blocking buffer containing 3% bovine serum albumin in TBS-T (Tris-buffered saline solution, Biorad, containing 0.1% Tween 20, Sigma) for 1 h. For detection of proteins, membranes were incubated in TBS-T containing the respective primary antibodies (p-eNOS Ser 1177, p-eNOS Thr 495 and p-Akt Ser 473 (dilution 1:1000), β-tubulin (dilution 1:5000, Cell Signaling Technology) overnight at 4° C. After a washout period, the membranes were incubated with secondary antibodies (anti-rabbit for p-eNOS, p-Akt, and anti-mouse for β tubulin) coupled to horseradish peroxidase (Cell Signaling Technology, dilution 1:5000) at room temperature for 1 h. Stained protein markers (Invitrogen) were used for the determination of the molecular weight of separated proteins. Immunoreactive bands were detected using chemiluminescence (Amersham).

All results were presented as mean±standard error of mean (SEM). n indicates the number of different coronary arteries studied. Statistical analysis was performed using Student t test or analysis of variance (ANOVA) test followed by Bonferoni post-hoc test. A P value of <0.05 is considered statistically significant.

Figure 4:
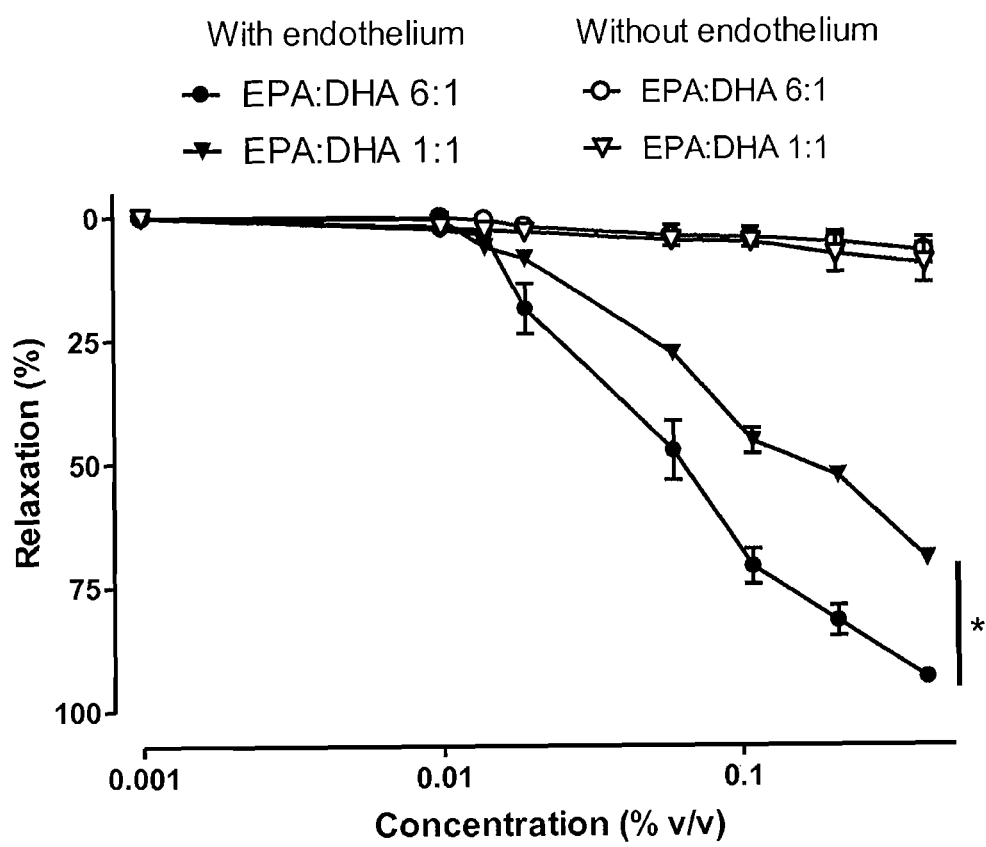
FIG. 4 illustrates the effect of differing EPA:DHA ratios on the relaxation of coronary artery rings with and without the presence of the endothelium.

Results:

The omega-3 fatty acid preparation EPA:DHA 1:1 induced concentration-dependent relaxations of coronary artery rings with endothelium whereas only small relaxations were obtained in those without endothelium contracted with U46619 (FIG. 4). The relaxations to EPA:DHA 1:1 was observed at volumes greater than 0.01% v/v and they reached about 75% at 0.4% v/v (FIG. 4). In addition, the omega-3 fatty acid preparation EPA:DHA 6:1 also induced endothelium-dependent relaxations which were more potent than those induced by EPA:DHA 1:1 (FIG. 4). Relaxations to EPA:DHA 6:1 started at 0.01% v/v and they reached about 98% at 0.4% v/v (FIG. 4). These findings indicate that the omega-3 fatty acid preparation EPA:DHA 6:1 is more effective to induce endothelium-dependent relaxations of coronary artery rings than the EPA:DHA 1:1 preparation. Thereafter, all subsequent experiments were performed with the omega-3 fatty acid preparation EPA:DHA 6:1.

It was determined that the omega-3 fatty acid preparation EPA:DHA 6:1 induces endothelium-dependent relaxations involving both NO and EDHF.

Figure 5:
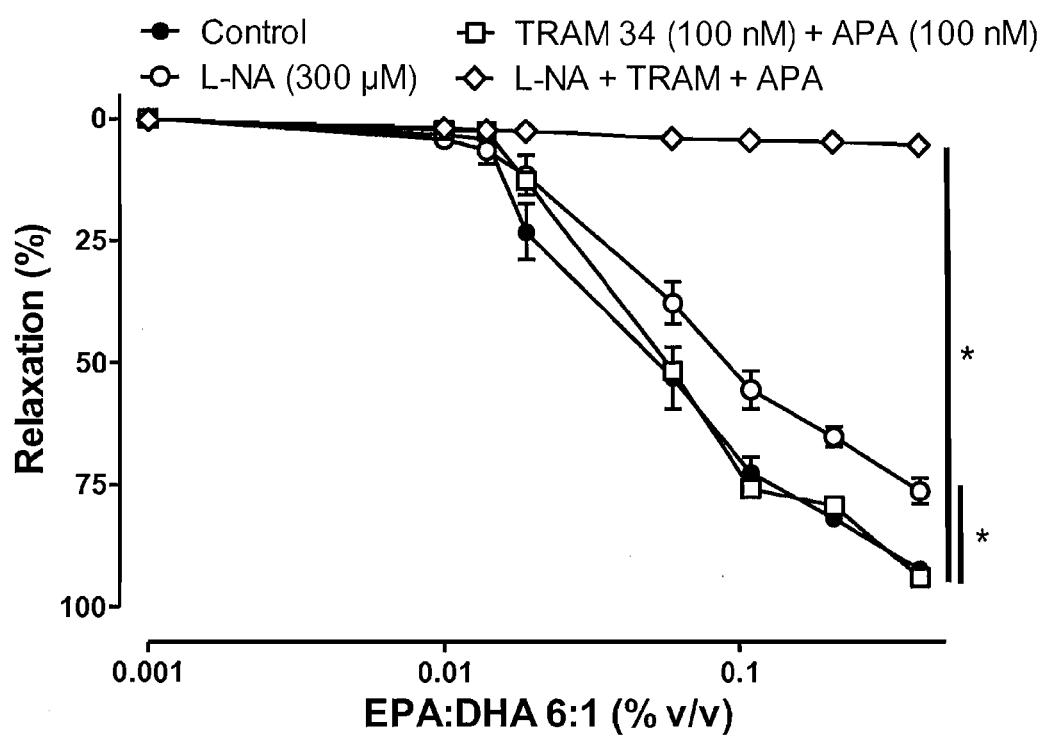
FIG. 5 discloses the relaxation effect of an EPA:DHA 6:1 control versus the effect of eNOS and EDHF inhibitors.

Previous studies have indicated that EPA and DHA induce relaxation of coronary artery rings by a mechanism mainly endothelium-dependent and sensitive to inhibitors of the formation of NO and EDHF (Omura et al., 2001). Therefore, a study to determine whether the endothelium-dependent relaxations induced by omega-3 fatty acid formulations having an EPA:DHA ratio of about 6:1 according to the present invention (referred to as EpA:DHA 6:1 herein) involve NO and EDHF was undertaken. The endothelium-dependent relaxation to EPA:DHA 6:1 was not significantly affected by inhibitors of the EDHF component, TRAM 34 and apamin (inhibitors of $Ca^{2+}$-dependent potassium channels of intermediate and low conductance IKCa and SKCa, respectively, FIG. 5). In contrast, relaxations were partially inhibited, but in a statistically significant amount, by L-NA (a competitive inhibitor of eNOS), indicating the involvement of NO (FIG. 5). In addition, the combination of L-NA plus TRAM 34 and apamin abolished the endothelium-dependent relaxation to EPA:DHA 6:1 (FIG. 5). Altogether, these findings indicate that EPA:DHA 6:1 induces endothelium-dependent relaxations which are mediated predominantly by NO and also, to a lesser extent, by EDHF.

Figure 6:
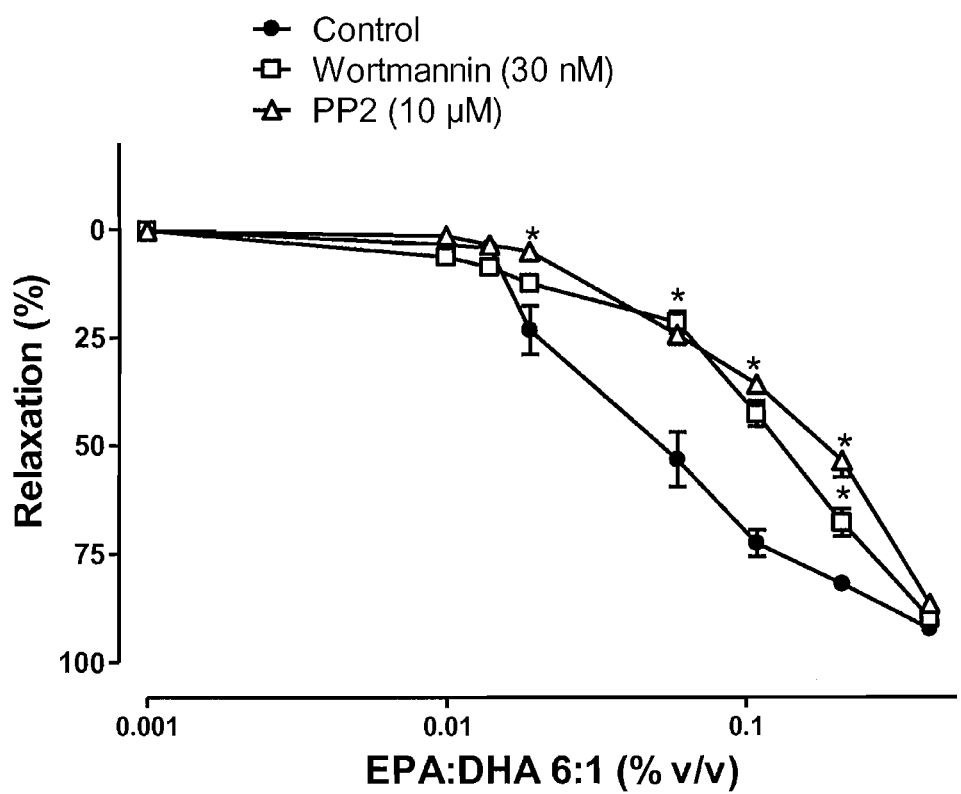
FIG. 6 discloses how the presence of Src kinase and PI3-kinase impacts the relaxation effect of an EPA:DHA 6:1 product.
Figure 7:
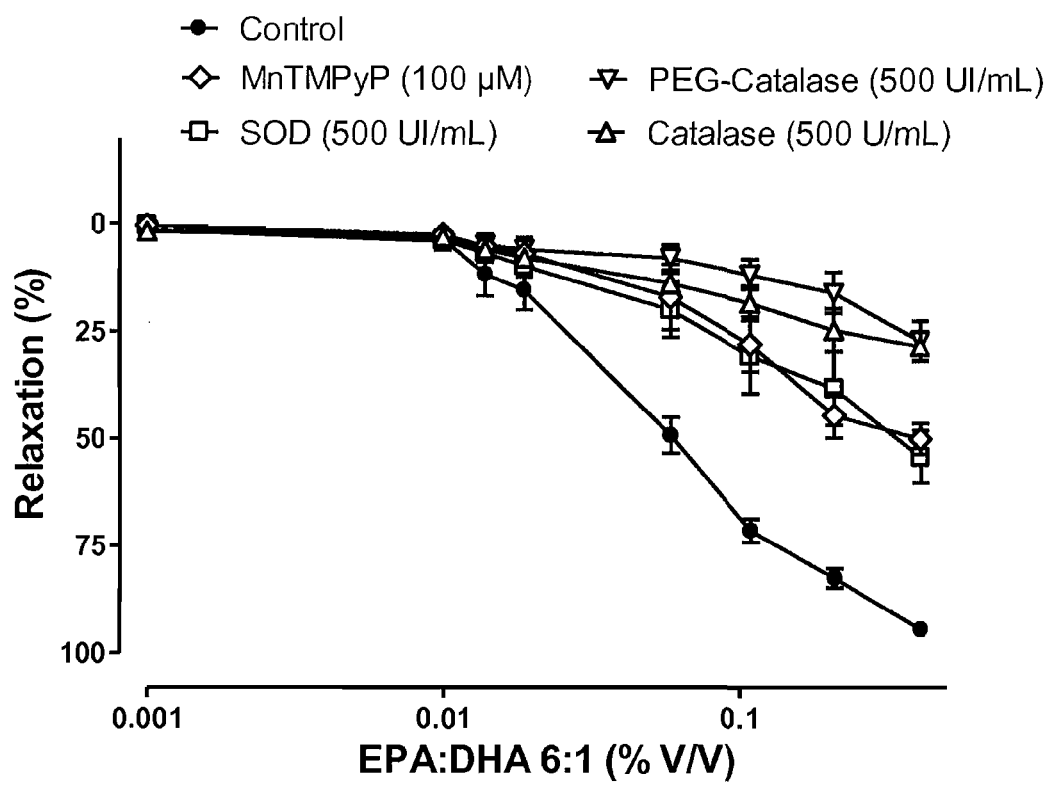
FIG. 7 illustrates the shift in relaxation effect of an EPA:DHA 6:1 product by membrane permeant analogues.

Several studies have shown that relaxations mediated by NO in response to polyphenols derived from grapes involve the redox-sensitive Src/PI3-kinase/Akt pathway (Anselm et al., 2007; Ndiaye et al., 2005). Therefore, it was decided to determine whether this pathway is involved in NO-mediated relaxations to EPA:DHA 6:1. In order to selectively study the NO component, all experiments were conducted in the presence of inhibitors of the EDHF component (Apamin+TRAM 34) and the formation of vasoactive prostanoids (indomethacin). The relaxation induced by EPA:DHA 6:1 was significantly reduced by PP2 (an inhibitor of Src kinase, FIG. 6) and wortmannin (an inhibitor of PI3-kinase, FIG. 6). Furthermore, the relaxations to EPA:DHA 6:1 were shifted to the right by the membrane permeant analog of SOD, MnTMPyP and catalase (PEG-catalase) and by native SOD and catalase (FIG. 7) in a statistically significant amount. Altogether, these findings suggest that Src kinase and the PI3-kinase mediate the stimulatory signal of EPA:DHA 6:1 to eNOS via a redox-sensitive mechanism.

Figure 8A:
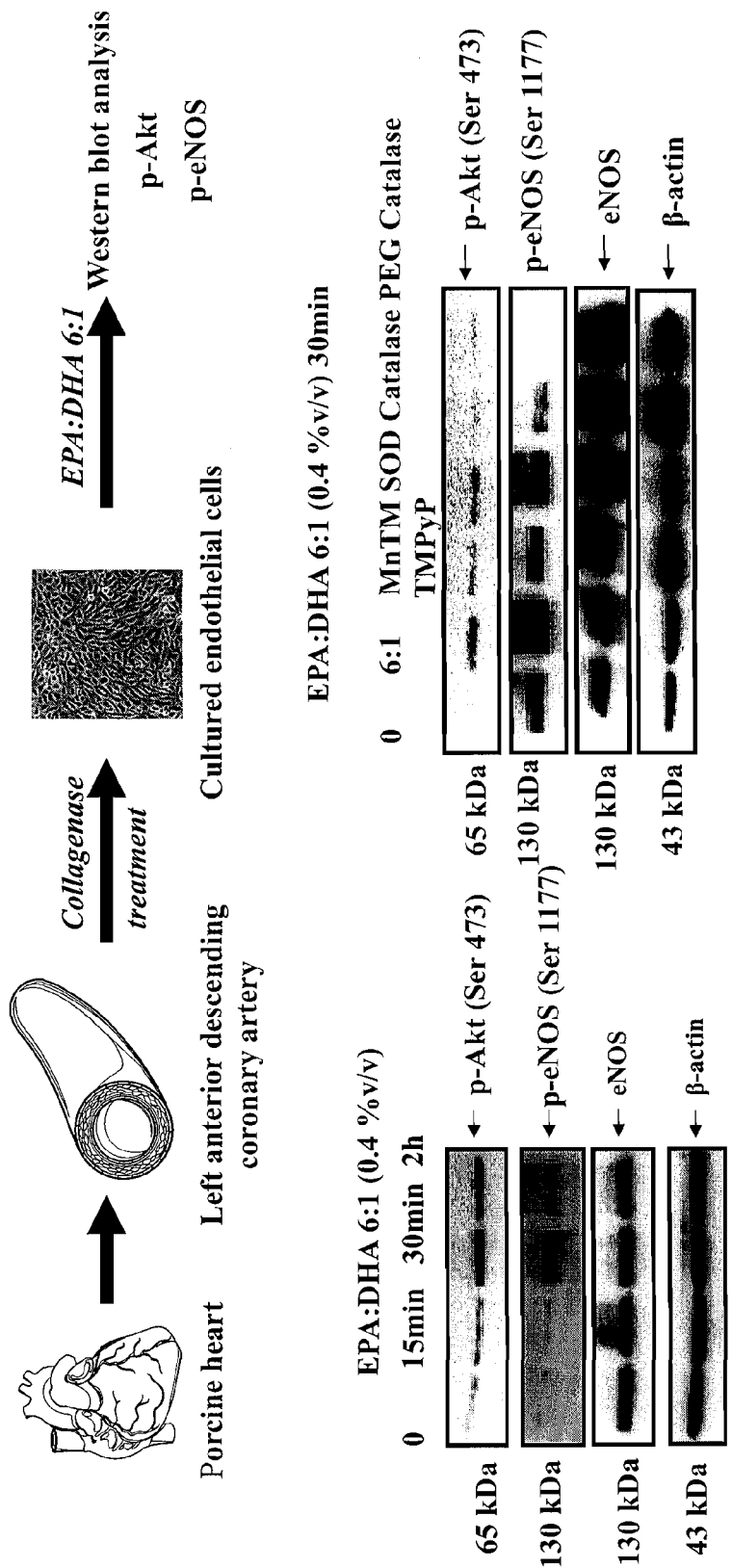
FIG. 8A illustrates the effect EPA:DHA 6:1 has on both Akt and eNOS phosphorylation.
Figure 8B:
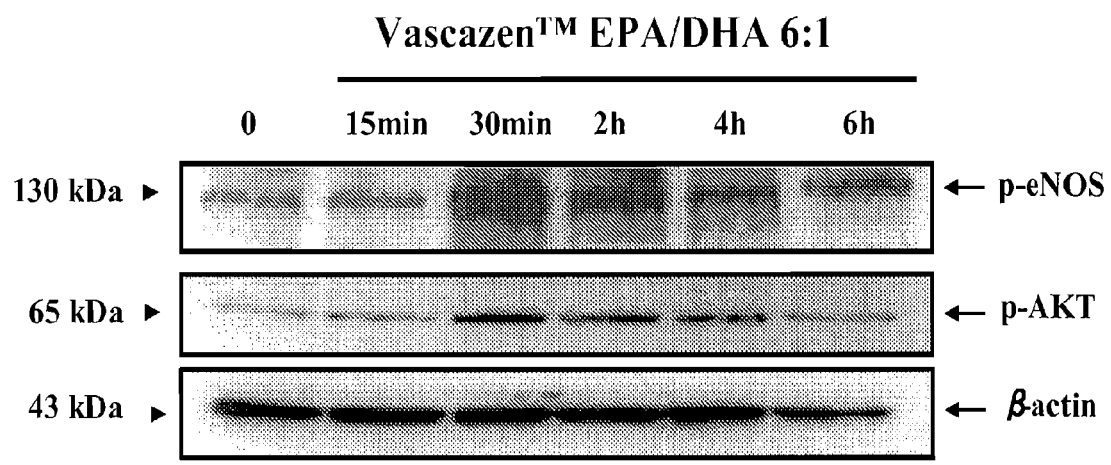
FIG. 8B illustrates Western Blot Data Showing Sustained eNOS Activation of Vascazen at 6 hours at a Concentration of 0.4% and 40 µg of Protein.
Figure 9:
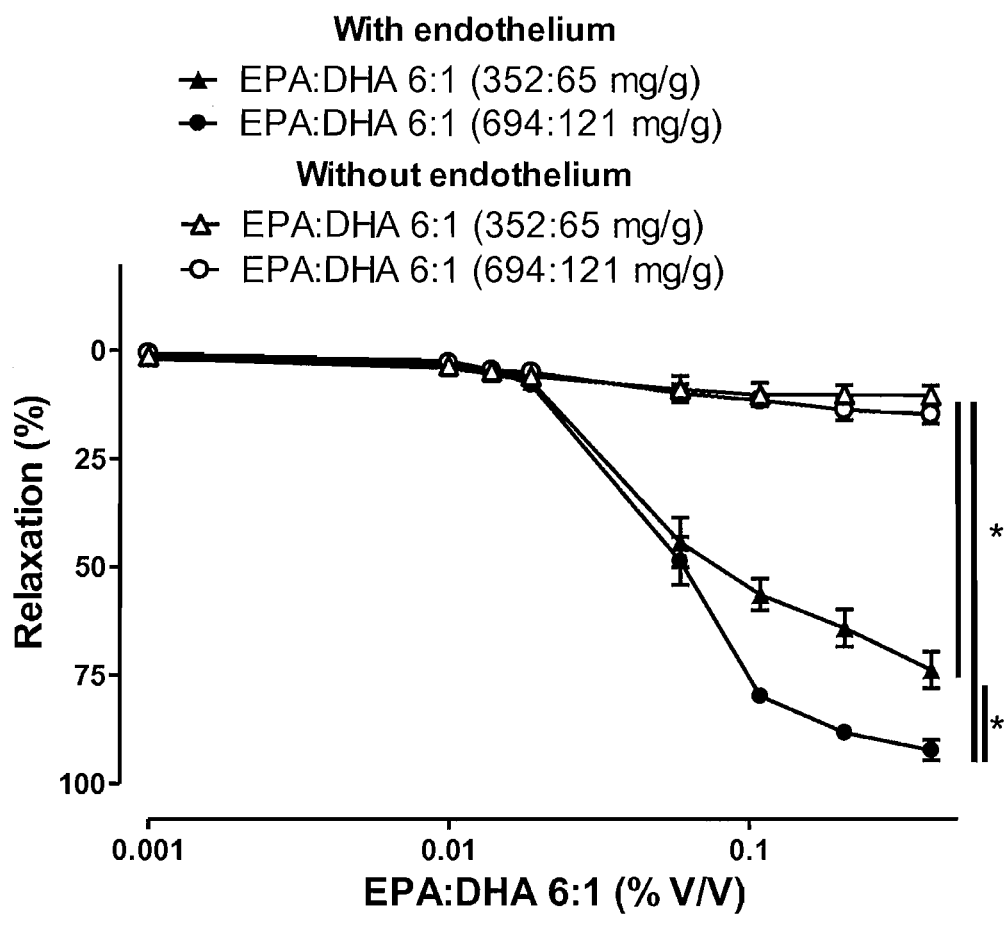
FIG. 9 demonstrates the relation of purity to the sum of EPA+DHA relative to total Omega-3 ratios on the relaxation of coronary artery rings in the presence or absence of endothelium.
Figure 10:
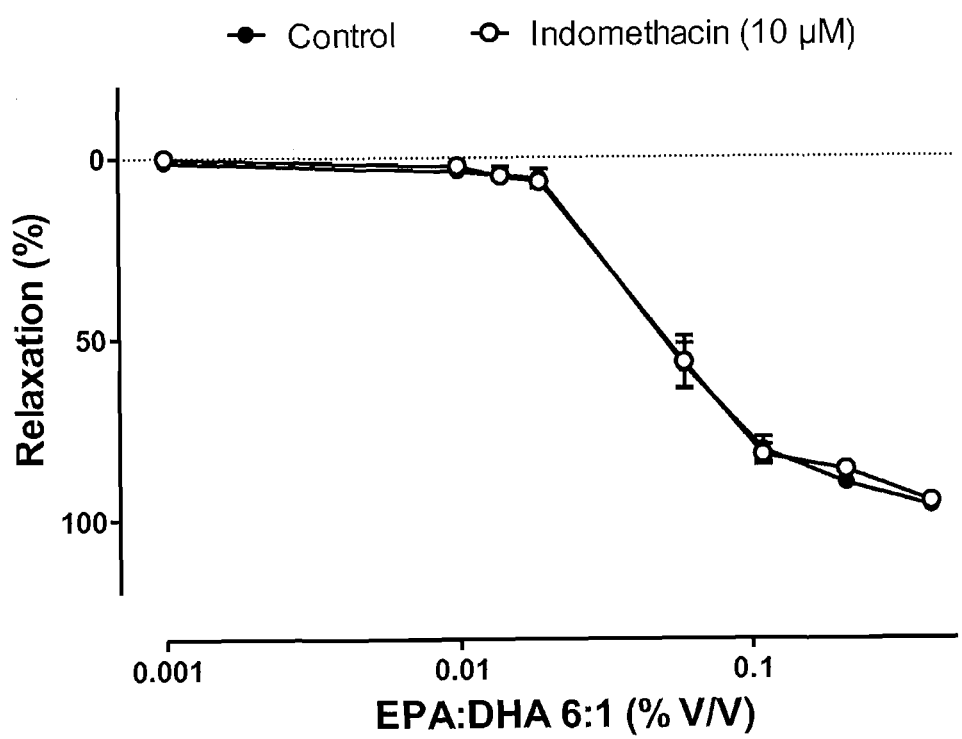
FIG. 10 illustrates that the relaxation effect of the subject EPA:DHA 6:1 formulation is insensitive to the presence of indomethacin.
Figure 11A:
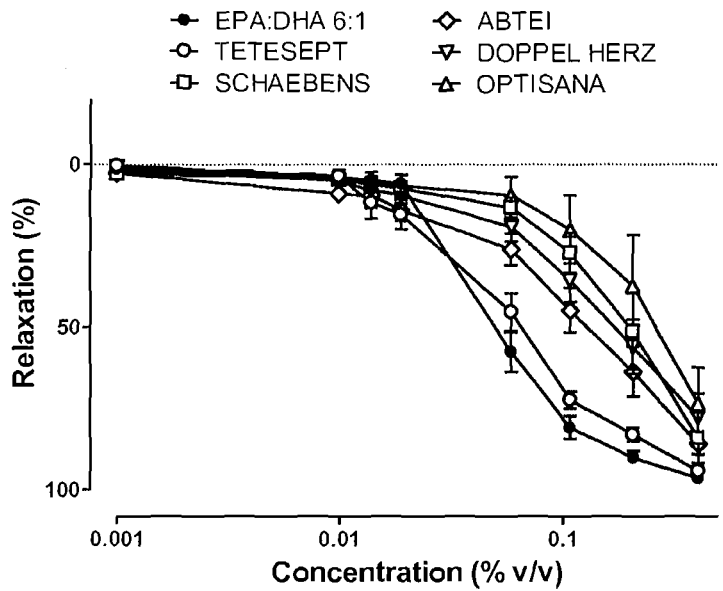
FIG. 11A and FIG. 11B illustrate the indomethacin sensitivity of the relaxation effect of the subject EPA:DHA 6:1 formulation relative to several over the counter Omega-3 products.
Figure 11B:
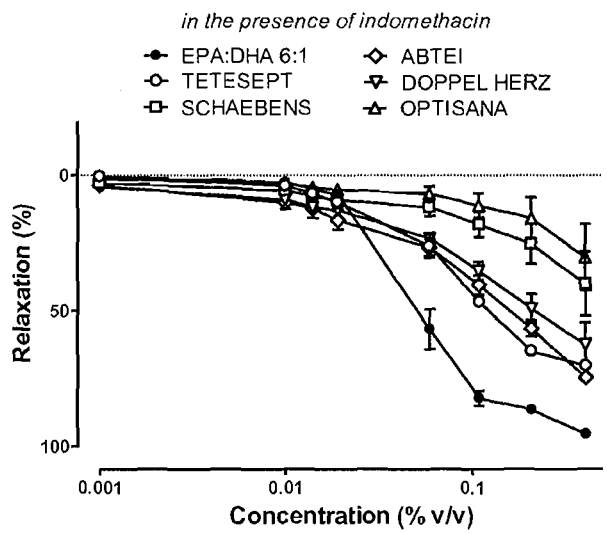

To obtain direct evidence that EPA:DHA 6:1 is able to activate the PI3-kinase/Akt pathway leading to eNOS activation, cultured coronary artery endothelial cells were exposed to EPA:DHA 6:1 up to 6 hours and the level of phosphorylated Akt and eNOS was determined using Western blot. The data indicate that EPA:DHA 6:1 increased the level of phosphorylation of Akt and eNOS starting at 15 min and that this effect persists until 6 h (FIG. 8A and FIG. 8B). The level of total eNOS expression remained unaffected by the EPA:DHA 6:1 treatment (FIG. 8A). In addition, the stimulatory effect of EPA:DHA 6:1 on phosphorylation of Akt and eNOS was inhibited by MnTMPyP, PEG-catalase and by native SOD and catalase (FIG. 8A). Thus, these data provide direct evidence that EPA:DHA 6:1 activate eNOS via a redox-sensitive mechanism dependent relaxation induced by VASCAZEN™ (as an example of EPA:DHA 6:1) is not affected by indomethacin at 10 µM. In contrast, the relaxation induced by TETESEPT™ which was similar to that of EPA:DHA 6:1 was significantly reduced by indomethacin (FIGS. 11A and B). Endothelium-dependent relaxations induced by SCHAEBENS™ and OPTISANA™ were markedly reduced and those to ABTEI™ and DOPPELHER® were slightly reduced (FIGS. 11A and B). These data further indicate that the indomethacin-sensitive relaxation of the OTC Omega-3s cannot be attributed to EPA and DHA nor to its relative concentration ratio but most likely to the presence of additives such as Vitamin E (alpha-tocopherol), see Table 5. Indeed, the vitamin E content of EPA:DHA 6:1 is 0.2% whereas that of OTC Omega-3 formulations varies between 0.85 and 1.1% (Table 5). The importance of the vitamin E additive effect is further suggested by the fact that TETESEPT™ has a more than fivefold higher vitamin E content than that of the EPA:DHA 6:1 formulation. Therefore, the selective inhibitory effect of indomethacin induced upon the TETESEPT™ but not upon the EPA:DHA 6:1 is most likely explained by the more than fivefold higher vitamin E content per capsule. Vitamin E has been shown to cause endothelium-dependent relaxation which is inhibited by indomethacin (Wu et al., J Nutr. 135:

TABLE 5

Comparative Capsule Contents VASCAZEN ™ vs. German Omega-3 OTC Brands

| Product | Weigt/Capsule (mg) | Omega-3 (mg/ %) per Capsule | Vitamin E (mg)/Capsule | Vitamin E (in %)/Capsule | EPA (mg)/Capsule | DHA (mg)/Capsule | EPA + DHA (in %)/Capsule |
|---|---|---|---|---|---|---|---|
| ABTEI | 1767 | 390/22.1 | 15 | 0.85 | 230 | 160 | 22 |
| TETESEPT ® | 1350 | 350/25.9 | 15 | 1.1 | 180 | 120 | 22.2 |
| DOPPELHERZ ® | 1300 | 300/23.1 | 12 | 0.92 | 180 | 120 | 23.1 |
| SCHAEBENS VEGETAL | 1450 | 500/34.5 | 10 | 0.07 | n/a (500 mg linolenic acid) | n/a | — |
| SCHAEBENS FISH OIL | 900 | 195/21.67 | 10 | 1.1 | 117 | 78 | 21.7 |
| OPTISANA ® (LIDL) | 708 | 130/18.4 | 6 | 0.85 | 80 | 50 | 18.4 |
| VASCAZEN ™ | 1000 | 900/90% | 2 | 0.2 | 680 | 110 | 79 |

Omega-3 in % signifies total omega-3 in % of total fatty acids as EE (ethyl esters)

Figure 12:
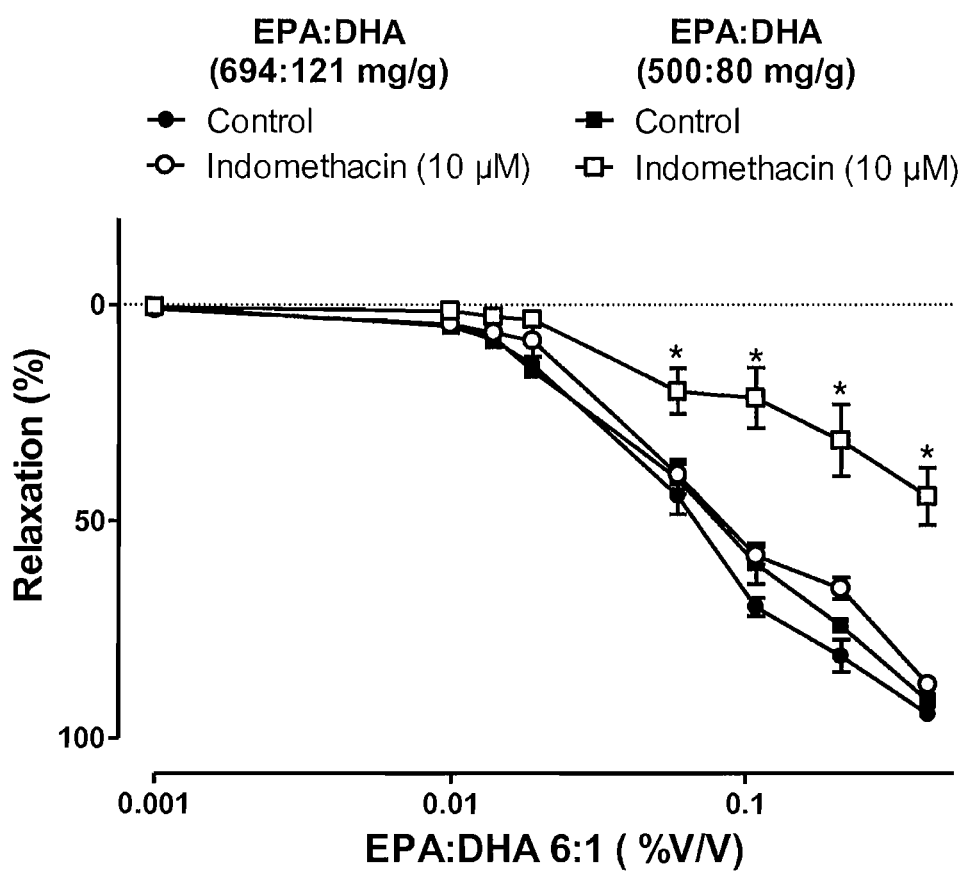
FIG. 12 illustrates the indomethacin sensitivity of the relaxation effect of the EPA:DHA 6:1 formulation relative to a formulation of like ratio containing certain additives.
Figure 13:
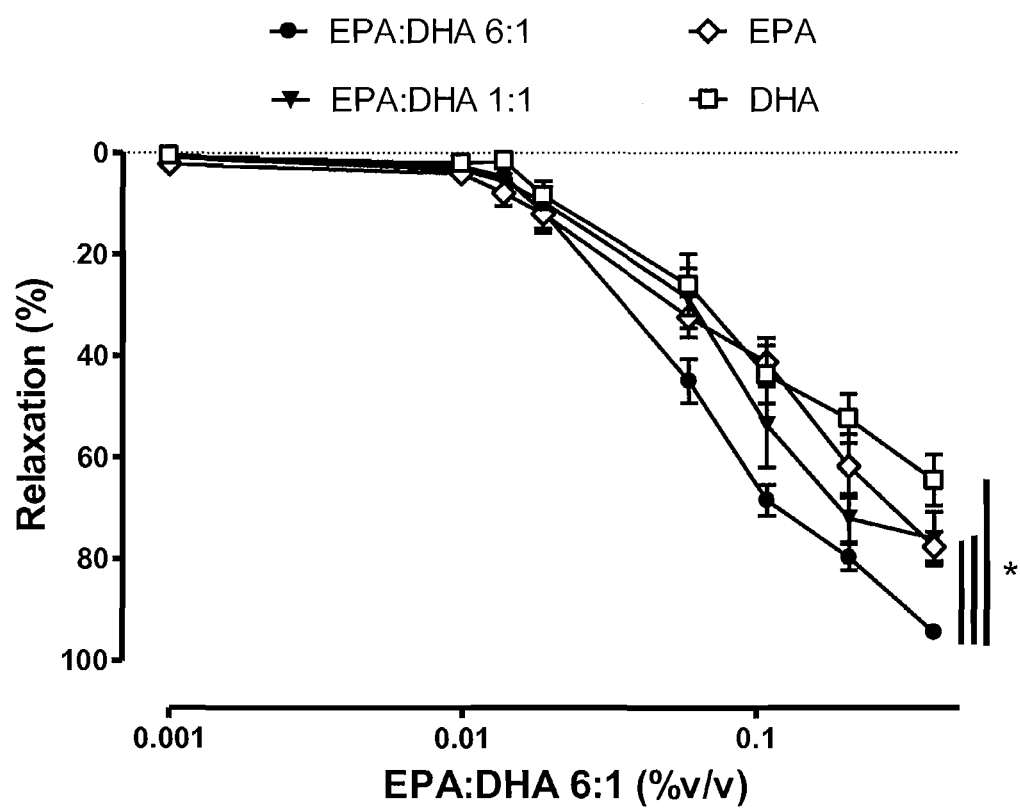
FIG. 13 illustrates the comparative vasorelaxing effect of EPA:DHA 6:1 according to the present invention as compared to EPA:DHA 1:1, EPA alone and DHA alone.

Now referring to FIGS. 9-12, these figures help to illustrate the importance of both the purity of and the presence of additives in the formulation, respectively in providing a maximal relaxation response. For the purpose of this discussion, omega-3 purity was defined as the percentage of the sum of EPA+DHA per capsule. The use of indomethacin as a determinant of the relaxation effect is based upon the following explanation. In some blood vessels vasorelaxing prostanoids such as prostacyclin have been identified as an endotheliun-derived vasorelaxing factor. These vasorelaxing prostanoids are generated from the metabolism of arachidonic acid by cyclooxygenase-1 (COX-1). Indomethacin is an inhibitor of COX-1 and thus will prevent the formation of vasorelaxing prostanoids. The magnitude of the endothelium-dependent relaxation is dependent on the purity of the formulation (FIG. 9) and on the EPA:DHA ratio (FIG. 4). In addition, the EPA:DHA 6:1 formulation caused similar endothelium-dependent relaxation as the OTC Omega-3 product TETESEPT™ with an omega-3 purity (as defined above) of 22.2% as compared to that of the EPA:DHA 6:1 formulation of 75.1% and was much more effective than the other OTC Omega-3s tested (ABTEI LACHSÖL™ 1300, DOPPELHER®, SCHAEBENS™ and OPTISANA™ (FIG. 11A). The endothelium- 1847-1853, 2005). Both omega-3 purity and additives, contribute to the endothelium-dependent relaxation observed with Omega-3 products. This is further illustrated by comparing the relaxation induced by the EPA:DHA 6:1 formulation to that of the METAGENICS™ EPA-DHA 6:1 formulation. Indeed, the latter is markedly inhibited by indomethacin as compared to the former (FIG. 12). Thus, in the presence of indomethacin, the relaxation observed in the presence of Omega-3 products is clearly dependent on omega-3 purity. These experiments underscore the sustained (greater than 6 hours) vasodilatory effect achieved due to the unique ratio and omega-3 purity of the novel EPA:DHA 6:1 product of the present invention. The combination of the 6:1 ratio coupled with the absence of exogenous impurities in the present invention lead to an indomethacin independent vasodilatory effect when compared to either EPA or DHA alone, EPA:DHA 1:1 or to a 6:1 product which contains exogenous impurities (see FIGS. 4,9,11,12 and 13).

Figure 14:
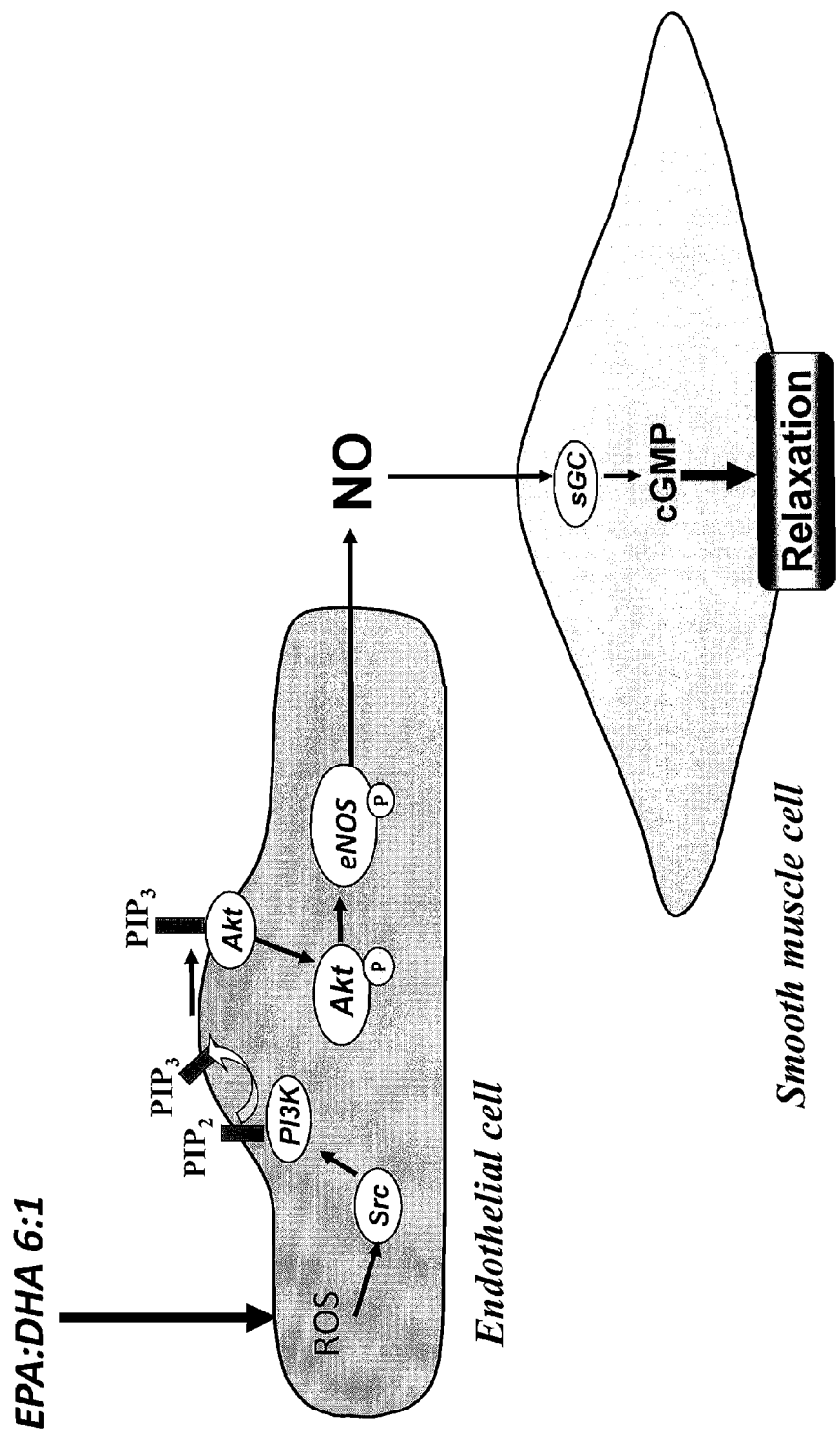
FIG. 14 illustrates the mechanism by which EPA:DHA 6:1 stimulates the endothelial formation of NO via the redox-sensitive activation of the Phosphoinositide 3-Kinase (PI3-Kinase)/Protein Kinase (Akt) pathway.

These findings indicate that omega-3 fatty acid preparations are potent endothelium-dependent vasodilators and that this effect is dependent on the ratio and the omega-3 purity of EPA and DHA within the capsule. They further suggest that omega-3 fatty acids activate eNOS via a redox-sensitive PI3- kinase/Akt pathway leading to changes in the phosphorylation level of eNOS as illustrated in FIG. 14.

Experiment

Physicochemical Characterization and the Kinetic Equilibrium Solubility Comparison Between VASCAZEN™, OMAX3™, and OMEGABRITE™

It is well known that Omega-3 products vary dramatically in their bioavailability. While slight variations in bioavailability are generally not of significance for casual users, whose desire is to ingest these products for maintenance and/or preventive care, a more precise dosing is necessary for therapeutic efficacy. Further studies have indicated the value of ingesting Omega-3 products of relatively high purity. Brhyn et al, "Prostaglandins, Leukotrienes and Essential Fatty Acids", 75 (2006) 19-24, demonstrated that the concentration of Omega-3 fatty acids had independent effects on the uptake and outcomes during short-term administration.

The Omega-3 formulation of the instant invention has an EPA/DHA ratio of about 6:1 (5.7:1 to 6.3:1) and greater than 90% purity. As illustrated herein, studies have shown this product to be superior in the treatment of deficiencies in Omega-3, and thereby a superior product for the treatment of cardiovascular disease in this patient population. In order to determine if the demonstrated effects are a result of a novel and intrinsic property of the formulation, or alternatively are a predictable outgrowth of the use of a high purity (greater than 90%) EPA/DHA formulation, that is EPA/DHA ratio dependent, a testing protocol was undertaken utilizing three commercially available Omega-3 ethyl ester products of high purity having differing ratios of EPA/DHA. The products selected were the Omega 3 formulation of the instant invention, VASCAZEN™ (EPA/DHA=about 6:1), OMAX3™ (EPA/DHA=about 4:1), and OMEGABRITE™ (EPA/DHA=about 7:1). Test criteria were designed to elucidate the bioavailability of each formulation.

VASCAZEN™ (EPA/DHA ratio 6:1), OMAX3™ (EPA/DHA ratio 4:1) and OMEGABRITE™ (EPA/DHA ratio 7:1) are commercially available formulated Omega 3 fish oil products, which are generally differentiated by referencing their stated EPA/DHA ratios. Skilled artisans have theorized that differences in their efficacy and bioavailability may be predictable and directly attributable to variations in the empirical EPA/DHA ratio. The present inventors have determined that, surprisingly, this is not the case. On the contrary, the VASCAZEN™ formulation of the instantly disclosed invention has unique and unexpected properties, which do not correlate to the formulation's intrinsic EPA/DHA ratio.

As will be demonstrated in the following experimental analyses, no correlation or linear relationship was found between the varying EPA/DHA ratios of the three different formulations and their intrinsic kinetic solubility profile, which is a measure of their bioavailability. This is an unexpected finding, and may be explained by the fact that these three formulations differ not only by their ratios but, and most importantly, by the uniqueness of their individual qualitative and quantitative components.

Contrary to what a skilled artisan might have predicted based upon alterations in the empirical ratios of EPA/DHA, the instantly disclosed VASCAZEN™ formulation demonstrates unique properties with regard to vasodilation which are counter-intuitive to what might otherwise have been expected by observing only the EPA/DHA ratio.

In order to demonstrate the uniqueness of the poly-unsaturated fatty acid (Omega-3) formulation of the present invention, a physicochemical characterization of Omega-3 formulations was undertaken. This characterization analyzed the thermodynamic Kinetic and Equilibrium solubility of the selected products—VASCAZEN™, available from Pivotal Therapeutics; OMAX3™, available from Prevention Pharmaceuticals; and OMEGABRITE™, available from Omega Natural Science.

At present, bioequivalence of formulated active pharmaceutical ingredients (APIs) is generally done by measuring $C_{Max}$ (Maximum Serum Concentration) and AUC (Area Under the Curve) in accordance with FDA guidelines. These measurements are cumulative measurements of APIs in biological fluids, e.g. urine, plasma, or serum. They do not measure the change in solubilization of varying amounts of APIs over time.

With regard to unformulated APIs, their cumulative solubilization in vitro is determined by either Log P or Log D measurements, reflecting the octanol/water partition coefficients of non-ionized or ionized APIs, respectively. According to established Log P measurement technologies such as ALOGPS, one would expect a linearity of kinetic solubility, based upon $C_{MAX}$ and AUC values, when combining various ratios of pure EPA and DHA.

An alternative technology for measuring bioequivalence and IVIVC (in vitro in vivo correlation) profiles is the SuperSol 1000 system, available from PREVENTOR, µTBC GmbH, Pfungstadt, Germany. The SuperSol 1000 technology is used routinely for investigating differences in solubilization kinetics in a non-cumulative manner, and has become a standard for determining bioequivalence of generic formulated APIs. The sensitivity and specificity of the SuperSol 1000 system enable the identification of differences in solubilization kinetics of formulations with identical or similar molar API/excipient ratios and provides the capability of predicting API pharmacokinetic parameters such as $C_{MAX}$ and AUC.

Detailed Experiment

The products were chosen with the objective of ascertaining a Kinetic solubility comparison between Omega-3-acid ethyl ester capsules of >90% purity containing different EPA/DHA ratios, e.g., Vascazen™ (EPA/DHA ratio 6:1), Omax3™ (EPA/DHA ratio 4:1) and OmegaBrite™ (EPA/DHA ratio 7:1) using thermodynamic kinetic and equilibrium SuperSol 1000 single run screening solubility analysis. Given the extremely low aqueous solubility of Omega-3-acid ethyl esters, an aqueous solution of 2.5% EtOH was used in order to generate a sufficient base line solubility to allow for subsequent kinetic measurements of the solubilization process of each formulation. A sample volume of 350 µl was injected into the measurement column at 37° C.

DEFINITIONS

The following parameters were measured:

"Early Kinetic Solubility" or "Early Stage Kinetic Solubility" is understood to refer to the solubility kinetics measured in the time period prior to achieving $C_{MAX}$.

"Late Kinetic Solubility" or "Late Stage Kinetic Solubility" is understood to refer to the solubility kinetics measured subsequent to attaining $C_{MAX}$.

$t_{[MSS]}$ is defined as: Time from start of analysis to Maximum Solubilization Speed (min)

$C_{[MSS]}$ is defined as: Early Kinetic Solubility as expressed as concentration at Maximum Solubilization Speed (mg·l$^{-1}$)

$C_{[Eq]}$ is defined as: Late Kinetic Solubility as expressed as Concentration at Equilibrium Kinetic Solubility (mg·l$^{-1}$)

$t_{[Eq]}$ is defined as: Time from start of analysis to Equilibrium Kinetic Solubility (min)

$\Delta C[C_{[Eq]}-C_{[MSS]}]$ is defined as: Difference in Concentration Between Early and Late Kinetic Solubility as defined above (mg·l$^{-1}$)

$\Delta t[t_{[Eq]}-t_{[MSS]}]$ is defined as: Difference in Time Between Early and Late Kinetic Solubility Endpoints (min)

MSS is defined as: Maximum Solubilization Speed (mg·l$^{-1}$·min$^{-1}$) derived as $C_{[MSS]}/t_{[MSS]}$. This is the earliest kinetic solubility indicator for APIs and unformulated APIs.

ISI is defined as: Intrinsic Solubility Index derived as $\Delta C[C_{Eq}-C_{MSS}]/\Delta t[t_{Eq}-t_{MSS}]$ KSR is defined as: Kinetic Solubility Ratio derived as $C_{[MSS]}/C_{[Eq]}$ and is an in vitro parameter measured by the Supersol 1000 technology which correlates to both $C_{MAX}$ and AUC. In order to compare the sustained release profiles of the three formulations as reflected by AUC in vivo, KSR was measured.

The results of the Supersol 1000 analyses of the VASCAZEN™, OMAX3™ and OMEGABRITE™ formulations are summarized in Table 6.

When comparing equimolar concentrations of varying EPA/DHA ratios of Vascazen™, Omax3™ and OmegaBrite™ the similar ISI values found for Vascazen™ and OmegaBrite™, 31.2 and 27.1, respectively reflect a close EPA/DHA ratio (6:1 vs. 7:1) as opposed to the corresponding ISI of OMAX3™, 45.2, that is significantly higher and demonstrates the more pronounced late solubilization of the latter having an EPA/DHA ratio of 4:1 and a higher composite log P than mixtures with a higher EPA/DHA ratio.

The present results are further interpreted in view of the different log P values of EPA and DHA when incorporated into formulations of pharmaceutical grade as well as the qualitative and quantitative presence of other n-3 and n-6 ingredients present. The lower the Log P value, the higher the cumulative solubility of the API. As reported by Tetko I V et al, ALOGPS, VCC Lab, Drug Discovery Today 10 (2005) Pp. 1497-1500, EPA has both a lower theoretical (6.53) and experimental Log P than DHA (6.83) indicative of a slightly lower lipophilicity and solvatation energy. Since the thermodynamic late kinetic solubility kinetics are correlated with log P this signifies that the higher the log P the faster the late solubilization kinetics measured.

TABLE 6

| FORMULATION | MSS | $t_{[MSS]}$ | $C_{[MSS]}$ | $C_{[Eq]}$ | $T_{[Eq]}$ | $\Delta C_{[CEq-CMSS]}$ | $\Delta t_{[tEq-tMSS]}$ | ISI | KSR |
|---|---|---|---|---|---|---|---|---|---|
| Vascazen ™ (6:1)* | 323.9 | 2:17 | 323.9 | 513.8 | 8:25 | 189.9 | 6:08 | 31.2 | 0.63 |
| Omax3 ™ (4:1)* | 371.4 | 2:75 | 371.4 | 627.8 | 8:42 | 256.4 | 5:67 | 45.2 | 0.59 |
| OmegaBrite ™ (7:1)* | 200.1 | 1:96 | 200.1 | 372.8 | 8:33 | 172.7 | 6:37 | 27.1 | 0.54 |

*(EPA/DHA Ratio)

Unexpectedly, the values obtained by the SuperSol technology did not evidence any linearity. No correlation or linear relationship was found between the varying EPA/DHA ratios of the three different formulations and their intrinsic kinetic solubility profile. While not wishing to be bound to any particular theory or mechanism of operation, this may be explained by the fact that these three formulations differ not only by their ratios, but also by their individual qualitative and quantitative components.

The differences in early kinetic solubility between VASCAZEN™ and OMEGABRITE™, however, as reflected by KSR and MSS, are linked neither to log P nor to the ratio itself. Thus, one can only conclude that the enhanced bioavailability of the VASCAZEN™ product is attributable to the other specific fatty acids present, e.g. the qualitative and quantitative nature of other non-EPA and non-DHA n-3 and n-6 ingredients, as further illustrated in Table 7.

TABLE 7

| C:unsat-pos | Common Name | AVG (n = 9) | SD | Range = AVG ± 2SD | | 2 × SD |
|---|---|---|---|---|---|---|
| C18:3 N3 + C18:4 N3 | Alpha Linolenic Acid + Stearidonic Acid | 3.33 | 0.06 | 3.21 | 3.45 | 0.12 |
| C20:4 N6 | Arachidonic Acid | 3.26 | 0.11 | 3.04 | 3.48 | 0.22 |
| C20:5 N3 (EPA) | Eicosapentanoic Acid (EPA) | 72.40 | 0.99 | 70.42 | 74.38 | 1.98 |
| C22:5 N3 (DPA) | Docosapentanoic Acid (n3) DPA | 2.83 | 0.15 | 2.53 | 3.13 | 0.30 |
| C22:6 N3 (DHA) | Docodahexanoic Acid (DHA) | 12.90 | 0.29 | 12.32 | 13.48 | 0.58 |
| | % of total Fatty acid | | | | | |
| | Omega-3 | 94.01 | 0.43 | 93.15 | 94.87 | 0.86 |
| | Omega-6 | 4.42 | 0.38 | 3.66 | 5.18 | 0.76 |
| | % of total Fatty acid | | | | | |
| | EPA + DHA | 85.22 | 1.30 | 82.62 | 87.82 | 2.60 |
| | EPA + DHA + DPA | 88.06 | 1.17 | 85.72 | 90.40 | 2.34 |
| | 18:3 n3-Alpha Linolenic Acid(ALA) | 0.35 | 0.03 | 0.29 | 0.41 | 0.06 |

TABLE 7-continued

| C:unsat-pos | | AVG (n = 9) | SD | Range = AVG ± 2SD | | 2 × SD |
|---|---|---|---|---|---|---|
| | 18:4 n3-Stearidonic acid (SDA) | 2.98 | 0.06 | 2.86 | 3.10 | 0.12 |
| | ALA + SDA | 3.33 | 0.06 | 3.21 | 3.45 | 0.12 |
| | % of Total Omega 3 | | | | | |
| | EPA + DHA | 90.66 | 1.20 | 88.26 | 93.06 | 2.40 |
| | EPA + DHA + DPA | 93.66 | 1.14 | 91.38 | 95.94 | 2.28 |
| | 18:3 n3-Alpha Linolenic Acid(ALA) | 0.37 | 0.04 | 0.29 | 0.45 | 0.08 |
| | 18:4 n3-Stearidonic acid (SDA) | 3.17 | 0.07 | 3.03 | 3.31 | 0.14 |
| | ALA + SDA | 3.54 | 0.07 | 3.40 | 3.68 | 0.14 |

Several lots of the VASCAZEN™ formulation, as illustrated in Table 7, were analyzed. Three distinct formulation lots were analyzed in triplicate using different laboratories to yield 9 data points (n=9). This analysis yields numerical ranges, calculated as the average value plus or minus two standard deviations (Avg±2 (SD)), which constitute acceptable variations in fatty acid contents for the instant formulation. Formulations within these ranges have been shown to have superior bioavailability, as illustrated by the instant physico-chemical characterization. At the same time, these formulations exhibit a unique and desirable stable and sustained long-acting vasodilatory effect, as has been previously demonstrated herein.

Based upon the data in Table 7, the instantly disclosed composition for treatment or prophylaxis of risk factors for cardiovascular disease (CVD) and protection against sudden death in patients with cardiovascular disease may be defined as a mixture containing omega-3 fatty acids including eicosapentaenoic acid (EPA), docosahexaenoic acid (DHA), and docosapentaenoic acid (DPA) wherein the weight ratio of EPA:DHA is in the range of 5.7:1-6.3:1, and the amount of EPA+DHA in the formulation is about 82.62% to about 87.82% by weight of the total fatty acid content of the formulation, and about 88.26% to about 93.06% by weight of the total omega-3 content of the formulation; the formulation contains from about 93.15% to about 94.87% by weight omega-3 fatty acids, and the sum of EPA, DHA and DPA are from about 85.72% to about 87.82% by weight of the % of total fatty acids in the formulation, and from about 91.38% to about 95.94% by weight of the total % of omega-3 present in the formulation; said formulation contains about 2.53% to about 3.13% by weight of the % of total fatty acids in the formulation of DPA, about 3.04% to about 3.48% by weight of the % of total fatty acids in the formulation of arachidonic acid (AA), and about 3.21% to about 3.45% by weight of the % of total fatty acids in the formulation, of omega-3 fatty acids having 18 carbon atoms, wherein said 18 carbon atom omega-3 fatty acids are alpha-linolenic acid (ALA) and stearidonic acid (SDA). The sum of ALA and SDA is about 3.40% to about 3.68% by weight of the total % of omega-3 present in the formulation.

The above data demonstrate that there is no linearity or trend tying the physical characteristics of the test formulations to their EPA/DHA ratios. Furthermore, the data demonstrate a higher bioavailability and solubility for the VASCAZEN™ formulation, which supports the hypothesis that the sustained vasodilation effects achieved by the VASCAZEN™ product are attributable to the unique blend of fatty acids present, and result in a formulation having heretofore unexpected characteristics.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A pharmaceutical formulation for treatment or prophylaxis of risk factors for cardiovascular disease (CVD), protection against sudden death in patients with cardiovascular disease, reduction of overall serum cholesterol levels, reductions in high blood pressure, increase in the HDL:LDL ratio, and reduction of triglycerides, by exhibiting a sustained vasodilatory effect comprising:

a mixture containing omega-3 fatty acids including eicosapentaenoic acid (EPA), docosahexaenoic acid (DHA), and docosapentaenoic acid (DPA) wherein the weight ratio of EPA:DHA is in the range of 5.7:1-6.3:1; the formulation contains about 90% or more by weight omega-3 fatty acids, and the EPA, DHA and DPA comprise about 82% by weight of the content of the formulation; said formulation contains about 25 mg/g of DPA, about 30 mg/g of arachidonic acid (AA), and about 30 mg/g of one or more omega-3 fatty acids having 18 carbon atoms, wherein said 18 carbon atom omega-3 fatty acid is selected from the group consisting of alpha-linolenic acid (ALA), stearidonic acid (SDA) and combinations thereof; and at least one azetidinone cholesterol absorption inhibitor or pharmaceutically acceptable salt thereof or a combination thereof.

2. The formulation in accordance with claim 1 wherein the omega-3 fatty acids are in the form of triglycerides and pharmaceutically acceptable salts thereof.

3. The formulation in accordance with claim 1 wherein the omega-3 fatty acids are in the form of phospholipids and pharmaceutically acceptable salts thereof.

4. The formulation in accordance with claim 1 wherein the formulation additionally comprises a stabilizer.

5. The formulation in accordance with claim 4 wherein the stabilizer is tocopherol in an amount of about 0.2%.

6. The formulation in accordance with claim 1 wherein the unit dosage form comprises tablets, capsules, pills, powders, granules, and oral solutions or suspensions.

7. The formulation in accordance with claim 6 wherein the unit dosage form is a gel or liquid capsule.

8. The formulation in accordance with claim 1 wherein the omega-3 fatty acids are in the form of ethyl esters and pharmaceutically acceptable salts thereof.

9. A pharmaceutical formulation for treatment or prophylaxis of risk factors for cardiovascular disease (CVD), protection against sudden death in patients with cardiovascular disease, reduction of overall serum cholesterol levels, reductions in high blood pressure, increase in the HDL:LDL ratio, and reduction of triglycerides, by exhibiting a sustained vasodilatory effect, comprising:
a mixture containing omega-3 fatty acids including eicosapentaenoic acid (EPA), docosahexaenoic acid (DHA), and docosapentaenoic acid (DPA) wherein the weight ratio of EPA:DHA is in the range of 5.7:1-6.3:1, the amount of EPA+DHA in the formulation is about 82.62% to about 87.82% by weight of the total fatty acid content of the formulation, and about 88.26% to about 93.06% by weight of the total omega-3 content of the formulation; the formulation contains from about 93.15% to about 94.87% by weight omega-3 fatty acids; the sum of EPA, DHA and DPA are from about 85.72% to about 87.82% by weight of the total fatty acids in the formulation, and from about 91.38% to about 95.94% by weight of the total omega-3 present in the formulation; said formulation contains about 2.53% to about 3.13% by weight of the total fatty acids in the formulation of DPA, about 3.04% to about 3.48% by weight of the total fatty acids in the formulation of arachidonic acid (AA), and about 3.21% to about 3.45% by weight of the total fatty acids in the formulation, of omega-3 fatty acids having 18 carbon atoms, wherein said 18 carbon atom omega-3 fatty acids are alpha-linolenic acid (ALA) and stearidonic acid (SDA); and wherein the sum of ALA and SDA is about 3.40% to about 3.68% by weight of the total omega-3 present in the formulation; and
at least one azetidinone cholesterol absorption inhibitor or pharmaceutically acceptable salt thereof or a combination thereof.

10. A process for the treatment of risk factors for cardiovascular disease (CVD), protection against sudden death in patients with cardiovascular disease, reduction of overall serum cholesterol levels, reductions in high blood pressure, increase in the HDL:LDL ratio, and reduction of triglycerides and homocysteine levels comprising:
identifying a patient population that exhibits deficiencies in omega-3 fatty acids, and administering to said patient population a formulation in accordance with claim 1; whereby a therapeutic effect is achieved.

11. A process for the treatment of risk factors for cardiovascular disease (CVD), protection against sudden death in patients with cardiovascular disease, reduction of overall serum cholesterol levels, reductions in high blood pressure, increase in the HDL:LDL ratio, and reduction of triglycerides and homocysteine levels comprising:
identifying a patient population that exhibits deficiencies in omega-3 fatty acids, and administering to said patient population a formulation in accordance with claim 9; whereby a therapeutic effect is achieved.

12. A process in accordance with claim 1 for achieving an indomethacin-independent sustained vasodilatory effect comprising:
identifying a patient population that exhibits deficiencies in omega-3 fatty acids; and
administering to said patient population a formulation in accordance with claim 1;
whereby a therapeutic effect is achieved.

13. A process in accordance with claim 9 for achieving an indomethacin-independent sustained vasodilatory effect comprising:
identifying a patient population that exhibits deficiencies in omega-3 fatty acids; and
administering to said patient population a formulation in accordance with claim 9;
whereby a therapeutic effect is achieved.

14. The formulation in accordance with claim 9 wherein the omega-3 fatty acids are in the form of ethyl esters and pharmaceutically acceptable salts thereof.

15. The formulation in accordance with claim 9 wherein the omega-3 fatty acids are in the form of triglycerides and pharmaceutically acceptable salts thereof.

16. The formulation in accordance with claim 9 wherein the omega-3 fatty acids are in the form of phospholipids and pharmaceutically acceptable salts thereof.

17. The formulation in accordance with claim 9 wherein the formulation additionally comprises a stabilizer.

18. The formulation in accordance with claim 17 wherein the stabilizer is tocopherol in an amount of about 0.2%.

19. The formulation in accordance with claim 9 wherein the unit dosage form comprises tablets, capsules, pills, powders, granules, and oral solutions or suspensions.

20. The formulation in accordance with claim 19 wherein the unit dosage form is a gel or liquid capsule.

* * * * *